US012571024B2

(12) United States Patent
Nugent et al.

(10) Patent No.: US 12,571,024 B2
(45) Date of Patent: Mar. 10, 2026

(54) METHODS AND COMPOSITIONS RELATING TO COVALENTLY CLOSED NUCLEIC ACIDS

(71) Applicant: Twist Bioscience Corporation, South San Francisco, CA (US)

(72) Inventors: Rebecca Nugent, San Francisco, CA (US); Siyuan Chen, San Mateo, CA (US); Nathan Raynard, San Mateo, CA (US)

(73) Assignee: Twist Bioscience Corporation, South San Francisco, CA (US)

( * ) Notice: Subject to any disclaimer, the term of this patent is extended or adjusted under 35 U.S.C. 154(b) by 821 days.

(21) Appl. No.: 17/820,856

(22) Filed: Aug. 18, 2022

(65) Prior Publication Data

US 2023/0115861 A1    Apr. 13, 2023

Related U.S. Application Data

(60) Provisional application No. 63/235,069, filed on Aug. 19, 2021.

(51) Int. Cl.
*C12Q 1/6806* (2018.01)
*C12N 15/10* (2006.01)
*C12P 19/34* (2006.01)

(52) U.S. Cl.
CPC ....... *C12Q 1/6806* (2013.01); *C12N 15/1093* (2013.01); *C12P 19/34* (2013.01)

(58) Field of Classification Search
CPC .. C12Q 1/6806; C12N 15/1093; C12N 15/64; C12N 15/111; C12N 2310/532; C12P 19/34
See application file for complete search history.

(56) References Cited

U.S. PATENT DOCUMENTS

| | | | |
|---|---|---|---|
| 5,368,823 A | 11/1994 | McGraw et al. | |
| 5,474,796 A | 12/1995 | Brennan | |
| 5,534,507 A | 7/1996 | Cama et al. | |
| 5,677,195 A | 10/1997 | Winkler et al. | |
| 5,843,767 A | 12/1998 | Beattie | |
| 6,013,440 A | 1/2000 | Lipshutz et al. | |
| 6,028,189 A | 2/2000 | Blanchard | |
| 6,419,883 B1 | 7/2002 | Blanchard | |
| 6,472,147 B1 | 10/2002 | Janda et al. | |
| 6,492,107 B1 | 12/2002 | Kauffman et al. | |
| 6,893,816 B1 | 5/2005 | Beattie | |
| 7,163,660 B2 | 1/2007 | Lehmann | |
| 7,202,264 B2 | 4/2007 | Ravikumar et al. | |
| 8,198,071 B2 | 6/2012 | Goshoo et al. | |
| 9,403,141 B2 | 8/2016 | Banyai et al. | |
| 9,409,139 B2 | 8/2016 | Banyai et al. | |
| 9,555,388 B2 | 1/2017 | Banyai et al. | |
| 9,677,067 B2 | 6/2017 | Toro et al. | |
| 9,745,619 B2 | 8/2017 | Rabbani et al. | |
| 9,765,387 B2 | 9/2017 | Rabbani et al. | |

| | | | |
|---|---|---|---|
| 9,833,761 B2 | 12/2017 | Banyai et al. | |
| 9,839,894 B2 | 12/2017 | Banyai et al. | |
| 9,889,423 B2 | 2/2018 | Banyai et al. | |
| 9,895,673 B2 | 2/2018 | Peck et al. | |
| 9,981,239 B2 | 5/2018 | Banyai et al. | |
| 10,053,688 B2 | 8/2018 | Cox | |
| 10,272,410 B2 | 4/2019 | Banyai et al. | |
| 10,384,188 B2 | 8/2019 | Banyai et al. | |
| 10,384,189 B2 | 8/2019 | Peck | |
| 10,417,457 B2 | 9/2019 | Peck | |
| 10,583,415 B2 | 3/2020 | Banyai et al. | |
| 10,618,024 B2 | 4/2020 | Banyai et al. | |
| 10,632,445 B2 | 4/2020 | Banyai et al. | |
| 10,639,609 B2 | 5/2020 | Banyai et al. | |
| 10,669,304 B2 | 6/2020 | Indermuhle et al. | |
| 10,744,477 B2 | 8/2020 | Banyai et al. | |
| 10,754,994 B2 | 8/2020 | Peck | |
| 10,773,232 B2 | 9/2020 | Banyai et al. | |
| 10,844,373 B2 | 11/2020 | Cox et al. | |
| 10,894,242 B2 | 1/2021 | Marsh et al. | |
| 10,894,959 B2 | 1/2021 | Cox et al. | |
| 10,907,274 B2 | 2/2021 | Cox | |
| 10,936,953 B2 | 3/2021 | Bramlett et al. | |
| 10,969,965 B2 | 4/2021 | Malina et al. | |
| 10,975,372 B2 | 4/2021 | Cox et al. | |
| 10,987,648 B2 | 4/2021 | Peck et al. | |
| 11,185,837 B2 | 11/2021 | Banyai et al. | |
| 11,214,798 B2 | 1/2022 | Brown | |

(Continued)

FOREIGN PATENT DOCUMENTS

| | | |
|---|---|---|
| CN | 101277758 A | 10/2008 |
| EP | 3030682 A2 | 6/2016 |

(Continued)

OTHER PUBLICATIONS

Agbavwe et al.: Efficiency, Error and Yield in Light-Directed Maskless Synthesis of DNA Microarrays. Journal of Nanobiotechnology. 9(57):1-17 (2011).
Altschul et al.: Basic Local Alignment Search Tool. J. Mol. Biol. 215: 403-410 (1990).
Altschul et al.: Gapped BLAST and PSI-BLAST: A new generation of protein database search programs. Nuc. Acids Res. 25: 3389-3402 (1997).
Arkles et al.: The Role of Polarity in the Structure of Silanes Employed in Surface Modification. Silanes and Other Coupling Agents. 5:51-64 (2009).
ATDBio. Nucleic Acid Structure, Nucleic Acids Book, 9 pages, published on Jan. 22, 2005. from: http://www.atdbio.com/content/5/Nucleic-acid-structure.
ATDBio. Solid-Phase Oligonucleotide Synthesis, Nucleic Acids Book, 20 pages, Published on Jul. 31, 2011. from: http://www.atdbio.com/content/17/Solid-phase-oligonucleotide-synthesis.

(Continued)

*Primary Examiner* — Cynthia B Wilder
(74) *Attorney, Agent, or Firm* — Bookoff McAndrews, PLLC

(57) ABSTRACT

Provided herein are methods, systems, and compositions for assembly of covalently closed double stranded nucleic acids. Provided herein are methods, systems, and compositions for assembly covalently closed double stranded nucleic acids for use in various downstream processes.

27 Claims, 18 Drawing Sheets

Specification includes a Sequence Listing.

(56) References Cited

U.S. PATENT DOCUMENTS

| | | | |
|---|---|---|---|
| 11,263,354 B2 | 3/2022 | Peck |
| 11,332,738 B2 | 5/2022 | Nugent et al. |
| 11,332,740 B2 | 5/2022 | Nugent et al. |
| 11,377,676 B2 | 7/2022 | Wu et al. |
| 11,407,837 B2 | 8/2022 | Glanville |
| 11,452,980 B2 | 9/2022 | Banyai et al. |
| 11,492,665 B2 | 11/2022 | Zeitoun et al. |
| 11,492,727 B2 | 11/2022 | Tabibiazar et al. |
| 11,492,728 B2 | 11/2022 | Sato |
| 2001/0018512 A1 | 8/2001 | Blanchard |
| 2002/0025561 A1 | 2/2002 | Hodgson |
| 2002/0094533 A1 | 7/2002 | Hess et al. |
| 2002/0095073 A1 | 7/2002 | Jacobs et al. |
| 2002/0160536 A1 | 10/2002 | Regnier et al. |
| 2002/0164824 A1 | 11/2002 | Xiao et al. |
| 2003/0120035 A1 | 6/2003 | Gao et al. |
| 2003/0171325 A1 | 9/2003 | Gascoyne et al. |
| 2004/0087008 A1 | 5/2004 | Schembri |
| 2004/0259146 A1 | 12/2004 | Friend et al. |
| 2005/0137805 A1 | 6/2005 | Lewin et al. |
| 2005/0227235 A1 | 10/2005 | Carr et al. |
| 2006/0127920 A1 | 6/2006 | Church et al. |
| 2007/0196834 A1 | 8/2007 | Cerrina et al. |
| 2008/0085511 A1 | 4/2008 | Peck et al. |
| 2008/0085514 A1 | 4/2008 | Peck et al. |
| 2008/0227160 A1 | 9/2008 | Kool |
| 2008/0287320 A1 | 11/2008 | Baynes et al. |
| 2008/0300842 A1 | 12/2008 | Govindarajan et al. |
| 2009/0062129 A1 | 3/2009 | McKernan et al. |
| 2009/0239759 A1 | 9/2009 | Balch |
| 2009/0285825 A1 | 11/2009 | Kini et al. |
| 2010/0004143 A1 | 1/2010 | Shibahara |
| 2010/0099103 A1 | 4/2010 | Hsieh et al. |
| 2010/0111768 A1 | 5/2010 | Banerjee et al. |
| 2010/0216648 A1 | 8/2010 | Staehler et al. |
| 2010/0311960 A1 | 12/2010 | Dellinger |
| 2011/0172127 A1 | 7/2011 | Jacobson et al. |
| 2011/0217738 A1 | 9/2011 | Jacobson |
| 2012/0129704 A1 | 5/2012 | Gunderson et al. |
| 2012/0164691 A1 | 6/2012 | Eshoo et al. |
| 2012/0231968 A1 | 9/2012 | Bruhn et al. |
| 2012/0264653 A1 | 10/2012 | Carr et al. |
| 2013/0017642 A1 | 1/2013 | Milgrew et al. |
| 2013/0017977 A1 | 1/2013 | Oleinikov |
| 2013/0065017 A1 | 3/2013 | Sieber |
| 2013/0109595 A1 | 5/2013 | Routenberg |
| 2013/0109596 A1 | 5/2013 | Peterson et al. |
| 2013/0130321 A1 | 5/2013 | Staehler et al. |
| 2013/0165328 A1 | 6/2013 | Previte et al. |
| 2014/0106394 A1 | 4/2014 | Ko et al. |
| 2014/0178992 A1 | 6/2014 | Nakashima et al. |
| 2015/0038373 A1 | 2/2015 | Banyai et al. |
| 2015/0120265 A1 | 4/2015 | Amirav-Drory et al. |
| 2015/0196917 A1 | 7/2015 | Kay et al. |
| 2016/0089651 A1 | 3/2016 | Banyai |
| 2016/0090592 A1 | 3/2016 | Banyai et al. |
| 2016/0096160 A1 | 4/2016 | Banyai et al. |
| 2016/0251651 A1 | 9/2016 | Banyai et al. |
| 2016/0303535 A1 | 10/2016 | Banyai et al. |
| 2016/0333340 A1 | 11/2016 | Wu |
| 2016/0339409 A1 | 11/2016 | Banyai et al. |
| 2016/0340672 A1 | 11/2016 | Banyai et al. |
| 2016/0354752 A1 | 12/2016 | Banyai et al. |
| 2017/0081716 A1 | 3/2017 | Peck |
| 2017/0088833 A1 * | 3/2017 | Joung ............... C12N 15/1031 |
| 2017/0095785 A1 | 4/2017 | Banyai et al. |
| 2017/0159044 A1 | 6/2017 | Toro et al. |
| 2017/0327819 A1 | 11/2017 | Banyai et al. |
| 2017/0357752 A1 | 12/2017 | Diggans |
| 2017/0362589 A1 | 12/2017 | Banyai et al. |
| 2018/0029001 A1 | 2/2018 | Banyai et al. |
| 2018/0104664 A1 | 4/2018 | Fernandez |
| 2018/0142289 A1 | 5/2018 | Zeitoun et al. |
| 2018/0253563 A1 | 9/2018 | Peck et al. |
| 2018/0264428 A1 | 9/2018 | Banyai et al. |
| 2018/0282721 A1 | 10/2018 | Cox et al. |
| 2018/0326388 A1 | 11/2018 | Banyai et al. |
| 2019/0194692 A1 | 6/2019 | Meijrink et al. |
| 2019/0314783 A1 | 10/2019 | Banyai et al. |
| 2019/0352635 A1 | 11/2019 | Toro et al. |
| 2019/0366293 A1 | 12/2019 | Banyai et al. |
| 2019/0366294 A1 | 12/2019 | Banyai et al. |
| 2020/0071713 A1 | 3/2020 | Sayre et al. |
| 2020/0102611 A1 | 4/2020 | Zeitoun et al. |
| 2020/0156037 A1 | 5/2020 | Banyai et al. |
| 2020/0181667 A1 | 6/2020 | Wu et al. |
| 2020/0222875 A1 | 7/2020 | Peck et al. |
| 2020/0283760 A1 | 9/2020 | Nugent et al. |
| 2020/0299322 A1 | 9/2020 | Indermuhle et al. |
| 2020/0299684 A1 | 9/2020 | Toro et al. |
| 2020/0330953 A1 | 10/2020 | Banyai et al. |
| 2021/0002710 A1 | 1/2021 | Gantt et al. |
| 2021/0040476 A1 | 2/2021 | Cox et al. |
| 2021/0071168 A1 | 3/2021 | Nugent et al. |
| 2021/0102192 A1 | 4/2021 | Tabibiazar et al. |
| 2021/0102195 A1 | 4/2021 | Sato et al. |
| 2021/0102198 A1 | 4/2021 | Cox et al. |
| 2021/0115594 A1 | 4/2021 | Cox et al. |
| 2021/0123098 A1 | 4/2021 | Previte et al. |
| 2021/0129108 A1 | 5/2021 | Marsh et al. |
| 2021/0142182 A1 | 5/2021 | Bramlett et al. |
| 2021/0164029 A1 | 6/2021 | Sekedat et al. |
| 2021/0170356 A1 | 6/2021 | Peck et al. |
| 2021/0179724 A1 | 6/2021 | Sato et al. |
| 2021/0180046 A1 | 6/2021 | Cox et al. |
| 2021/0207197 A1 | 7/2021 | Gantt et al. |
| 2021/0332078 A1 | 10/2021 | Wu |
| 2021/0348220 A1 | 11/2021 | Zeitoun et al. |
| 2021/0355194 A1 | 11/2021 | Sato et al. |
| 2021/0395344 A1 | 12/2021 | Sato et al. |
| 2022/0032256 A1 | 2/2022 | Lackey et al. |
| 2022/0064206 A1 | 3/2022 | Fernandez et al. |
| 2022/0064313 A1 | 3/2022 | Sato et al. |
| 2022/0064628 A1 | 3/2022 | Toro et al. |
| 2022/0106586 A1 | 4/2022 | Nugent et al. |
| 2022/0106590 A1 | 4/2022 | Arbiza et al. |
| 2022/0135690 A1 | 5/2022 | Sato et al. |
| 2022/0135965 A1 | 5/2022 | Gantt et al. |
| 2022/0138354 A1 | 5/2022 | Peck |
| 2022/0145289 A1 | 5/2022 | Lackey et al. |
| 2022/0206001 A1 | 6/2022 | Sato |
| 2022/0243195 A1 | 8/2022 | Nugent et al. |
| 2022/0246236 A1 | 8/2022 | Amirav-Drory |
| 2022/0259319 A1 | 8/2022 | Sato et al. |
| 2022/0259638 A1 | 8/2022 | Brown |
| 2022/0277808 A1 | 9/2022 | Arbiza et al. |
| 2022/0281989 A1 | 9/2022 | Glanville |
| 2022/0307010 A1 | 9/2022 | Sato et al. |
| 2022/0315971 A1 | 10/2022 | Wu et al. |
| 2022/0323924 A1 | 10/2022 | Lackey et al. |
| 2022/0325276 A2 | 10/2022 | Banyai et al. |
| 2022/0325278 A1 | 10/2022 | Nugent et al. |
| 2022/0348659 A1 | 11/2022 | Sato et al. |

FOREIGN PATENT DOCUMENTS

| | | | | | |
|---|---|---|---|---|---|
| JP | H07505530 A | 6/1995 |
| JP | 2001518086 A | 10/2001 |
| JP | 2002538790 A | 11/2002 |
| JP | 2004268394 A | 9/2004 |
| JP | 2006503586 A | 2/2006 |
| JP | 2008214343 A | 9/2008 |
| JP | 2009294195 A | 12/2009 |
| JP | 2016527313 A | 9/2016 |
| WO | WO-9320242 A1 | 10/1993 |
| WO | WO-02072791 A2 | 9/2002 |
| WO | WO-2005059096 A2 | 6/2005 |
| WO | WO-2008054543 A2 | 5/2008 |
| WO | WO-2008063135 A1 | 5/2008 |
| WO | WO-2011109031 A1 | 9/2011 |
| WO | WO-2012078312 A2 | 6/2012 |
| WO | WO-2012154201 A1 | 11/2012 |
| WO | WO-2013036685 A1 * | 3/2013 | .............. C12P 19/34 |
| WO | WO-2014021938 A1 | 2/2014 |

(56)　　　　　References Cited

FOREIGN PATENT DOCUMENTS

| WO | WO-2015021080 A2 | 2/2015 | |
| WO | WO-2016132129 A1 * | 8/2016 | ........... C12Q 1/6844 |
| WO | 2021152147 A1 | 8/2021 | |
| WO | WO-2022010934 A2 | 1/2022 | |
| WO | WO-2022076326 A1 | 4/2022 | |
| WO | WO-2022086866 A1 | 4/2022 | |
| WO | WO-2022087293 A1 | 4/2022 | |
| WO | WO-2022098662 A2 | 5/2022 | |
| WO | WO-2022159620 A1 | 7/2022 | |
| WO | WO-2022178137 A1 | 8/2022 | |
| WO | WO-2022204309 A1 | 9/2022 | |
| WO | WO-2022204316 A2 | 9/2022 | |
| WO | WO-2022217004 A1 | 10/2022 | |

OTHER PUBLICATIONS

BERG: Biochemistry. 5th ED. New York (2002) 148-149.

Blanchard et al.: High-Density Oligonucleotide Arrays. Biosensors & Bioelectronics, 11(6/7):687-690 (1996).

Buermans et al.: Next Generation sequencing technology: Advances and applications, Biochimica et Biophysica Acta (BBA)—Molecular Basis of Disease, 1842:1931-1941 (2014).

Cheng et al.: High throughput parallel synthesis of oligonucleotides with 1536 channel synthesizer. Nucleic Acids Res. 30(18):e93 (2002).

Cleary et al.: Production of complex nucleic acid libraries using highly parallel in situ oligonucleotide synthesis. Nat Methods. 1(3):241-248 (2004).

Cohen et al.: Human population: The next half century. Science. 302:1172-1175 (2003).

Cruse et al.: Atlas of Immunology. Third Edition. Boca Raton:CRC Press (pp. 282-283) (2010).

Elsik et al.: The Genome sequence of taurine cattle: A window of ruminant biology and evolution. Science. 324:522-528 (2009).

Fodor et al.: Light-directed, spatially addressable parallel chemical synthesis. Science. 251(4995):767-773 (1991).

Gao et al.: A method for the generation of combinatorial antibody libraries using pIX phage display. PNAS 99(20):12612-12616 (2002).

GE Healthcare. AKTA oligopilot plus. Data File 18-114-66 ADC. 8 pages (2006).

GE Healthcare. Robust and cost-efficient oligonucleotide synthesis. Application Note 28-4058-08 AA. 4 pages (2005).

Gibson et al.: Creation of a Bacterial Cell Controlled by A Chemically Synthesized Genome. Science. 329(5989):52-56 (2010).

Hudson: Matrix Assisted Synthetic Transformations: A Mosaic of Diverse Contributions. Journal of Combinatorial Chemistry. 1(6):403-457 (1999).

Karlin et al.: Applications and statistics for multiple high-scoring segments in molecular sequences. PNAS USA 90:5873-5877 (1993).

Karlin et al.: Methods for assessing the statistical significance of molecular sequence features by using general scoring schemes. PNAS USA 87:2264-2268 (1990).

Kong et al.: Parallel gene synthesis in a microfluidic device. Nucleic Acids Res. 35(8):e61 (2007).

Kosuri and Church. Large-scale de novo DNA synthesis: technologies and applications. Nature Methods. 11:499-507 (2014) Available at: http://www.nature.com/nmeth/journal/v11/n5/full/nmeth.2918.html.

Kosuri et al.: A scalable gene synthesis by selective amplification of DNA pools from high-fidelity microchips. Nature Biotechnology. 2010; 28:1295-1299.

Kosuri et al.: A scalable gene synthesis platform using high-fidelity DNA microchips Nat.Biotechnol. 28(12):1295-1299 (2010).

Krayden, Inc.: A Guide to Silane Solutions. Silane coupling agents. 7 pages. Published on May 31, 2005 at: http://krayden.com/pdf/xia_silane_chemistry.pdf.

Lausted et al.: POSaM: a fast, flexible, open-source, inkjet oligonucleotide synthesizer and microarrayer. Genome Biology. 5:R58, 17 pages (2004) available at https://www.ncbi.nlm.nih.gov/pmc/articles/PMC507883/.

Lebl et al.: Economical Parallel Oligonucleotide and Peptide Synthesizer—Pet Oligator. Int. J. Peptide Res. Ther. 13(1-2):367-376 (2007).

Leproust et al.: Synthesis of high-quality libraries of long (150mer) oligonucleotides by a novel depurination controlled process. Nucleic Acids Research. 38(8):2522-2540 (2010).

Lewontin and Harti. Population genetics in forensic DNA typing. Science, 254:1745-1750, 1991.

Ma et al.: DNA synthesis, assembly and application in synthetic biology. Current Opinion in Chemical Biology. 16:260-267 (2012).

Ma et al.: Versatile surface functionalization of cyclic olefin copolymer (COC) with sputtered SiO2 thin film for potential BioMEMS applications. Journal of Materials Chemistry. 11 pages (2009).

Mazor et al.: Isolation of Full-Length IgG Antibodies from Combinatorial Libraries Expressed in Escherichia coli; Antony S. Dimitrov (ed.), Therapeutic Antibodies: Methods and Protocols, vol. 525, Chapter 11, pp. 217-239 (2009).

McBride & Caruthers. An investigation of several deoxynucleoside phosphoramidites useful for synthesizing deoxyoligonucleotides. Tetrahedron Lett. 24:245-248 (1983).

Mitra et al.: In situ localized amplification and contact replication of many individual DNA molecules. Nucleic Acids Res. 27(24):e34 (1999).

Morin et al.: Profiling the HeLa S3 transcriptome using randomly primed cDNA and massively parallel short-read sequencing. Biotechniques. 45:81-94 (2008).

Opposition to European Patent No. 3030682 filed Mar. 3, 2021.

PCT/US2014/049834 International Preliminary Report on Patentability dated Feb. 18, 2016.

PCT/US2014/049834 International Search Report and Written Opinion mailed Mar. 19, 2015.

PCT/US2014/049834 Invitation to Pay Additional Fees mailed Jan. 5, 2015.

Pirrung. How to make a DNA chip. Angew. Chem. Int. Ed. 41:1276-1289 (2002).

Pray. Discovery of DNA Structure and Function: Watson and Crick. Nature Education.6 pages (2008) available at: http://www.nature.com/scitable/topicpage/discovery-of-dna-structure-and-function-watson-397.

Quan et al.: Parallel on-chip gene synthesis and application to optimization of protein expression. Nature Biotechnology. 29:449-452 (2011).

Rafalski and Morgante, Corn and humans: recombination and linkage disequilibrium in two genomes of similar size. Trends in Genetics. 20(2):103-111. (2004).

Rogozin et al.: Origin and evolution of spliceosomal introns. Biology Direct, 7:11 (2012).

Saaem et al.: In situ synthesis of DNA microarray on functionalized cyclic olefin copolymer substrate ACS Applied Materials & Interfaces. 2(2):491-497 (2010).

Sargolzaei et al.: Extent of linkage disequilibrium in Holstein cattle in North America. J.Dairy Science. 91:2106-2117 (2007).

Srivannavit et al.: Design and fabrication of microwell array chips for a solution-based, photogenerated acid-catalyzed parallel oligonucleotide DNA synthesis. Sensors and Actuators A. 116:150-160 (2004).

Steel. The Flow-Thru Chip A Three-dimensional biochip platform. In: Schena, Microarray Biochip Technology, Chapter 5, Natick, MA: Eaton Publishing, 2000, 33 pages.

Taylor et al.: Impact of surface chemistry and blocking strategies on DNA microarrays. Nucleic Acids Research, 31(16):e87 19 pages (2003).

Tian et al.: Accurate multiplex gene synthesis from programmable DNA microchips. Nature. 432(7020):1050-1054 (2004).

U.S. Appl. No. 16/737,401 Final Office Action dated Jun. 13, 2022.

U.S. Appl. No. 14/452,429 Notice of Allowance dated Jun. 7, 2016.

U.S. Appl. No. 14/452,429 Office Action mailed Apr. 9, 2015.

U.S. Appl. No. 14/452,429 Office Action mailed Oct. 21, 2015.

U.S. Appl. No. 14/452,429 Restriction Requirement mailed Dec. 12, 2014.

U.S. Appl. No. 14/885,962 Notice of Allowance dated Nov. 8, 2017 and Sep. 29, 2017.

U.S. Appl. No. 14/885,962 Office Action dated Dec. 16, 2016.

(56) References Cited

OTHER PUBLICATIONS

U.S. Appl. No. 14/885,962 Office Action dated Sep. 8, 2016.
U.S. Appl. No. 14/885,962 Restriction Requirement dated Mar. 1, 2016.
U.S. Appl. No. 14/885,963 Notice of Allowance dated May 24, 2016.
U.S. Appl. No. 14/885,963 Office Action dated Feb. 5, 2016.
U.S. Appl. No. 14/885,965 Office Action dated Aug. 28, 2018.
U.S. Appl. No. 14/885,965 Office Action dated Aug. 30, 2017.
U.S. Appl. No. 14/885,965 Office Action dated Feb. 10, 2017.
U.S. Appl. No. 14/885,965 Office Action dated Feb. 18, 2016.
U.S. Appl. No. 14/885,965 Office Action dated Jan. 4, 2018.
U.S. Appl. No. 14/885,965 Office Action dated Jul. 7, 2016.
U.S. Appl. No. 15/187,714 Final Office Action dated Sep. 17, 2019.
U.S. Appl. No. 15/187,714 Office Action dated Apr. 4, 2019.
U.S. Appl. No. 15/187,714 Restriction Requirement dated Sep. 17, 2018.
U.S. Appl. No. 15/187,721 Notice of Allowance dated Dec. 7, 2016.
U.S. Appl. No. 15/187,721 Office Action dated Oct. 14, 2016.
U.S. Appl. No. 15/233,835 Notice of Allowance dated Oct. 4, 2017.
U.S. Appl. No. 15/233,835 Office Action dated Feb. 8, 2017.
U.S. Appl. No. 15/233,835 Office Action dated Jul. 26, 2017.
U.S. Appl. No. 15/233,835 Restriction Requirement dated Nov. 4, 2016.
U.S. Appl. No. 15/245,054 Notice of Allowance dated Dec. 14, 2017.
U.S. Appl. No. 15/245,054 Office Action dated Mar. 21, 2017.
U.S. Appl. No. 15/245,054 Office Action dated Oct. 19, 2016.
U.S. Appl. No. 15/377,547 Final Office Action dated Feb. 8, 2019.
U.S. Appl. No. 15/377,547 Office Action dated Jul. 27, 2018.
U.S. Appl. No. 15/377,547 Office Action dated Mar. 24, 2017.
U.S. Appl. No. 15/377,547 Office Action dated Nov. 30, 2017.
U.S. Appl. No. 15/602,991 Final Office Action dated Dec. 13, 2018.
U.S. Appl. No. 15/602,991 Notice of Allowance dated Oct. 25, 2017.
U.S. Appl. No. 15/602,991 Office Action dated May 31, 2018.
U.S. Appl. No. 15/602,991 Office Action dated May 31, 2019.
U.S. Appl. No. 15/602,991 Office Action dated Sep. 21, 2017.
U.S. Appl. No. 15/603,013 Final Office Action dated Nov. 6, 2019.
U.S. Appl. No. 15/603,013 Office Action dated Jan. 30, 2018.
U.S. Appl. No. 15/603,013 Office Action dated Jul. 10, 2018.
U.S. Appl. No. 15/603,013 Office Action dated Jun. 26, 2019.
U.S. Appl. No. 15/603,013 Office Action dated Oct. 20, 2017.
U.S. Appl. No. 15/729,564 Final Office Action dated Dec. 13, 2018.
U.S. Appl. No. 15/729,564 Office Action dated Jan. 8, 2018.
U.S. Appl. No. 15/729,564 Office Action dated Jun. 6, 2018.
U.S. Appl. No. 15/729,564 Office Action dated May 30, 2019.
U.S. Appl. No. 15/991,992 Office Action dated May 21, 2020.
U.S. Appl. No. 15/991,992 Restriction Requirement dated Mar. 10, 2020.
U.S. Appl. No. 16/039,256 Final Office Action dated Mar. 30, 2021.
U.S. Appl. No. 16/039,256 Office Action dated Aug. 20, 2020.
U.S. Appl. No. 16/039,256 Office Action dated May 10, 2022.
U.S. Appl. No. 16/039,256 Restriction Requirement dated May 18, 2020.
U.S. Appl. No. 16/409,608 Office Action dated Sep. 9, 2019.
U.S. Appl. No. 16/535,777 Final Office Action dated Oct. 20, 2020.
U.S. Appl. No. 16/535,777 Office Action dated Feb. 8, 2021.
U.S. Appl. No. 16/535,777 Office Action dated Jan. 23, 2020.
U.S. Appl. No. 16/535,779 First Action Interview dated Feb. 10, 2020.
U.S. Appl. No. 16/737,401 Office Action dated Jan. 5, 2022.
U.S. Appl. No. 16/737,401 Restriction Requirement dated Nov. 15, 2021.
Van Tassell et al.: SNP discovery and allele frequency estimation by deep sequencing of reduced representation libraries. Nature Methods. 5:247-252 (2008).
Wootton et al. Statistics of local complexity in amino acid sequences and sequence databases. Computers & Chemistry 17(2):149-163 (Jun. 1993).
Xu et al.: Design of 240,000 orthogonal 25mer DNA barcode probes. PNAS. 106(7):2289-2294 (2009).
International Search Report and Written Opinion for International Application No. PCT/US2022/040813, mailed on Jun. 7, 2023, 13 pages.

* cited by examiner

METHODS AND COMPOSITIONS RELATING TO COVALENTLY CLOSED NUCLEIC ACIDS

CROSS REFERENCE

This application claims the benefit of U.S. Provisional Patent Application No. 63/235,069, filed on Aug. 19, 2021, which is incorporated by reference in its entirety.

SEQUENCE LISTING

The instant application contains a Sequence Listing which has been submitted electronically in ASCII format and is hereby incorporated by reference in its entirety. Said ASCII copy, created on Oct. 26, 2022, is named 44854-828_201_SL.xml, and is 21,169 bytes in size.

BRIEF SUMMARY

Described herein are methods for assembly of a covalently closed double stranded nucleic acid, comprising: (a) providing a double stranded nucleic acid; (b) amplifying the double stranded nucleic acid using a primer comprising one or more uracils to generate a double stranded nucleic acid comprising one or more uracils at a 5' end and a 3' end; (c) digesting the double stranded nucleic acid comprising one or more uracils at the 5' end and the 3' end using a glycosylase and a glycosylase-lyase to generate a double stranded nucleic acid comprising a loop structure at the 5' end and the 3' end; and (d) ligating gaps in the double stranded nucleic acid comprising the loop structure at the 5' end and the 3' end using a ligase to generate the covalently closed double stranded nucleic acid. Further provided herein are methods, wherein the double stranded nucleic acid is deoxyribonucleic acid. Further provided herein are methods, wherein the double stranded nucleic acid is linear. Further provided herein are methods, wherein the primer comprises at most about 40 bases. Further provided herein are methods, wherein the primer comprises at most about 25 bases. Further provided herein are methods, wherein the primer comprises a range of about 10 bases to about 25 bases. Further provided herein are methods, wherein the primer comprises a range of about 15 bases to about 35 bases. Further provided herein are methods, wherein the primer comprises at most about 10 uracils. Further provided herein are methods, wherein the primer comprises at most about 5 uracils. Further provided herein are methods, wherein the primer comprises at most about 3 uracils. Further provided herein are methods, wherein the primer comprises about 1 to about 5 uracils. Further provided herein are methods, wherein the primer comprises a sequence according to any one of SEQ ID NOs: 5-8. Further provided herein are methods, wherein the glycosylase comprises base excision activity. Further provided herein are methods, wherein the base excision activity of the glycosylase generates an abasic site. Further provided herein are methods, wherein the glycosylase excises the one or more uracils. Further provided herein are methods, wherein the glycosylase is AlkA, 3-methyladenine DNA glycosylase II, Mag1, MPG, SMUG1, MBD4, NTIHL1, uracil DNA glycosylases, helix-hairpin-helix (HhH) glycosylases, or 3-methyl-purine glycosylase (MPG). Further provided herein are methods, wherein the glycosylase is uracil DNA glycosylase. Further provided herein are methods, wherein the glycosylase-lyase breaks the phosphodiester backbone at a 3' and 5' sides of the abasic site. Further provided herein are methods, wherein the glycosylase-lyase is Endonuclease VIII. Further provided herein are methods, wherein a concentration of the glycosylase and the glycosylase-lyase is in a range of about 0.1 U to about 10 U. Further provided herein are methods, wherein a concentration of the glycosylase and the glycosylase-lyase is in a range of about 1 U to about 5 U. Further provided herein are methods, wherein a concentration of the glycosylase and the glycosylase-lyase is at most about 5 U. Further provided herein are methods, wherein the ligase catalyzes joining of the gaps in the double stranded nucleic acid following step (c). Further provided herein are methods, wherein a concentration of the ligase is in a range of about 50 U to about 500 U. Further provided herein are methods, wherein a concentration of the ligase is in a range of about 5 U to about 100 U. Further provided herein are methods, wherein the loop structure comprises at most about 40 bases. Further provided herein are methods, wherein the loop structure comprises at most about 25 bases. Further provided herein are methods, wherein the loop structure comprises a range of about 15 bases to about 35 bases. Further provided herein are methods, wherein the loop structure comprises a sequence according to any one of SEQ ID NOs: 9-20. Further provided herein are methods, wherein step (c) comprises excision of the one or more uracils. Further provided herein are methods, wherein the method does not require heating between step (c) and step (d). Further provided herein are methods, wherein a product following step (d) is a linear fragment. Further provided herein are methods, wherein a product following step (d) is resistant to exonuclease activity. Further provided herein are methods, wherein the method results in at least about 65% recovery. Further provided herein are methods, wherein the method results in at least about 70% recovery. Further provided herein are methods, wherein the method results in at least about 80% recovery. Further provided herein are methods, wherein the method results in at least about 90% recovery. Further provided herein are methods, wherein the covalently closed double stranded nucleic acid is used as a vector for transcription. Further provided herein are methods, wherein the covalently closed double stranded nucleic acid is used as a vector for gene therapy. Further provided herein are methods, wherein the covalently closed double stranded nucleic acid is used as a vector for delivering a therapeutic agent. Further provided herein are methods, wherein the therapeutic agent comprises an immunotherapy. Further provided herein are methods, wherein the therapeutic agent comprises a RNA interfering agent (RNAi), a small interfering RNA (siRNA), a short hairpin RNA (shRNA), a microRNA (miRNA), or an antisense oligonucleotide.

Described herein are covalently closed double stranded nucleic acids generated by any one of the methods described herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

In FIG. 9A, lane 2 is a ladder, lanes 3-6 are ccDNA samples treated with RecBCD and lane 7 is a ccDNA control untreated with RecBCD. In FIG. 9B, lane 3 is a ladder, lane 4 is linear DNA treated with RecBCD, lane 5 is ccDNA untreated with RecBCD and lanes 6-7 are two ccDNA samples treated with RecBCD.

DETAILED DESCRIPTION

Definitions

Figure 1:
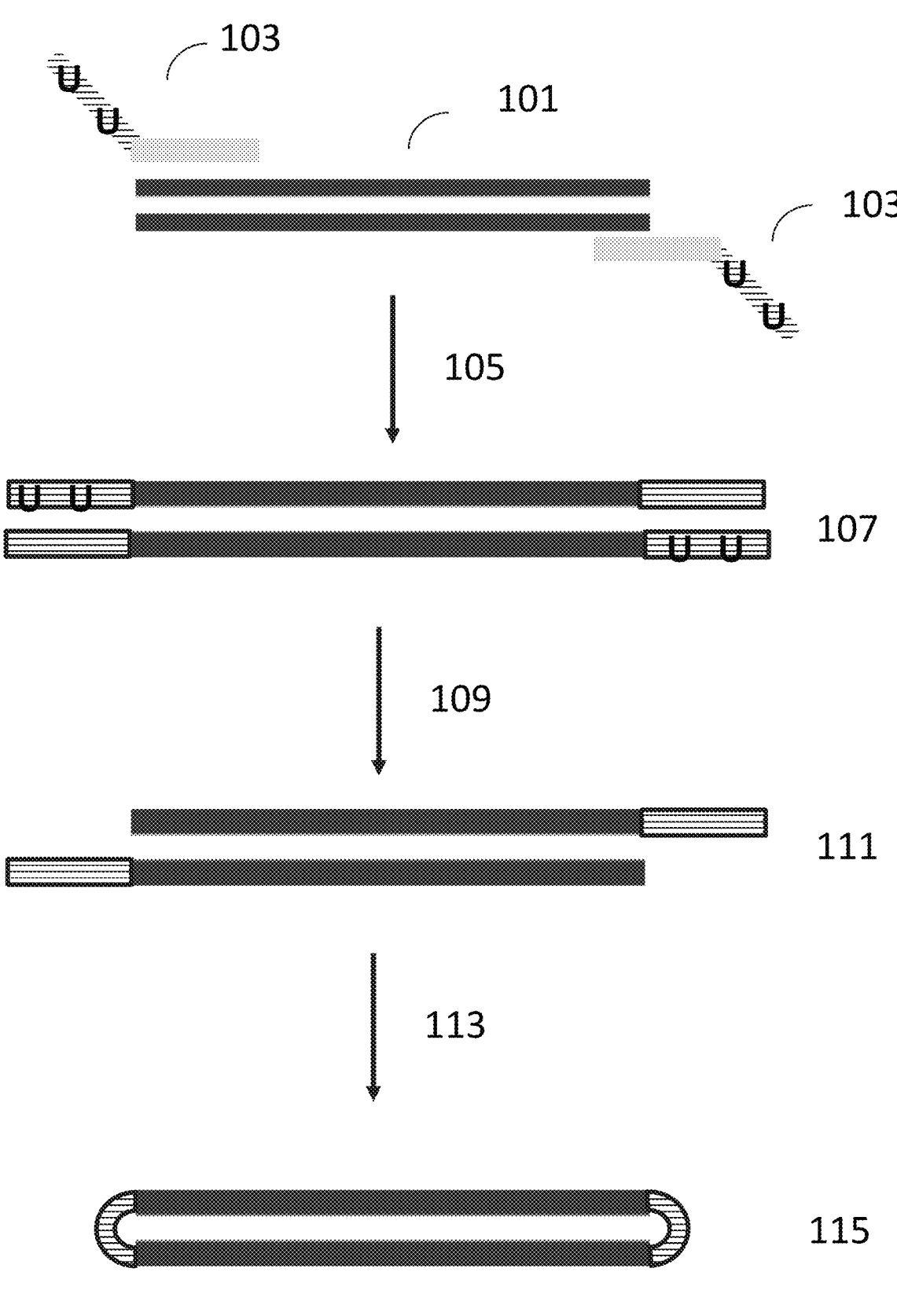
FIG. 1 depicts a schema of the methods described herein.

Throughout this disclosure, various embodiments are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the invention, subject to any specifically excluded limit in the stated range. Where the stated range includes one or both of the limits, ranges excluding either or both of those included limits are also included in the invention, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "nucleic acid" encompasses double- or triple-stranded nucleic acids, as well as single-stranded molecules. In double- or triple-stranded nucleic acids, the nucleic acid strands need not be coextensive (i.e., a double-stranded nucleic acid need not be double-stranded along the entire length of both strands). Nucleic acid sequences, when provided, are listed in the 5' to 3' direction, unless stated otherwise. Methods described herein provide for the generation of isolated nucleic acids. Methods described herein additionally provide for the generation of isolated and purified nucleic acids. A "nucleic acid" as referred to herein can comprise at least 5, 10, 20, 30, 40, 50, 60, 70, 80, 90, 100, 125, 150, 175, 200, 225, 250, 275, 300, 325, 350, 375, 400, 425, 450, 475, 500, 600, 700, 800, 900, 1000, 1100, 1200, 1300, 1400, 1500, 1600, 1700, 1800, 1900, 2000, or more bases in length. Moreover, provided herein are methods for the synthesis of any number of polypeptide-segments encoding nucleotide sequences, including sequences encoding non-ribosomal peptides (NRPs), sequences encoding non-ribosomal peptide-synthetase (NRPS) modules and synthetic variants, polypeptide segments of other modular proteins, such as antibodies, polypeptide segments from other protein families, including non-coding DNA or RNA, such as regulatory sequences e.g. promoters, transcription factors, enhancers, siRNA, shRNA, RNAi, miRNA, small nucleolar RNA derived from microRNA, or any functional or structural DNA or RNA unit of interest. The following are non-limiting examples of polynucleotides; coding or non-coding regions of a gene or gene fragment, intergenic DNA, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), small nucleolar RNA, ribozymes, complementary DNA (cDNA), which is a DNA representation of mRNA, usually obtained by reverse transcription of messenger RNA (mRNA) or by amplification; DNA molecules produced synthetically or by amplification, genomic DNA, recombinant polynucleotides, branched polynucleotides, plasmids, vectors, isolated DNA of any sequence, isolated RNA of any sequence, nucleic acid probes, and primers, cDNA encoding for a gene or gene fragment referred to herein may comprise at least one region encoding for exon sequences without an intervening intron sequence in the genomic equivalent sequence.

Unless specifically stated or obvious from context, as used herein, the term "about" in reference to a number or range of numbers is understood to mean the stated number and numbers+/−10% thereof, or 10% below the lower listed limit and 10% above the higher listed limit for the values listed for a range.

Covalently Closed Nucleic Acids

Vectors such a viral or non-viral vectors are commonly used for both research and development and therapies. For example, vectors are used for gene therapy for delivering therapeutic genes to cells. Current problems with vectors such as viral vectors or plasmid vectors include immuno-genicity or short-duration of expression. Thus, there is a need for generation of vectors that address these current problems.

Described herein are methods and compositions for the assembly of covalently closed nucleic acids (also known as dumbbell nucleic acid, e.g., dbDNA, ccDNA). Covalently closed nucleic acids described herein may be used as vectors. Covalently closed nucleic acids described herein may be used to deliver genes (e.g., therapeutic genes) into cells. Covalently closed nucleic acids described herein provided for improved delivery of genetic material into cells. Method and compositions described herein, in some embodiments, are universal in nature and provide flexibility. In some embodiments, methods and compositions described herein result in generation of covalently closed nucleic acids that are resistant to enzyme (e.g., exonuclease) degradation.

An exemplary process for assembly of covalently closed nucleic acids is seen in FIG. 1. A double stranded nucleic acid 101 is provided. In some embodiments, the double stranded nucleic acid is deoxyribonucleic acid. In some embodiments, the double stranded nucleic acid is linear. The double stranded nucleic acid 101 is amplified using primers 103 comprising one or more uracils. Following amplification 105 using primers 103 comprising one or more uracils, a double stranded nucleic acid is generated comprising one or more uracils at a 5' end and a 3' end 107. In some embodiments, the primer comprises at most about 40 bases. In some embodiments, the primer comprises at most about 25 bases. In some embodiments, the primer comprises a range of about 10 bases to about 25 bases. In some embodi-ments, the primer comprises a range of about 15 bases to about 35 bases. In some embodiments, the primer comprises at most about 10 uracils. In some embodiments, the primer comprises at most about 5 uracils. In some embodiments, the primer comprises at most about 3 uracils. In some embodi-ments, the primer comprises about 1 to about 5 uracils. In some embodiments, the primer comprises a sequence according to any one of SEQ ID NOs: 5-8. The double stranded nucleic acid comprising one or more uracils at a 5' end and a 3' end 107 is then subject to digestion 109 using a glycosylase and a glycosylase-lyase to generate a double stranded nucleic acid comprising a loop structure at the 5' end and the 3' end 111. In some embodiments, the glyco-sylase comprises base excision activity. In some embodi-ments, the base excision activity of the glycosylase gener-ates an abasic site. In some embodiments, the glycosylase excises the one or more uracils. In some embodiments, the glycosylase is AlkA, 3-methyladenine DNA glycosylase II, Mag1, MPG, SMUG1, MBD4, NTHL1, uracil DNA glyco-sylases, helix-hairpin-helix (HhH) glycosylases, or 3-methyl-purine glycosylase (MPG). In some embodiments, the glycosylase is uracil DNA glycosylase. In some embodiments, the glycosylase-lyase breaks the phosphodiester backbone at a 3' and 5' sides of the abasic site. In some embodiments, the glycosylase-lyase is Endonuclease VIII. In some embodiments, a concentration of the glycosylase and the glycosylase-lyase is in a range of about 0.1 U to about 10 U. In some embodiments, a concentration of the glycosylase and the glycosylase-lyase is in a range of about 1 U to about 5 U. In some embodiments, a concentration of the glycosylase and the glycosylase-lyase is at most about 5 U. The double stranded nucleic acid comprising a loop structure at the 5' end and the 3' end 111 is then subject to ligation 113 of the gaps in the double stranded nucleic acid comprising the loop structure at the 5' end and the 3' end using a ligase to generate the covalently closed double stranded nucleic acid 115. In some embodiments, a concen-tration of the ligase is in a range of about 50 U to about 500 U. In some embodiments, a concentration of the ligase is in a range of about 5 U to about 100 U. In some embodiments, the loop structure comprises at most about 40 bases. In some embodiments, the loop structure comprises at most about 25 bases. In some embodiments, the loop structure comprises a range of about 15 bases to about 35 bases. In some embodi-ments, the loop structure comprises a sequence according to any one of SEQ ID NOs: 9-20.

Provided herein, in some embodiments, are methods for assembly of a covalently closed double stranded nucleic acid, comprising: a. providing a double stranded nucleic acid; b. amplifying the double stranded nucleic acid using a primer comprising one or more uracils to generate a double stranded nucleic acid comprising one or more uracils at a 5' end and a 3' end; c. digesting the double stranded nucleic acid comprising one or more uracils at the 5' end and the 3' end using a glycosylase and a glycosylase-lyase to generate a double stranded nucleic acid comprising a loop structure at the 5' end and the 3' end; and d. ligating gaps in the double stranded nucleic acid comprising the loop structure at the 5' end and the 3' end using a ligase to generate the covalently closed double stranded nucleic acid.

Provided herein, in some embodiments, are methods for assembly of a covalently closed double stranded nucleic acid, wherein the method comprises providing a double stranded nucleic acid. In some embodiments, the double stranded nucleic acid is deoxyribonucleic acid. In some embodiments, the double stranded nucleic acid is linear. In some embodiments, the double stranded nucleic acid com-prises at least 50, 75, 100, 125, 150, 175, 200, 250, 500, 800, 1000, 2000, 5000, 8000, 10,000, or at least 20,000 bases in length. In some embodiments, the double stranded nucleic acid comprises a range of about 50 to about 20,000, about 50 to about 10,000, about 50 to about 8000, about 50 to about 5000, about 50 to about 2000, about 50 to about 1000, about 50 to about 800, about 50 to about 500, about 100 to about 20,000, about 100 to about 10,000, about 100 to about 8000, about 100 to about 5000, about 100 to about 2000, about 100 to about 1000, about 100 to about 800, about 100 to about 500, about 500 to about 20,000, about 500 to about 10,000, about 500 to about 8000, about 500 to about 5000, about 500 to about 2000, about 500 to about 1000, about 500 to about 800, about 1000 to about 20,000, about 1000 to about 10,000, about 1000 to about 8000, about 1000 to about 5000, or about 1000 to about 2000 bases.

Provided herein, in some embodiments, are methods for assembly of a covalently closed double stranded nucleic acid, wherein the method comprises amplification using a primer comprising one or more uracils. In some instances, the primers comprise at least or about 5, 6, 7, 8, 9, 10, 11, 12, 13, 14, 15, 16, 17, 18, 19, 20, 21, 22, 23, 24, 25, 26, 27, 28, 29, 30 or more than 30 bases. In some instances, the primers comprise at least or about 10, 15, 20, 25, 30, 35, 40, 45, or more than 45 bases. In some embodiments, the primer comprises at most about 40 bases. In some embodiments, the primer comprises at most about 25 bases. In some embodiments, the primer comprises a range of about 10 bases to about 25 bases. In some embodiments, the primer comprises a range of about 15 bases to about 35 bases.

In some embodiments, the primer comprises 1, 2, 3, 4, 5, 6, 7, 8, 9, 10, 11, 12, 13, 14, 15, or more than 15 uracils. In some embodiments, the primer comprises at most about 10 uracils. In some embodiments, the primer comprises at most about 5 uracils. In some embodiments, the primer comprises at most about 3 uracils. In some embodiments, the primer comprises about 1 to about 5 uracils.

In some embodiments, the primer comprises a sequence according to any one of SEQ ID NOs: 5-8 or reverse complement thereof. In some embodiments, the primer comprises a sequence comprising at least or about 70%, 80%, 85%, 90%, 91%, 92%, 93%, 94%, 95%, 96%, 97%, 98%, 99%, or 100% sequence identity to any one of SEQ ID NOs: 5-8 or reverse complement thereof. In some instances, the primer comprises a sequence comprising at least or about 95% homology to any one of SEQ ID NOs: 5-8 or reverse complement thereof. In some instances, the primer comprises a sequence comprising at least or about 97% homology to any one of SEQ ID NOs: 5-8 or reverse complement thereof. In some instances, the primer comprises a sequence comprising at least or about 99% homology to any one of SEQ ID NOs: 5-8 or reverse complement thereof. In some instances, the primer comprises a sequence comprising at least or about 100% homology to any one of SEQ ID NOs: 5-8 or reverse complement thereof. In some instances, the primer comprises a sequence comprising at least a portion having at least or about 3, 4, 5, 6, 7, 8, 9, 10, 12, 14, 16, 17, 18 or more than 18 nucleotides of any one of SEQ ID NOs: 5-8 or reverse complement thereof.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or 1) occurs in both sequences to yield the number of matched positions, dividing the number of matched positions by the total number of positions in the window of comparison (i.e., the window size), and multiplying the result by 100 to yield the percentage of sequence identity. Typically, techniques for determining sequence identity include comparing two nucleotide or amino acid sequences and the determining their percent identity. Sequence comparisons, such as for the purpose of assessing identities, may be performed by any suitable alignment algorithm, including but not limited to the Needleman-Wunsch algorithm (see, e.g., the EMBOSS Needle aligner available at www.ebi.ac.uk/Tools/psa/emboss_needle/, optionally with default settings), the BLAST algorithm (see, e.g., the BLAST alignment tool available at blast.ncbi.nlm.nih.gov/Blast.cgi, optionally with default settings), and the Smith-Waterman algorithm (see, e.g., the EMBOSS Water aligner available at www.ebi.ac.uk/Tools/psa/emboss_water/, optionally with default settings). Optimal alignment may be assessed using any suitable parameters of a chosen algorithm, including default parameters. The "percent identity", also referred to as "percent homology", between two sequences may be calculated as the number of exact matches between two optimally aligned sequences divided by the length of the reference sequence and multiplied by 100. Percent identity may also be determined, for example, by comparing sequence information using the advanced BLAST computer program, including version 2.2.9, available from the National Institutes of Health. The BLAST program is based on the alignment method of Karlin and Altschul, Proc. Natl. Acad. Sci. USA 87:2264-2268 (1990) and as discussed in Altschul, et al., J. Mol. Biol. 215:403-410 (1990); Karlin and Altschul. Proc. Natl. Acad. Sci. USA 90:5873-5877 (1993); and Altschul et al., Nucleic Acids Res. 25:3389-3402 (1997). Briefly, the BLAST program defines identity as the number of identical aligned symbols (i.e., nucleotides or amino acids), divided by the total number of symbols in the shorter of the two sequences. The program may be used to determine percent identity over the entire length of the sequences being compared. Default parameters are provided to optimize searches with short query sequences, for example, with the blastp program. The program also allows use of an SEG filter to mask-off segments of the query sequences as determined by the SEG program of Wootton and Federhen, Computers and Chemistry 17:149-163 (1993). High sequence identity generally includes ranges of sequence identity of approximately 80% to 100% and integer values there between.

Provided herein, in some embodiments, are methods for assembly of a covalently closed double stranded nucleic acid, wherein the method comprises amplification using a polymerase. In some instances, the polymerase is a DNA polymerase. In some instances, the polymerase is a high fidelity polymerase. A high fidelity polymerase may include polymerases that result in accurate replication or amplification of a template nucleic acid. In some instances, the DNA polymerase is a thermostable DNA polymerase. The DNA polymerase may be from any family of DNA polymerases including, but not limited to, Family A polymerase, Family B polymerase. Family C polymerase, Family D polymerase, Family X polymerase, and Family Y polymerase. In some instances, the DNA polymerase is from a genus including, but not limited to, *Thermus, Bacillus, Thermococcus, Pyrococcus, Aeropyrum, Aqifex, Sulfolobus, Pyrolobus,* or *Methanopyrus.*

Polymerases described herein for use in an amplification reaction may comprise various enzymatic activities. Polymerases are used in the methods of the invention, for example, to extend primers to produce extension products. In some instances, the DNA polymerase comprises 5' to 3' polymerase activity. In some instances, the DNA polymerase comprises 3' to 5' exonuclease activity. In some instances, the DNA polymerase comprises proofreading activity. Exemplary polymerases include, but are not limited to, DNA polymerase (I, II, or III), T4 DNA polymerase, T7 DNA polymerase, Bst DNA polymerase, Bca polymerase, Vent DNA polymerase. Pfu DNA polymerase, and Taq DNA polymerase. Non-limiting examples of thermostable DNA polymerases include, but are not limited to. Taq, Phusion® DNA polymerase, Q5® High Fidelity DNA Polymerase, LongAmp® DNA polymerase, Expand High Fidelity polymerase, HotTub polymerase, Pwo polymerase, Tfl polymerase, Tli polymerase, UITma polymerase, Pfu polymerase, KOD DNA polymerase, JDF-3 DNA polymerase, PGB-D DNA polymerase, Tgo DNA polymerase, Pyrolobus furmarius DNA polymerase, Vent polymerase, and Deep Vent polymerase.

Provided herein, in some embodiments, are methods for assembly of a covalently closed double stranded nucleic acid, wherein the method comprises digestion using a glycosylase and a glycosylase-lyase. In some embodiments, the glycosylase that catalyzes a first step in base excision by removing a base from a nucleic acid while leaving the backbone of the nucleic acid intact, generating an apurinic or apyrimidinic site, or AP site. This removal is accomplished by flipping the base out of a double stranded nucleic acid followed by cleavage of the N-glycosidic bond. In some cases, excision of a base occurs when a glycosylase removes the modified base from a nucleic acid by N-glycosylase activity. The resulting apurinic/apyrimidinic (AP) site is then incised by the AP lyase activity of bifunctional glycosylase via β-elimination of the 3' phosphodiester bond.

The glycosylase and/or a glycosylase-lyase are primarily used at a temperature optimal for enzymatic activity, for example, a temperature of 25-80° C. 25-70° C., 25-60° C., 25-50° C., or 25-40° C. In some cases, reactions involving a glycosylase and/or a glycosylase-lyase occur for at least about 5, 10, 15, 30, 45, 60, 75, 90, 120, 180, or 240 minutes or about 30-150 minutes. In some instances, a glycosylase and/or a glycosylase-lyase is inactivated after use, for example, by an inhibitor or heat.

The concentration of the glycosylase and/or a glycosylase-lyase may vary. In some instances, the concentration of the glycosylase and/or a glycosylase-lyase is in a range of about 0.1 U to about 10 U. An exemplary concentration of the ligase is at most about 5.0 U. In some instances, the concentration of the glycosylase and/or a glycosylase-lyase is about 2.5 U. In some instances, the concentration of the glycosylase and/or a glycosylase-lyase is about 5.0 U. In some instances, the concentration of the glycosylase and/or a glycosylase-lyase is in a range of at least or about 0.25 U to 0.5 U, 0.25 U to 1.0 U, 0.25 U to 1.5 U 0.25 U to 2.0 U, 0.5 U to 1.0 U, 0.5 U to 1.5 U, 0.5 U to 2.0 U, 1.0 U to 1.5 U, 1.0 U to 2.0 U, 1.5 U to 2.0 U, 2.0 U to 4.0 U, 4.0 U to 6.0 U, 4.0 U to 8.0 U, 6.0 U to 10.0 U.

A glycosylase may recognize a uracil or a base pair comprising uracil, for example U:G and/or U:A. Nucleic acid base substrates recognized by a glycosylase include, without limitation, uracil, 3-meA (3-methyladenine), hypoxanthine, 8-oxoG, FapyG, FapyA, Tg (thymine glycol), hoU (hydroxyuracil), hmU (hydroxymethyluracil), fU (formyluracil), hoC (hydroxycytosine), fC (formylcytosine), oxidized base, alkylated base, deaminated base, methylated base, and any modified nucleobase provided herein or known in the art. In some instances, the glycosylase recognizes oxidized bases such as 2,6-diamino-4-hydroxy-5-formamidopyrimidine (FapyG) and 8-oxoguanine (8-oxo). Glycosylases which recognize oxidized bases include, without limitation, OGG1 (8-oxoG DNA glycosylase 1) or E. coli Fpg (recognizes 8-oxoG:C pair), MYH (MutY homolog DNA glycosylase) or E. coli MutY (recognizes 8-oxoG:A), NEIL1, NEIL2 and NEIL3. In some instances, the glycosylase recognizes methylated bases such as 3-methyladenine. An example of a glycosylase that recognizes methylated bases is E. coli AlkA or 3-methyladenine DNA glycosylase II, Mag1 and MPG (methylpurine glycosylase). Additional non-limiting examples of glycosylases include SMUG1 (single-strand specific monofunctional uracil DNA glycosylase 1). TDG (thymine DNA glycosylase), MBD4 (methyl-binding domain glycosylase 4), and NTHL1 (endonuclease III-like 1). Exemplary DNA glycosylases include, without limitation, uracil DNA glycosylases (UDGs), helix-hairpin-helix (HhH) glycosylases, 3-methyl-purine glycosylase (MPG) and endonuclease VIII-like (NEIL) glycosylases. Helix-hairpin-helix (HhH) glycosylases include, without limitation. Nth (homologs of the E. coli EndoIII protein), OggI (8-oxoG DNA glycosylase I), MutY/Mig (A/G-mismatch-specific adenine glycosylase), AlkA (alkyladenine-DNA glycosylase), MpgII (N-methylpurine-DNA glycosylase II), and OggII (8-oxoG DNA glycosylase II). Exemplary 3-methyl-puring glycosylases (MPGs) substances include, in non-limiting examples, alkylated bases including 3-meA, 7-meG, 3-meG and ethylated bases. Endonuclease VIII-like glycosylase substrates include, without limitation, oxidized pyrimidines (e.g., Tg, 5-hC, FaPyA, PaPyG), 5-hU and 8-oxoG.

Exemplary uracil DNA glycosylases (UDGs) include, without limitation, thermophilic uracil DNA glycosylases, uracil-N glycosylases (UNGs), mismatch-specific uracil DNA glycosylases (MUGs) and single-strand specific monofunctional uracil DNA glycosylases (SMUGs). In non-limiting examples, UNGs include UNG1 isoforms and UNG2 isoforms. In non-limiting examples, MUGs include thymidine DNA glycosylase (TDG). A UDG may be active against uracil in ssDNA and dsDNA.

Certain enzymes described herein, such as an endonuclease, and/or exonuclease, glycosylase, recognize a mismatch base-pair that is not an A-T or G-C base pair. One or both the bases in the mismatch base-pair are then removed by the enzyme. For example, the TDG enzyme is capable of excising thymine from G:T mismatches. Endonucleases are often employed to nick DNA in the region of mismatches or damaged DNA, including but not limited to T7 Endonuclease 1, E. coli Endonuclease V, T4 Endonuclease VII, mung bean nuclease. Cel-1 endonuclease. E. coli Endonuclease IV and UVDE. Cel-1 endonuclease from celery and similar enzymes, typically plant enzymes, exhibit properties that detect a variety of errors in double stranded nucleic acids. For example, such enzymes can detect polynucleotide loops and insertions, detect mismatches in base pairing, recognize sequence differences in polynucleotide strands between about 100 bp and 3 kb in length and recognize such mutations in a target polynucleotide sequence without substantial adverse effects of flanking DNA sequences.

In some cases, a base is released from a dsDNA molecule by a DNA glycosylase resulting in an abasic site. This abasic site (AP site) is further processed by an endonuclease which cleaves the phosphate backbone at the abasic site. Endonucleases include AP endonucleases such as class I and class II AP endonucleases, which incise DNA at the phosphate groups 3' and 5' to the baseless site leaving 3' OH and 5' phosphate termini. In some cases, an endonuclease is a class III or class IV AP endonuclease which cleaves DNA at the phosphate groups 3' and 5' to the baseless site to generate 3' phosphate and 5' OH.

AP endonucleases are grouped into families based on sequence similarity and structure, for example, AP endonuclease family 1 or AP endonuclease family 2. Examples of AP endonuclease family 1 members include, without limitation, E. coli exonuclease III, S. pneumoniae and B. subtilis exonuclease A, mammalian AP endonuclease 1 (AP1). Drosophila recombination repair protein 1, Arabidopsis thaliana apurinic endonuclease-redox protein, Dictyostelium DNA-(apurinic or apyrimidinic site) lyase, enzymes comprising one or more domains thereof, and enzymes having at least 75% sequence identity to one or more domains or regions thereof. Examples of AP endonuclease family 2 members include, without limitation, bacterial endonuclease IV, fungal and Caenorhabditis elegans apurinic endonuclease APN1, Dictyostelium endonuclease 4 homolog, Archaeal probable endonuclease 4 homologs, mimivirus putative endonuclease 4, enzymes comprising one or more domains thereof, and enzymes having at least 75% sequence identity to one or more domains or regions thereof. Exemplary, endonucleases include endonucleases derived from both Prokaryotes (e.g., endonuclease IV, RecBCD endonuclease. T7 endonuclease, endonuclease II) and Eukaryotes (e.g., *Neurospora* endonuclease, S1 endonuclease, P1 endonuclease, Mung bean nuclease 1, *Ustilago* nuclease). In some cases, an endonuclease functions as both a glycosylase and an AP-lyase. In some cases, the endonuclease is endonuclease VIII. In some instances, the endonuclease is S1 endonuclease. In some cases, the endonuclease is endonuclease III. In some cases, the endonuclease is endonuclease IV. In some instances, an endonuclease is a protein comprising an endonuclease domain having endonuclease activity that cleaves a phosphodiester bond.

Enzymes for digestion used in the methods described herein may comprise glycosylase activity, lyase activity, endonuclease activity, or any combination thereof. As an example. Fpg (formamidopyrimidine [fapy]-DNA glycosylase), also known as 8-oxoguanine DNA glycosylase, acts both as a N-glycosylase and an AP-lyase. The N-glycosylase activity releases a modified base (e.g., 8-oxoguanine, 8-oxoadenine, fapy-guanine, methy-fapy-guanine, fapy-adenine, aflatoxin $B_1$-fapy-guanine, 5-hydroxy-cytosine, 5-hydroxy-uracil) from dsDNA, generating an abasic site. The lyase activity then cleaves both 3' and 5' to the abasic site thereby removing the abasic site and leaving a 1 base gap or nick. Additional enzymes which comprise more than enzymatic activities include, without limitation, endonuclease III (Nth) protein from *E. coli* (N-glycosylase and AP-lyase) and Tma endonuclease III (N-glycosylase and AP-lyase).

Methods described herein for nucleic acid assembly may comprise a ligation reaction using a ligase. Ligases as described herein may function to join nucleic acid fragments. For example, the ligase functions to join adjacent 3'-hydroxylated and 5'-phosphorylated termini of DNA. Ligases include, but are not limited to, *E. coli* ligase, T4 ligase, mammalian ligases (e.g., DNA ligase I, DNA ligase II, DNA ligase III, DNA ligase IV), thermostable ligases, and fast ligases. In some instances, the ligase is a thermostable ligase. In some instances, the ligase is Ampligase.

The concentration of the ligase may vary. In some instances, the concentration of the ligase is in a range of about 10 U to about 500 U. An exemplary concentration of the ligase is about 400 U. In some instances, the concentration of the ligase is about 200 U. In some instances, the concentration of the ligase is about 50 U. In some instances, the concentration of the ligase is in a range of about 50 U to about 500 U. In some instances, the concentration of the ligase is in a range of about 51 U to about 1001 U.

In some instances, the ligase is used at a temperature optimal for enzymatic activity, for example, a temperature of 25-80° C. 25-70° C., 25-60° C., 25-50° C., or 25-40° C. In some instances, the temperature is about 50° C. In some instances, the temperature is about 55° C. In some instances, the temperature is about 65° C. In some instances, the temperature is at least or about 15° C., 20° C., 25° C. 30° C., 35° C. 40° C., 45° C., 50° C. 55° C., 60° C. 65° C., 70° C., 75° C., 80° C., or more than 80° C.

Provided herein, in some embodiments, are methods for assembly of a covalently closed double stranded nucleic acid, wherein the covalently closed double stranded nucleic acid comprises a loop structure. In some embodiments, the loop structure is at 5' end, 3' end, or both of the covalently closed double stranded nucleic acid. In some embodiments, the loop structure comprises at most about 40 bases. In some embodiments, the loop structure comprises at most about 25 bases. In some embodiments, the loop structure comprises a range of about 15 bases to about 35 bases. In some instances, the loop structure comprises at least or about 5, 6, 7, 8, 9, 10, 11, 12, 13, 14, 15, 16, 17, 18, 19, 20, 21, 22, 23, 24, 25, 26, 27, 28, 29, 30 or more than 30 bases. In some instances, the loop structure comprises at least or about 10, 15, 20, 25, 30, 35, 40, 45, or more than 45 bases.

In some embodiments, the loop structure comprises a sequence according to any one of SEQ ID NOs: 9-20 or reverse complement thereof. In some embodiments, the loop structure comprises a sequence comprising at least or about 70%, 80%, 85%, 90%, 91%, 92%, 93%, 94%, 95%, 96%, 97%, 98%, 99%, or 100% sequence identity to any one of SEQ ID NOs: 9-20 or reverse complement thereof. In some instances, the loop structure comprises a sequence comprising at least or about 95% homology to any one of SEQ ID NOs: 9-20 or reverse complement thereof. In some instances, the loop structure comprises a sequence comprising at least or about 97% homology to any one of SEQ ID Nos: 9-20 or reverse complement thereof. In some instances, the loop structure comprises a sequence comprising at least or about 99% homology to any one of SEQ ID NOs: 9-20 or reverse complement thereof. In some instances, the loop structure comprises a sequence comprising at least or about 100% homology to any one of SEQ ID NOs: 9-20 or reverse complement thereof. In some instances, the loop structure comprises a sequence comprising at least a portion having at least or about 3, 4, 5, 6, 7, 8, 9, 10, 12, 14, 16, 17, 18 or more than 18 nucleotides of any one of SEQ ID NOs: 9-20 or reverse complement thereof.

Methods as described herein, in some embodiments, further do not comprise a heating step following digestion. Methods as described herein, in some embodiments, further do not require additional enzymes (e.g., nickase or proteotelomerase) besides a polymerase, glycosylase, glycosylase-lyase, and a ligase Provided herein, in some embodiments, are methods for assembly of a covalently closed double stranded nucleic acid with improved features. Methods as described herein, in certain embodiments, result in generation of a linear product. In some embodiments, the closed double stranded nucleic acid is resistant to exonuclease activity.

In some embodiments, the methods described herein result in a high percentage of recovery of the covalently closed double stranded nucleic acid. In some embodiments, the method results in at least about 65% recovery. In some embodiments, the method results in at least about 70% recovery. In some embodiments, the method results in at least about 80% recovery. In some embodiments, the method results in at least about 90% recovery.

Methods as described herein for assembly of a covalently closed double stranded nucleic acid may comprise multiplexed assembly. In some instances, multiple sequences are assembled in a single reaction. In some instances, at least or about 2, 3, 4, 5, 6, 7, 8, 9, 10, 15, 20, 25, 30, 35, 40, 45, 50, 60, 70, 80, 90, 100, 200, or more than 200 sequences are assembled in a single reaction.

Methods described herein comprising assembly of a covalently closed double stranded nucleic acid result in a high percentage of correct assembly. In some instances, the percentage of correct assembly is at least or about 60%, 65%, 70%, 75%, 80%, 85%, 90%, 95%, 97%, 99%, or more than 99%. In some instances, the percentage of average correct assembly is at least or about 60%, 65%, 70%, 75%, 80%, 85%, 90%, 95%, 97%, 99%, or more than 99%. In some instances, the percentage of correct assembly is 100%.

Methods as described herein comprising e assembly of a covalently closed double stranded nucleic acid result in a low percentage of misassembly. In some instances, the percentage misassembly rate is at most 5%, 10%, 15%, 20%, 25%, 30%, 35%, 40%, 45%, 50%, 55%, or 60%. In some instances, the percentage misassembly rate is about 1% to about 25%, about 5% to about 20%, or about 10% to about 15%. In some instances, the average misassembly rate is at most 5%, 10%, 15%, 20%, 25%, 30%, 35%, 40%, 45%, 50%, 55%, or 60%. In some instances, the average misassembly rate is about 1% to about 25%, about 5% to about 20%, or about 10% to about 15%.

Methods described herein comprising assembly of a covalently closed double stranded nucleic acid result in increased efficiency.

The resulting nucleic acids can be verified. In some cases, the nucleic acids are verified by sequencing. In some instances, the nucleic acids are verified by high-throughput sequencing such as by next generation sequencing. Sequencing of the sequencing library can be performed with any appropriate sequencing technology, including but not limited to single-molecule real-time (SMRT) sequencing. Polony sequencing, sequencing by ligation, reversible terminator sequencing, proton detection sequencing, ion semiconductor sequencing, nanopore sequencing, electronic sequencing, pyrosequencing. Maxam-Gilbert sequencing, chain termination (e.g., Sanger) sequencing, +S sequencing, or sequencing by synthesis.

Methods as described herein, in some embodiments, result in generation of libraries comprising a plurality of covalently closed double stranded nucleic acids. Methods as described herein, in some embodiments, result in generation of libraries comprising covalently closed double stranded nucleic acids comprising at least or about $10^1, 10^2, 10^3, 10^4, 10^5, 10^6, 10^7, 10^8, 10^9, 10^{10}$, or more than $10^{10}$ variants. In some instances, sequences for each variant of the libraries comprising at least or about $10^1, 10^2, 10^3, 10^4, 10^5, 10^6, 10^7, 10^8, 10^9$, or $10^{10}$ variants are known. In some instances, the libraries comprise a predicted diversity of variants. In some instances, the diversity represented in the libraries is at least or about 60%, 65%, 70%, 75%, 80%, 85%, 90%, 95%, or more than 95% of the predicted diversity. In some instances, the diversity represented in the libraries is at least or about 70% of the predicted diversity. In some instances, the diversity represented in the libraries is at least or about 80% of the predicted diversity. In some instances, the diversity represented in the libraries is at least or about 90% of the predicted diversity. In some instances, the diversity represented in the libraries is at least or about 99% of the predicted diversity. As described herein the term "predicted diversity" refers to a total theoretical diversity in a population comprising all possible variants.

Nucleic acid assembly using methods as described herein may efficiently assemble fragments despite high GC content, direct repeats, or secondary structures. In some instances, the fragments for assembly comprise CC content of at least or about 5%, 10%, 15%, 20%, 25%, 30%, 35%, 40%, 45%, 50%, 60%, 65%, 70%, 75%, 80%, 85%, 90%, 95%, or more than 95%, In some instances, the fragments for assembly comprise at least or about 10, 15, 20, 25, 30, 35, 40, 45, 50, 55, 60, 65, 70, 75, or 80 base pairs (bp) adjacent direct repeats. In some instances, the fragments for assembly comprise secondary structures such as hairpin structures with dG values of at least or about −5, −6, −7, −8, −9, −10, −11, −12, −13, −14, −15, −16, −17, −18, −19, −20, −21, −22, −23, −24, −25, or −26 dG. In some instances, the fragments for assembly comprise secondary structures such as hairpin structures with dG values in a range of about −11 to about −18 dG.

Provided herein are methods for assembly of highly uniform libraries of covalently closed double stranded nucleic acids. In some cases, more than about 80% of synthesized covalently closed double stranded nucleic acids are represented within 5× of the mean for nucleic acid representation for a nucleic acid library. In some cases, more than about 90% of synthesized covalently closed double stranded nucleic acids are represented within 5× of the mean for nucleic acid representation for a nucleic acid library. In some cases, more than about 90% of synthesized covalently closed double stranded nucleic acids are represented within 2× of the mean for nucleic acid representation for the library. In some cases, more than about 90% of synthesized covalently closed double stranded nucleic acids are represented within 1.5× of the mean for nucleic acid representation for the library. In some cases, more than about 80% of synthesized covalently closed double stranded nucleic acids are represented within 1.5× of the mean for nucleic acid representation for the library.

Nucleic acid libraries assembled by methods described herein comprise a high percentage of correct sequences compared to predetermined sequences. In some instances, nucleic acids libraries disclosed herein have greater than 70% correct sequence compared to predetermined sequences for nucleic acids. In some instances, nucleic acids libraries disclosed herein have greater than 75% correct sequence compared to predetermined sequences for the nucleic acids. In some instances, nucleic acids libraries disclosed herein have greater than 80% correct sequence compared to predetermined sequences for the nucleic acids. In some instances, nucleic acids libraries disclosed herein have greater than 85% correct sequence compared to predetermined sequences for the nucleic acids. In some instances, nucleic acids libraries disclosed herein have greater than 90% correct sequence compared to predetermined sequences for the nucleic acids. In some instances, nucleic acids libraries disclosed herein have greater than 95% correct sequence compared to predetermined sequences for the nucleic acids. In some instances, nucleic acids libraries disclosed herein have greater than 100% correct sequence compared to predetermined sequences for the nucleic acids.

In some instances, nucleic acids libraries disclosed herein have greater than 70% correct sequence compared to predetermined sequences for the nucleic acids following an amplification reaction. In some instances, nucleic acids libraries disclosed herein have greater than 75% correct sequence compared to predetermined sequences for the nucleic acids following an amplification reaction. In some instances, nucleic acids libraries disclosed herein have greater than 80% correct sequence compared to predetermined sequences for the nucleic acids following an amplification reaction. In some instances, nucleic acids libraries disclosed herein have greater than 85% correct sequence compared to predetermined sequences for the nucleic acids following an amplification reaction. In some instances, nucleic acids libraries disclosed herein have greater than 90% correct sequence compared to predetermined sequences for the nucleic acids following an amplification reaction. In some instances, nucleic acids libraries disclosed herein have greater than 95% correct sequence compared to predetermined sequences for the nucleic acids following an amplification reaction. In some instances, nucleic acids libraries disclosed herein have 100% correct sequence compared to predetermined sequences for the nucleic acids following an amplification reaction.

Provided herein are nucleic acid libraries having high uniformity following amplification. In some instances, more than 80% of nucleic acids are represented within at least about 1.5× the mean representation for the entire library following amplification. In some instances, more than 90% of nucleic acids described herein are represented within at least about 1.5× the mean representation for the entire library following amplification. In some instances, more than 80% of nucleic acids are represented within at least about 2× the mean representation for the entire library following amplification. In some instances, more than 80% of nucleic acids are represented within at least about 2× the mean representation for the entire library following amplification.

Nucleic acid assembly using methods as described herein may result in libraries of nucleic acids comprising low error rate, low dropout rate, low runaway, low percentage of chimeric genes, or a combination thereof. In some instances, libraries of nucleic acids assembled using methods described herein comprise base insertion, deletion, substitution, or total error rates that are under 1/300, 1/400, 1/500, 1/600, 1/700, 1/800, 1/900, 1/1000, 1/1250, 1/1500, 1/2000, 1/2500, 1/3000, 1/4000, 1/5000, 1/6000, 1/7000, 1/8000, 1/9000, 1/10000, 1/12000, 1/15000, 1/20000, 1/25000, 1/30000, 1/40000, 1/50000, 1/60000, 1/70000, 1/80000, 1/90000, 1/100000, 1/125000, 1/150000, 1/200000, 1/300000, 1/400000, 1/500000, 1/600000, 1/700000, 1/800000, 1/900000, 1/1000000, or less, across the library, or across more than 80%, 85%, 90%, 93%, 95%, 96%, 97%, 98%, 99%, 99.5%, 99.8%, 99.9%, 99.95%, 99.98%, 99.99%, or more of the library. In some instances, libraries of nucleic acids assembled using methods described herein result in less than 1.0%, 1.5%, 2.0%, 2.5%, 3.0%, 3.5%, 4.0%, 4.5%, 5.0%, 6.0%, 6.5%, 7.0%, 7.5%, 8.0%, 8.5%, 9.0%, 9.5%, or 10% AT dropout. In some instances, libraries of nucleic acids assembled using methods described herein result in less than 1.0%, 1.5%, 2.0%, 2.5%, 3.0%, 3.5%, 4.0%, 4.5%, or 5.0% AT dropout. In some instances, libraries of nucleic acids assembled using methods described herein result in less than 1.0%, 1.5%, 2.0%, 2.5%, 3.0%, 3.5%, 4.0%, 4.5%, 5.0%, 6.0%, 6.5%, 7.0%, 7.5%, 8.0%, 8.5%, 9.0%, 9.5%, or 10% GC dropout. In some instances, libraries of nucleic acids assembled using methods described herein result in less than 1.0%, 1.5%, 2.0%, 2.5%, 3.0%, 3.5%, 4.0%, 4.5%, or 5.0% GC dropout. In some instances, libraries of nucleic acids assembled using methods described herein comprise at most 1.0%, 1.5%, 2.0%, 2.5%, 3.0%, 3.5%, 4.0%, 4.5%, 5.0%, 6.0%, 6.5%, 7.0%, 7.5%, 8.0%, 8.5%, 9.0%, 9.5%, or 10% of chimeric genes.

Methods of Use

Described herein are methods and compositions for assembly of covalently closed double stranded nucleic acids for various subsequent uses.

In some embodiments, the covalently closed double stranded nucleic acid is used as a template for transcription (e.g., in vitro). In some embodiments, the covalently closed double stranded nucleic acid is used as a template for translation (e.g., in vitro).).

In some embodiments, the covalently closed double stranded nucleic acid is used as a template for in vitro display and selection screen. For example, the covalently closed double stranded nucleic acid is used to express a reporter gene. Exemplary reporter genes include, but are not limited to, acetohydroxyacid synthase (AHAS), alkaline phosphatase (AP), beta galactosidase (LacZ), beta glucuronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), luciferase, and derivatives thereof.

In some embodiments, the covalently closed double stranded nucleic acid is used as a vector for transcription. In some embodiments, the covalently closed double stranded nucleic acid is used as a vector for delivering nucleic acids (e.g., DNA, RNA, small hairpin RNA, micro RNA, siRNA) into a host cell. In some instances, the host cell is a mammalian host cell, an insect host cell, or a plant cell.

Exemplary mammalian host cells include, but are not limited to, 293A cell line, 293FT cell line, 293F cells, 293 H cells, CHO DG44 cells, CHO—S cells, CHO-K1 cells, FUT8 KO CHOK1, Expi293F™ cells, Flp-In™ T-REx™ 293 cell line, Flp-In™-293 cell line, Flp-In™-3T3 cell line, Flp-In™-BHK cell line, Flp-In™-CHO cell line, Flp-In™-CV-1 cell line, Flp-In™-Jurkat cell line, FreeStyle™ 293-F cells, FreeStyle™ CHO—S cells, GripTite™ 293 MSR cell line, GS-CHO cell line, HepaRG™ cells, T-REx™ Jurkat cell line, Per.C6 cells, T-REx™-293 cell line, T-REx™-CHO cell line, and T-REx™-HeLa cell line.

In some instances, a mammalian host cell is a stable cell line, or a cell line that has incorporated a genetic material of interest into its own genome and has the capability to express the product of the genetic material after many generations of cell division. In some cases, a mammalian host cell is a transient cell line, or a cell line that has not incorporated a genetic material of interest into its own genome and does not have the capability to express the product of the genetic material after many generations of cell division.

Exemplary insect host cells include, but are not limited to, *Drosophila* S2 cells, Sf9 cells, Sf21 cells, High Five™ cells, and expresSF+® cells.

In some instances, plant cells include a cell from algae. Exemplary insect cell lines include, but are not limited to, strains from *Chlamydomonas reinhardtii* 137c, or *Synechococcus elongatus* PPC 7942.

In some embodiments, the covalently closed double stranded nucleic acid is used as a vector for gene therapy.

In some embodiments, the covalently closed double stranded nucleic acid is used as a vector for delivering a therapeutic agent. In some embodiments, the therapeutic agent comprises an immunotherapy. In some embodiments, the therapeutic agent comprises a RNA interfering agent (RNAi), a small interfering RNA (siRNA), a short hairpin RNA (shRNA), a microRNA (miRNA), or an antisense oligonucleotide.

In some embodiments, the covalently closed double stranded nucleic acid is used as a vector to deliver a nucleic acid editing system. An exemplary system for nucleic acid editing comprises Clustered Regularly Interspaced Short Palindromic Repeats (CRISPR) and a CRISPR-associated (Cas) protein. When expressed or transferred into cells alongside a guide RNA (gRNA), a Cas protein allows for the targeted introduction or deletion of genetic information via a complex with CRISPR sequence of mRNA. Generally, the gRNA comprises a target sequence region, a protospacer-adjacent motif (PAM) region, and a hairpin region. In a CRISPR/Cas process, a gRNA shepherds the Cas enzyme to a specific stretch of nucleic acid. In some embodiments, the gRNA is a single stranded guide RNA (sgRNA). In some embodiments, the gRNA is a dual stranded guide RNA (dgRNA). Cas then cleaves the nucleic acid to disable or repair a gene. In some embodiments, the nucleic acid is DNA. In some embodiments, the nucleic acid is RNA.

In some embodiments, a nuclease for use in the CRISPR/Cas system is from a species of, but not limited to, *Strep-*

*tococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacter, Carnobacteriun, Rhodobacter, Lisieria, Paludibacler, Clostridium, Lachnospiraceae, Clostridiaridium, Leptotrichia, Francisella, Legionella, Alicyclobacillus, Methanomethyophilus, Porphyromonas, Prevotella, Bacteroidetes, Helcococcus, Leospira, Desulfovibrio, Desulfonatronum, Desulfurococcus, Opitutaceae, Tuberibacillus, Bacillus, Brevibacilus, Methylobacterium, Natronobacterium, Favobacterium, Saccharomyces, Chlamydomonas, Thermus, Pyrococcus, Mycoplasma,* or *Acidaminococcus.*

Exemplary Cas proteins include, but are not limited to, Cpf1, C2c1, C2c2, Cas1, Cas1B, Cas2, Cas3, Cas4, Cas5, Cas6, Cas7, Cas8, Cas9 (Csn1 or Csx12), Cas10, Cas13, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, and modified versions thereof. In some embodiments, the Cas protein targets DNA. In some embodiments, the Cas protein targets RNA. In some embodiments, the Cas protein is Cas9. In some embodiments, the Cas protein is Cas13. Cas proteins include, but are not limited to, wild-type Cas and derivatives, chimeras, or mutants thereof.

In some embodiments, the covalently closed double stranded nucleic acid is used for next generation sequencing (NGS). In some embodiments, the covalently closed double stranded nucleic acid is used during NGS library preparation. For example, the covalently closed double stranded nucleic acid is used for enrichment of barcoded sequences during NGS library preparation. In some embodiments, the covalently closed double stranded nucleic acid is used for circularizing a molecule in preparation for sequencing such as by Single Molecule, Real-Time (SMRT) sequencing.

In some embodiments, the covalently closed double stranded nucleic acid is used for improving analysis of complex populations of sequences. For example, covalently closed double stranded nucleic acid is used for analysis of heterogeneous populations of nucleic acids such as non-protein-coding RNAs (e.g., miRNAs, siRNAs, and piRNAs) that can be difficult to analyze. In some embodiments, the covalently closed double stranded nucleic acid is used for enrichment of sequences that are difficult to analyze.

Polynucleotide Synthesis

Methods of the current disclosure for polynucleotide synthesis may include processes involving phosphoramidite chemistry. In some instances, polynucleotide synthesis comprises coupling a base with phosphoramidite. Polynucleotide synthesis may comprise coupling a base by deposition of phosphoramidite under coupling conditions, wherein the same base is optionally deposited with phosphoramidite more than once, i.e., double coupling. Polynucleotide synthesis may comprise capping of unreacted sites. In some instances, capping is optional. Polynucleotide synthesis may also comprise oxidation or an oxidation step or oxidation steps. Polynucleotide synthesis may comprise deblocking, detritylation, and sulfurization. In some instances, polynucleotide synthesis comprises either oxidation or sulfurization. In some instances, between one or each step during a polynucleotide synthesis reaction, the device is washed, for example, using tetrazole or acetonitrile. Time frames for any one step in a phosphoramidite synthesis method may be less than about 2 min, 1 min, 50 sec, 40 sec, 30 sec, 20 sec and 10 sec.

Polynucleotide synthesis using a phosphoramidite method may comprise a subsequent addition of a phosphoramidite building block (e.g., nucleoside phosphoramidite) to a growing polynucleotide chain for the formation of a phosphite triester linkage. Phosphoramidite polynucleotide synthesis proceeds in the 3' to 5' direction. Phosphoramidite polynucleotide synthesis allows for the controlled addition of one nucleotide to a growing nucleic acid chain per synthesis cycle. In some instances, each synthesis cycle comprises a coupling step. Phosphoramidite coupling involves the formation of a phosphite triester linkage between an activated nucleoside phosphoramidite and a nucleoside bound to the substrate, for example, via a linker. In some instances, the nucleoside phosphoramidite is provided to the device activated. In some instances, the nucleoside phosphoramidite is provided to the device with an activator. In some instances, nucleoside phosphoramidites are provided to the device in a 1.5, 2, 3, 4, 5, 6, 7, 8, 9, 10, 11, 12, 13, 14, 15, 16, 17, 18, 19, 20, 25, 30, 35, 40, 50, 60, 70, 80, 90, 100-fold excess or more over the substrate-bound nucleosides. In some instances, the addition of nucleoside phosphoramidite is performed in an anhydrous environment, for example, in anhydrous acetonitrile. Following addition of a nucleoside phosphoramidite, the device is optionally washed. In some instances, the coupling step is repeated one or more additional times, optionally with a wash step between nucleoside phosphoramidite additions to the substrate. In some instances, a polynucleotide synthesis method used herein comprises 1, 2, 3 or more sequential coupling steps. Prior to coupling, in many cases, the nucleoside bound to the device is de-protected by removal of a protecting group, where the protecting group functions to prevent polymerization. A common protecting group is 4,4'-dimethoxytrityl (DMT).

Following coupling, phosphoramidite polynucleotide synthesis methods optionally comprise a capping step. In a capping step, the growing polynucleotide is treated with a capping agent. A capping step is useful to block unreacted substrate-bound 5'-OH groups after coupling from further chain elongation, preventing the formation of polynucleotides with internal base deletions. Further, phosphoramidites activated with 1H-tetrazole may react, to a small extent, with the O6 position of guanosine. Without being bound by theory, upon oxidation with $I_2$/water, this side product, possibly via O6-N7 migration, may undergo depurination. The apurinic sites may end up being cleaved in the course of the final deprotection of the polynucleotide thus reducing the yield of the full-length product. The O6 modifications may be removed by treatment with the capping reagent prior to oxidation with W/water. In some instances, inclusion of a capping step during polynucleotide synthesis decreases the error rate as compared to synthesis without capping. As an example, the capping step comprises treating the substrate-bound polynucleotide with a mixture of acetic anhydride and I-methylimidazole. Following a capping step, the device is optionally washed.

In some instances, following addition of a nucleoside phosphoramidite, and optionally after capping and one or more wash steps, the device bound growing nucleic acid is oxidized. The oxidation step comprises the phosphite triester is oxidized into a tetracoordinated phosphate triester, a protected precursor of the naturally occurring phosphate diester internucleoside linkage. In some instances, oxidation of the growing polynucleotide is achieved by treatment with iodine and water, optionally in the presence of a weak base (e.g., pyridine, lutidine, collidine). Oxidation may be carried out under anhydrous conditions using, e.g. tert-Butyl hydroperoxide or (1S)-(+)-(10-camphorsulfonyl)-oxaziridine (CSO). In some methods, a capping step is performed following oxidation. A second capping step allows for device drying, as residual water from oxidation that may persist can inhibit subsequent coupling. Following oxidation, the device and growing polynucleotide is optionally washed. In some instances, the step of oxidation is substituted with a sulfurization step to obtain polynucleotide phosphorothioates, wherein any capping steps can be performed after the sulfurization. Many reagents are capable of the efficient sulfur transfer, including but not limited to 3-(Dimethylaminomethylidene)amino)-3H-1,2,4-dithiazole-3-thione, DDTT, 3H-1,2-benzodithiol-3-one 1,1-dioxide, also known as Beaucage reagent, and N,N,N'N'-Tetraethylthiuram disulfide (TETD).

In order for a subsequent cycle of nucleoside incorporation to occur through coupling, the protected 5' end of the device bound growing polynucleotide is removed so that the primary hydroxyl group is reactive with a next nucleoside phosphoramidite. In some instances, the protecting group is DMT and deblocking occurs with trichloroacetic acid in dichloromethane. Conducting detritylation for an extended time or with stronger than recommended solutions of acids may lead to increased depurination of solid support-bound polynucleotide and thus reduces the yield of the desired full-length product. Methods and compositions of the disclosure described herein provide for controlled deblocking conditions limiting undesired depurination reactions. In some instances, the device bound polynucleotide is washed after deblocking. In some instances, efficient washing after deblocking contributes to synthesized polynucleotides having a low error rate.

Methods for the synthesis of polynucleotides typically involve an iterating sequence of the following steps: application of a protected monomer to an actively functionalized surface (e.g., locus) to link with either the activated surface, a linker or with a previously deprotected monomer; deprotection of the applied monomer so that it is reactive with a subsequently applied protected monomer; and application of another protected monomer for linking. One or more intermediate steps include oxidation or sulfurization. In some instances, one or more wash steps precede or follow one or all of the steps.

Methods for phosphoramidite-based polynucleotide synthesis comprise a series of chemical steps. In some instances, one or more steps of a synthesis method involve reagent cycling, where one or more steps of the method comprise application to the device of a reagent useful for the step. For example, reagents are cycled by a series of liquid deposition and vacuum drying steps. For substrates comprising three-dimensional features such as wells, microwells, channels and the like, reagents are optionally passed through one or more regions of the device via the wells and/or channels.

Methods and systems described herein relate to polynucleotide synthesis devices for the synthesis of polynucleotides. The synthesis may be in parallel. For example, at least or about at least 2, 3, 4, 5, 6, 7, 8, 9, 10, 11, 12, 13, 14, 15, 16, 17, 18, 19, 20, 21, 22, 23, 24, 25, 30, 35, 40, 45, 50, 100, 150, 200,250, 300, 350, 400, 450, 500, 550, 600,650, 700, 750, 800, 850, 900, 1000, 10000, 50000, 75000, 100000 or more polynucleotides can be synthesized in parallel. The total number polynucleotides that may be synthesized in parallel may be from 2-100000, 3-50000, 4-10000, 5-1000, 6-900, 7-850, 8-800, 9-750, 10-700, 11-650, 12-600, 13-550, 14-500, 15-450, 16-400, 17-350, 18-300, 19-250, 20-200, 21-150, 22-100, 23-50, 24-45, 25-40, 30-35. Those of skill in the art appreciate that the total number of polynucleotides synthesized in parallel may fall within any range bound by any of these values, for example 25-100. The total number of polynucleotides synthesized in parallel may fall within any range defined by any of the values serving as endpoints of the range. Total molar mass of polynucleotides synthesized within the device or the molar mass of each of the polynucleotides may be at least or at least about 10, 20, 30, 40, 50, 100, 250, 500, 750, 1000, 2000, 3000, 4000, 5000, 6000, 7000, 8000, 9000, 10000, 25000, 50000, 75000, 100000 picomoles, or more. The length of each of the polynucleotides or average length of the polynucleotides within the device may be at least or about at least 10, 15, 20, 25, 30, 35, 40, 45, 50, 100, 150, 200, 300, 400, 500 nucleotides, or more. The length of each of the polynucleotides or average length of the polynucleotides within the device may be at most or about at most 500, 400, 300, 200, 150, 100, 50, 45, 35, 30, 25, 20, 19, 18, 17, 16, 15, 14, 13, 12, 11, 10 nucleotides, or less. The length of each of the polynucleotides or average length of the polynucleotides within the device may fall from 10-500, 9-400, 11-300, 12-200, 13-150, 14-100, 15-50, 16-45, 17-40, 18-35, 19-25. Those of skill in the art appreciate that the length of each of the polynucleotides or average length of the polynucleotides within the device may fall within any range bound by any of these values, for example 100-300. The length of each of the polynucleotides or average length of the polynucleotides within the device may fall within any range defined by any of the values serving as endpoints of the range.

Methods for polynucleotide synthesis on a surface provided herein allow for synthesis at a fast rate. As an example, at least 3, 4, 5, 6, 7, 8, 9, 10, 11, 12, 1314, 15, 16, 17, 18, 19, 20, 21, 22, 23, 24, 25, 26, 27, 28, 29, 30, 35, 40, 45, 50, 55, 60, 70, 80, 90, 100, 125, 150, 175, 200 nucleotides per hour, or more are synthesized. Nucleotides include adenine, guanine, thymine, cytosine, uridine building blocks, or analogs/modified versions thereof. In some instances, libraries of polynucleotides are synthesized in parallel on substrate. For example, a device comprising about or at least about 100; 1,000; 10,000; 30,000; 75,000; 100,000; 1,000,000; 2,000,000; 3,000,000; 4,000,000; or 5,000,000 resolved loci is able to support the synthesis of at least the same number of distinct polynucleotides, wherein polynucleotide encoding a distinct sequence is synthesized on a resolved locus. In some instances, a library of polynucleotides is synthesized on a device with low error rates described herein in less than about three months, two months, one month, three weeks, 15, 14, 13, 12, 11, 10, 9, 8, 7, 6, 5, 4, 3, 2 days, 24 hours or less. In some instances, larger nucleic acids assembled from a polynucleotide library synthesized with low error rate using the substrates and methods described herein are prepared in less than about three months, two months, one month, three weeks, 15, 14, 13, 12, 11, 10, 9, 8, 7, 6, 5, 4, 3, 2 days, 24 hours or less.

In some instances, methods described herein provide for generation of a library of nucleic acids comprising variant nucleic acids differing at a plurality of codon sites. In some instances, a nucleic acid may have 1 site, 2 sites, 3 sites, 4 sites, 5 sites, 6 sites, 7 sites, 8 sites, 9 sites, 10 sites, 11 sites, 12 sites, 13 sites, 14 sites, 15 sites, 16 sites, 17 sites 18 sites, 19 sites, 20 sites, 30 sites, 40 sites, 50 sites, or more of variant codon sites.

In some instances, the one or more sites of variant codon sites may be adjacent. In some instances, the one or more sites of variant codon sites may not be adjacent and separated by 1, 2, 3, 4, 5, 6, 7, 8, 9, 10, or more codons.

In some instances, a nucleic acid may comprise multiple sites of variant codon sites, wherein all the variant codon sites are adjacent to one another, forming a stretch of variant codon sites. In some instances, a nucleic acid may comprise multiple sites of variant codon sites, wherein none the variant codon sites are adjacent to one another. In some instances, a nucleic acid may comprise multiple sites of variant codon sites, wherein some the variant codon sites are adjacent to one another, forming a stretch of variant codon sites, and some of the variant codon sites are not adjacent to one another.

Figure 2:
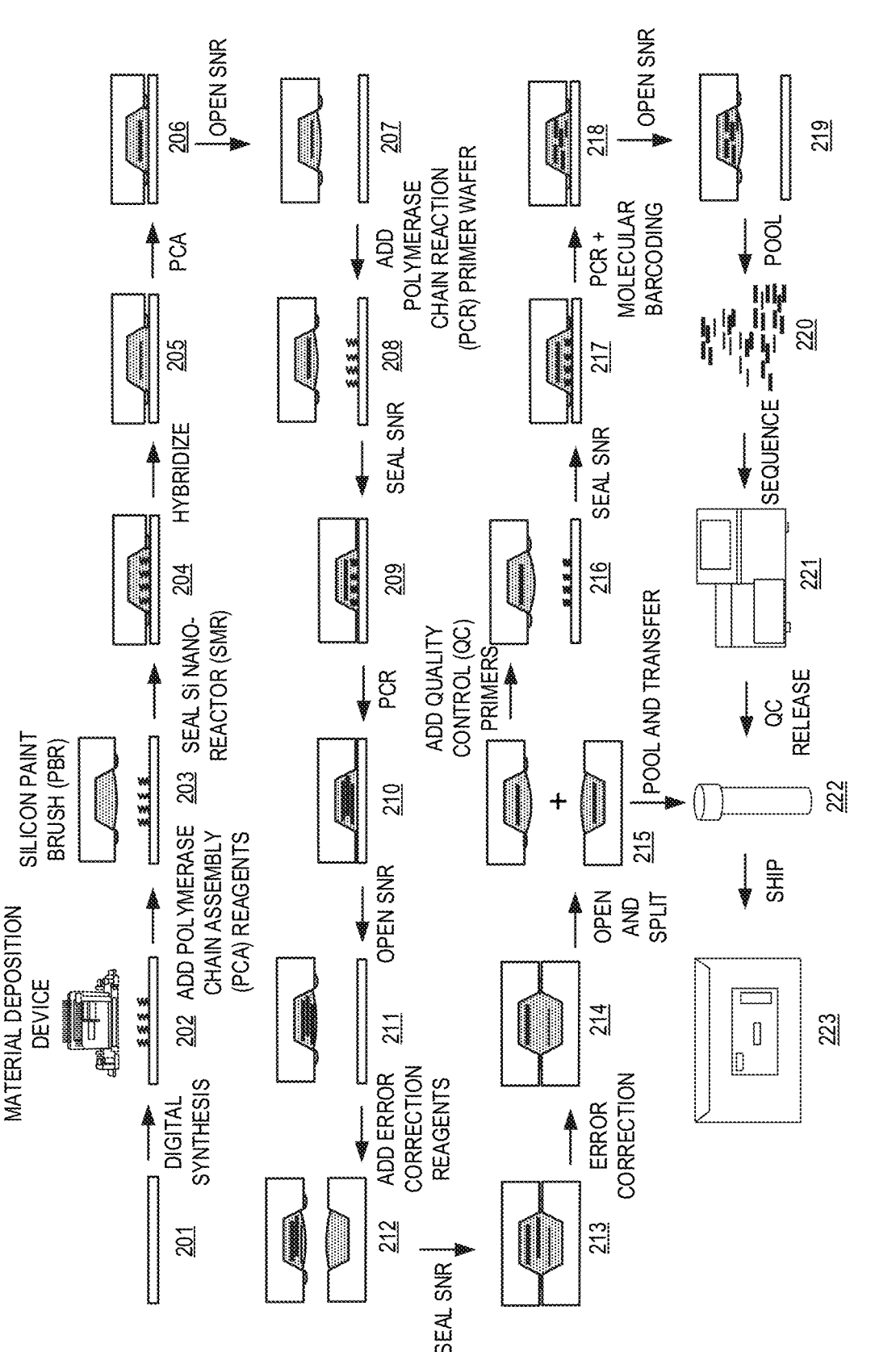
FIG. 2 depicts systems for polynucleotide synthesis and nucleic acid assembly.

Referring to the Figures, FIG. 2 illustrates an exemplary process workflow for synthesis of nucleic acids (e.g., genes) from shorter nucleic acids. The workflow is divided generally into phases: (1) de novo synthesis of a single stranded nucleic acid library, (2) joining nucleic acids to form larger fragments. (3) error correction, (4) quality control, and (5) shipment. Prior to de novo synthesis, an intended nucleic acid sequence or group of nucleic acid sequences is preselected. For example, a group of genes is preselected for generation.

Once large nucleic acids for generation are selected, a predetermined library of nucleic acids is designed for de novo synthesis. Various suitable methods are known for generating high density polynucleotide arrays. In the workflow example, a device surface layer is provided. In the example, chemistry of the surface is altered in order to improve the polynucleotide synthesis process. Areas of low surface energy are generated to repel liquid while areas of high surface energy are generated to attract liquids. The surface itself may be in the form of a planar surface or contain variations in shape, such as protrusions or microwells which increase surface area. In the workflow example, high surface energy molecules selected serve a dual function of supporting DNA chemistry, as disclosed in International Patent Application Publication WO/2015/021080, which is herein incorporated by reference in its entirety.

In situ preparation of polynucleotide arrays is generated on a solid support and utilizes single nucleotide extension process to extend multiple oligomers in parallel. A deposition device, such as a material deposition device, is designed to release reagents in a step wise fashion such that multiple polynucleotides extend, in parallel, one residue at a time to generate oligomers with a predetermined nucleic acid sequence 202. In some instances, polynucleotides are cleaved from the surface at this stage. Cleavage includes gas cleavage, e.g., with ammonia or methylamine.

The generated polynucleotide libraries are placed in a reaction chamber. In this exemplary workflow, the reaction chamber (also referred to as "nanoreactor") is a silicon coated well, containing PCR reagents and lowered onto the polynucleotide library 203. Prior to or after the sealing 204 of the polynucleotides, a reagent is added to release the polynucleotides from the substrate. In the exemplary workflow, the polynucleotides are released subsequent to sealing of the nanoreactor 205. Once released, fragments of single stranded polynucleotides hybridize in order to span an entire long range sequence of DNA. Partial hybridization 205 is possible because each synthesized polynucleotide is designed to have a small portion overlapping with at least one other polynucleotide in the pool.

After hybridization, a PCA reaction is commenced. During the polymerase cycles, the polynucleotides anneal to complementary fragments and gaps are filled in by a polymerase. Each cycle increases the length of various fragments randomly depending on which polynucleotides find each other. Complementarity amongst the fragments allows for forming a complete large span of double stranded DNA 206.

After PCA is complete, the nanoreactor is separated from the device 207 and positioned for interaction with a device having primers for PCR 208. After sealing, the nanoreactor is subject to PCR 209 and the larger nucleic acids are amplified. After PCR 210, the nanochamber is opened 211, error correction reagents are added 212, the chamber is scaled 213 and an error correction reaction occurs to remove mismatched base pairs and/or strands with poor complementarity from the double stranded PCR amplification products 214. The nanoreactor is opened and separated 215. Error corrected product is next subject to additional processing steps, such as PCR and molecular bar coding, and then packaged 222 for shipment 223.

In some instances, quality control measures are taken. After error correction, quality control steps include for example interaction with a wafer having sequencing primers for amplification of the error corrected product 216, sealing the wafer to a chamber containing error corrected amplification product 217, and performing an additional round of amplification 218. The nanoreactor is opened 219 and the products are pooled 220 and sequenced 221. After an acceptable quality control determination is made, the packaged product 222 is approved for shipment 223.

In some instances, a nucleic acid generated by a workflow such as that in FIG. 2 is subject to mutagenesis using overlapping primers disclosed herein. In some instances, a library of primers are generated by in situ preparation on a solid support and utilize single nucleotide extension process to extend multiple oligomers in parallel. A deposition device, such as a material deposition device, is designed to release reagents in a step wise fashion such that multiple polynucleotides extend, in parallel, one residue at a time to generate oligomers with a predetermined nucleic acid sequence 202.

Computer Systems

Any of the systems described herein, may be operably linked to a computer and may be automated through a computer either locally or remotely. In various instances, the methods and systems of the disclosure may further comprise software programs on computer systems and use thereof. Accordingly, computerized control for the synchronization of the dispense/vacuum/refill functions such as orchestrating and synchronizing the material deposition device movement, dispense action and vacuum actuation are within the bounds of the disclosure. The computer systems may be programmed to interface between the user specified base sequence and the position of a material deposition device to deliver the correct reagents to specified regions of the substrate.

Figure 3:
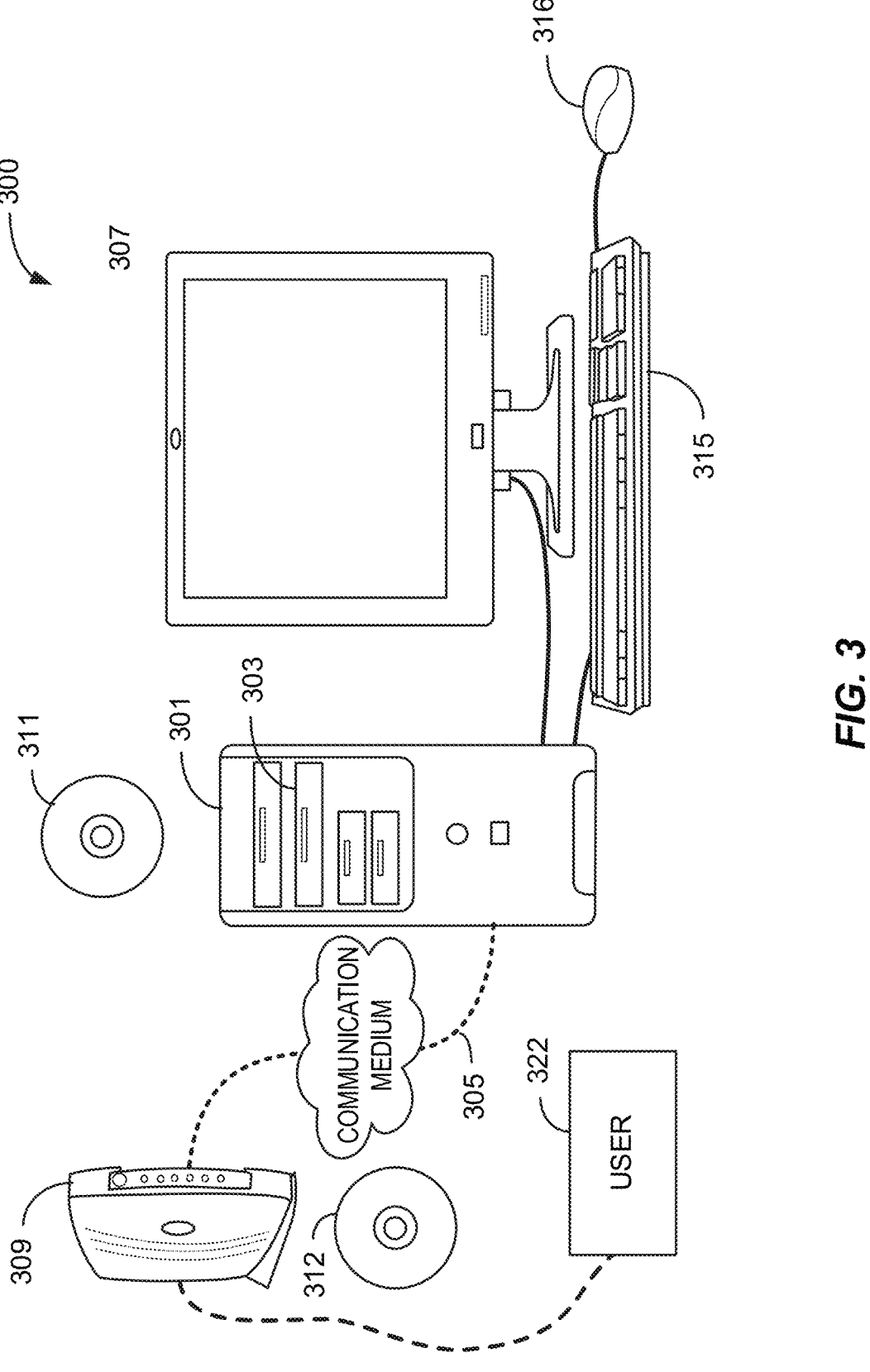
FIG. 3 illustrates a computer system.

The computer system 300 illustrated in FIG. 3 may be understood as a logical apparatus that can read instructions from media 311 and/or a network port 305, which can optionally be connected to server 309 having fixed media 312. The system, such as shown in FIG. 3 can include a CPU 301, disk drives 303, optional input devices such as keyboard 315 and/or mouse 316 and optional monitor 307. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 322 as illustrated in FIG. 3.

Figure 4:
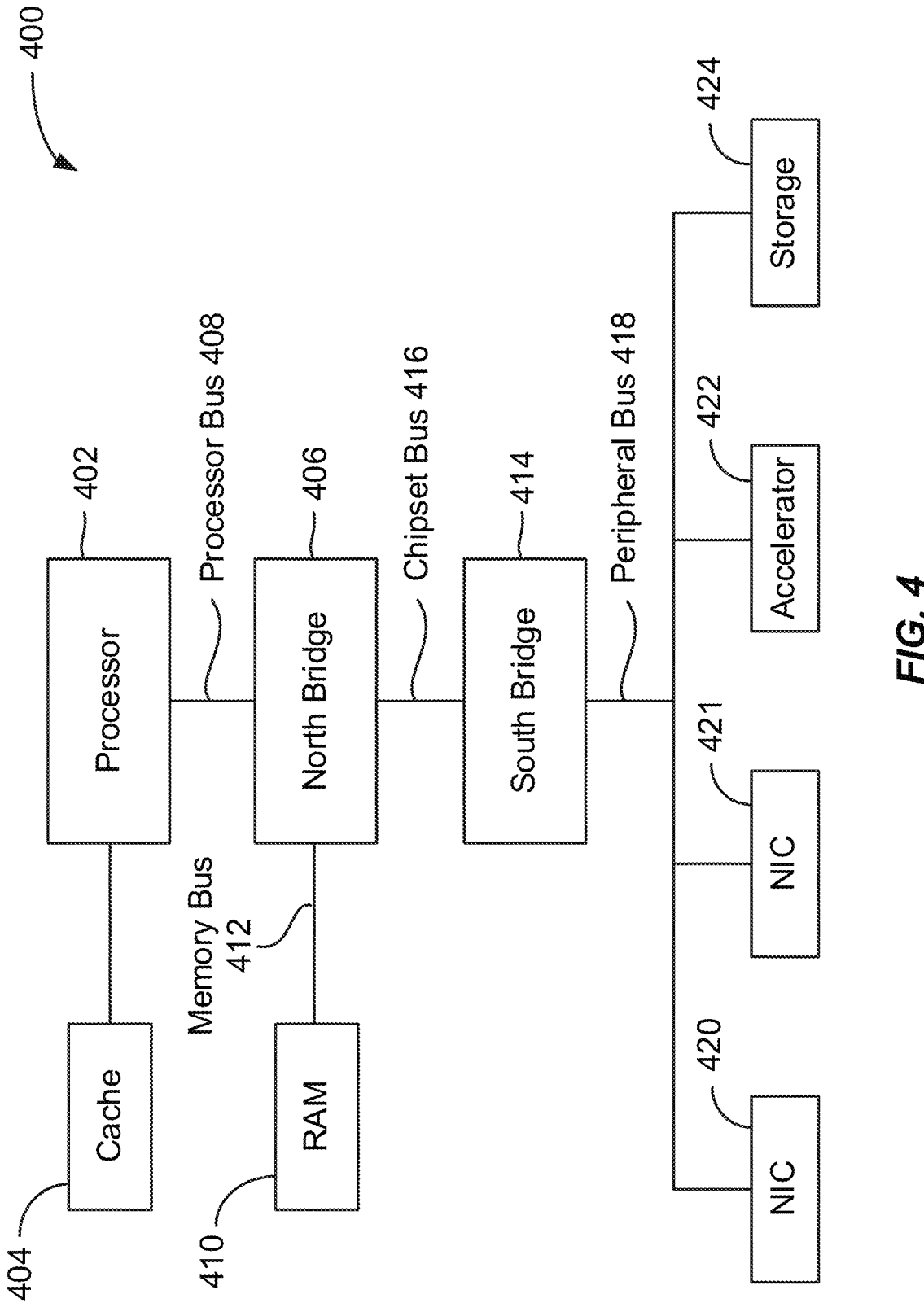
FIG. 4 is a block diagram illustrating architecture of a computer system.

As illustrated in FIG. 4, a high speed cache 404 can be connected to, or incorporated in, the processor 402 to provide a high speed memory for instructions or data that have been recently, or are frequently, used by processor 402. The processor 402 is connected to a north bridge 406 by a processor bus 408. The north bridge 406 is connected to random access memory (RAM) 410 by a memory bus 412 and manages access to the RAM 410 by the processor 402. The north bridge 406 is also connected to a south bridge 414 by a chipset bus 416. The south bridge 414 is, in turn, connected to a peripheral bus 418. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 418. In some alternative architectures, the functionality of the north bridge can be incorporated into the processor instead of using a separate north bridge chip. In some instances, system 400 can include an accelerator card 422 attached to the peripheral bus 418. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 424 and can be loaded into RAM 410 and/or cache 404 for use by the processor. The system 400 includes an operating system for managing system resources; non-limiting examples of operating systems include: Linux. Windows™, MACOS™, BlackBerry OS™, iOS™, and other functionally-equivalent operating systems, as well as application software running on top of the operating system for managing data storage and optimization in accordance with example instances of the present disclosure. In this example, system 400 also includes network interface cards (NICs) 420 and 421 connected to the peripheral bus for providing network interfaces to external storage, such as Network Attached Storage (NAS) and other computer systems that can be used for distributed parallel processing.

Figure 5:
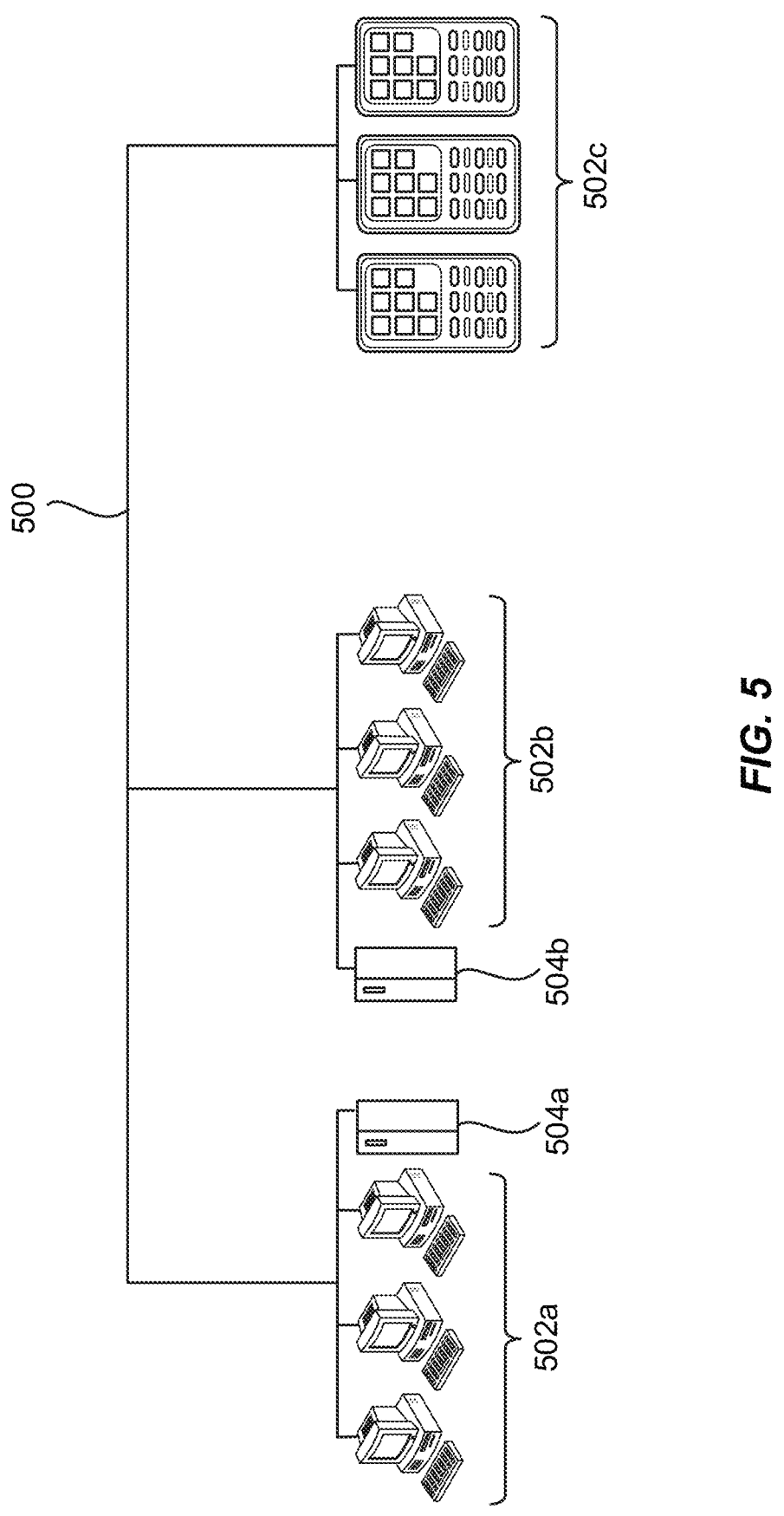
FIG. 5 is a block diagram of a multiprocessor computer system using a shared virtual address memory space.

FIG. 5 is a diagram showing a network 500 with a plurality of computer systems 502a, and 502b, a plurality of cell phones and personal data assistants 502e, and Network Attached Storage (NAS) 504, and 504b. In example instances, systems 502a, 502b, and 502e can manage data storage and optimize data access for data stored in Network Attached Storage (NAS) 504a and 504b. A mathematical model can be used for the data and be evaluated using distributed parallel processing across computer systems 502a, and 502b, and cell phone and personal data assistant systems 502c. Computer systems 502a, and 502b, and cell phone and personal data assistant systems 502c can also provide parallel processing for adaptive data restructuring of the data stored in Network Attached Storage (NAS) 504a and 504b. FIG. 5 illustrates an example only, and a wide variety of other computer architectures and systems can be used in conjunction with the various instances of the present disclosure. For example, a blade server can be used to provide parallel processing. Processor blades can be connected through a back plane to provide parallel processing. Storage can also be connected to the back plane or as Network Attached Storage (NAS) through a separate network interface. In some example instances, processors can maintain separate memory spaces and transmit data through network interfaces, back plane or other connectors for parallel processing by other processors. In other instances, some or all of the processors can use a shared virtual address memory space.

Figure 6:
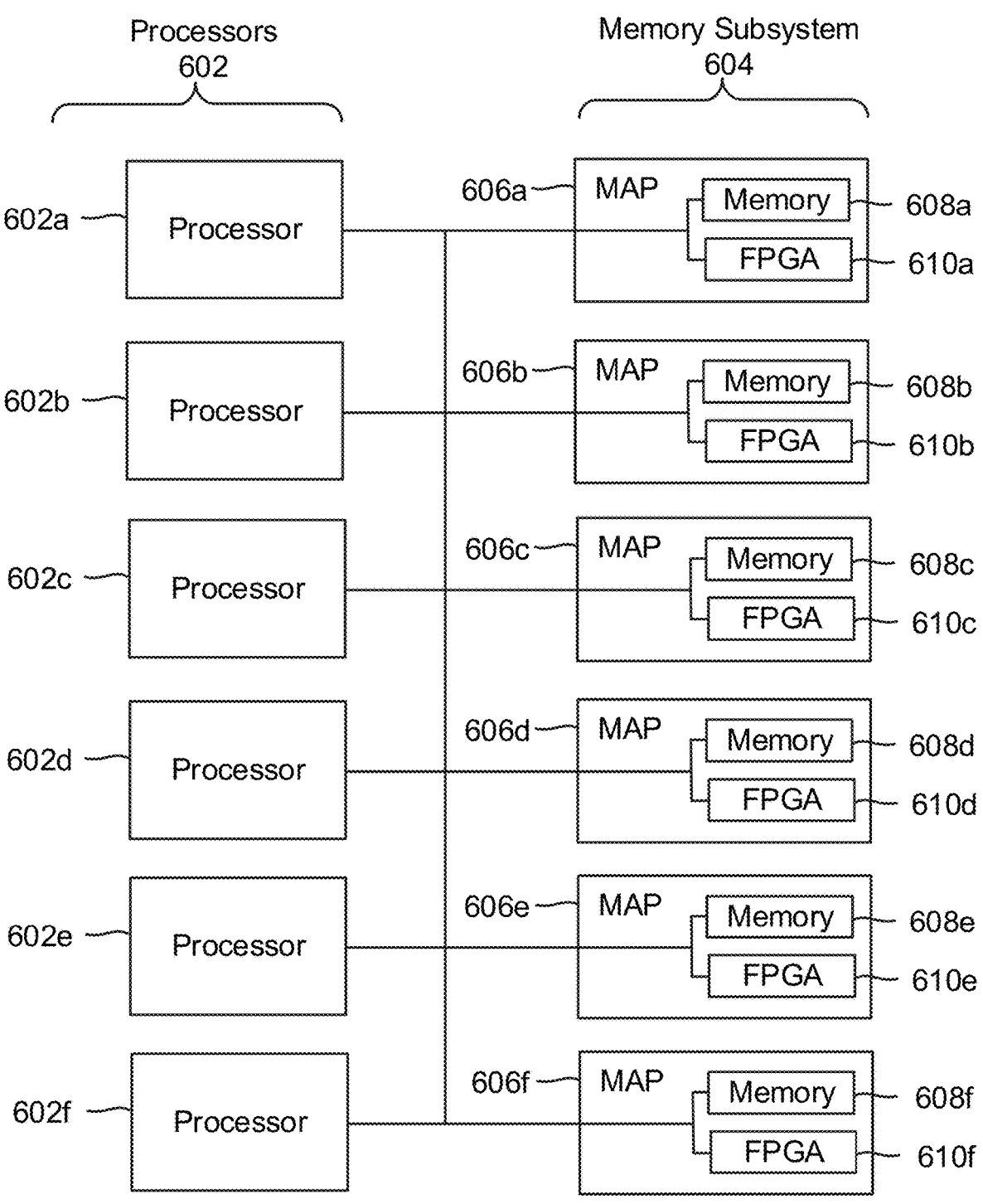
FIG. 6 is a diagram demonstrating a network configured to incorporate a plurality of computer systems, a plurality of cell phones and personal data assistants, and Network Attached Storage (NAS).

FIG. 6 is a block diagram of a multiprocessor computer system 600 using a shared virtual address memory space in accordance with an example instance. The system includes a plurality of processors 602a-f that can access a shared memory subsystem 604. The system incorporates a plurality of programmable hardware memory algorithm processors (MAPs) 606a-f in the memory subsystem 604. Each MAP 606a-f can comprise a memory 608a-f and one or more field programmable gate arrays (FPGAs) 610a-f. The MAP provides a configurable functional unit and particular algorithms or portions of algorithms can be provided to the FPGAs 610n-f for processing in close coordination with a respective processor. For example, the MAPs can be used to evaluate algebraic expressions regarding the data model and to perform adaptive data restructuring in example instances. In this example, each MAP is globally accessible by all of the processors for these purposes. In one configuration, each MAP can use Direct Memory Access (DMA) to access an associated memory 608a-f, allowing it to execute tasks independently of, and asynchronously from the respective microprocessor 602a-f. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example instances, including systems using any combination of general processors, co-processors, FPGAs and other programmable logic devices, system on chips (SOCs), application specific integrated circuits (ASICs), and other processing and logic elements. In some instances, all or part of the computer system can be implemented in software or hardware. Any variety of data storage media can be used in connection with example instances, including random access memory, hard drives, flash memory, tape drives, disk arrays, Network Attached Storage (NAS) and other local or distributed data storage devices and systems.

In example instances, the computer system can be implemented using software modules executing on any of the above or other computer architectures and systems. In other instances, the functions of the system can be implemented partially or completely in firmware, programmable logic devices such as field programmable gate arrays (FPGAs) as referenced in FIG. 4, system on chips (SOCs), application specific integrated circuits (ASICs), or other processing and logic elements. For example, the Set Processor and Optimizer can be implemented with hardware acceleration through the use of a hardware accelerator card, such as accelerator card 422 illustrated in FIG. 4.

The following examples are set forth to illustrate more clearly the principle and practice of embodiments disclosed herein to those skilled in the art and are not to be construed as limiting the scope of any claimed embodiments. Unless otherwise stated, all parts and percentages are on a weight basis.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Functionalization of a Substrate Surface

A substrate was functionalized to support the attachment and synthesis of a library of polynucleotides. The substrate surface was first wet cleaned using a piranha solution comprising 90% $H_2SO_4$ and 10% $H_2O_2$ for 20 minutes. The substrate was rinsed in several beakers with deionized water, held under a deionized water gooseneck faucet for 5 min, and dried with $N_2$. The substrate was subsequently soaked in $NH_4OH$ (1:100; 3 mL:300 mL) for 5 min, rinsed with DI water using a handgun, soaked in three successive beakers with deionized water for 1 min each, and then rinsed again with deionized water using the handgun. The substrate was then plasma cleaned by exposing the substrate surface to $O_2$. A SAMCO PC-300 instrument was used to plasma etch $O_2$ at 250 watts for 1 min in downstream mode.

The cleaned substrate surface was actively functionalized with a solution comprising N-(3-triethoxysilylpropyl)-4-hydroxybutyramide using a YES-1224P vapor deposition oven system with the following parameters: 0.5 to 1 torr, 60 min. 70° C., 135° C. vaporizer. The substrate surface was resist coated using a Brewer Science 200X spin coater. SPR™ 3612 photoresist was spin coated on the substrate at 2500 rpm for 40 sec. The substrate was pre-baked for 30 min at 90° C., on a Brewer hot plate. The substrate was subjected to photolithography using a Karl Suss MA6 mask aligner instrument. The substrate was exposed for 2.2 sec and developed for 1 min in MSF 26A. Remaining developer was rinsed with the handgun and the substrate soaked in water for 5 min. The substrate was baked for 30 min at 100° C., in the oven, followed by visual inspection for lithography defects using a Nikon L200. A cleaning process was used to remove residual resist using the SAMCO PC-300 instrument to $O_2$ plasma etch at 250 watts for 1 min.

The substrate surface was passively functionalized with a 100 µL, solution of perfluorooctyltrichlorosilane mixed with 10 µL light mineral oil. The substrate was placed in a chamber, pumped for 10 min, and then the valve was closed to the pump and left to stand for 10 min. The chamber was vented to air. The substrate was resist stripped by performing two soaks for 5 min in 500 mL NMP at 70° C., with ultrasonication at maximum power (9 on Crest system). The substrate was then soaked for 5 min in 500 ml isopropanol at room temperature with ultrasonication at maximum power. The substrate was dipped in 300 mL of 200 proof ethanol and blown dry with $N_2$. The functionalized surface was activated to serve as a support for polynucleotide synthesis.

Example 2: Synthesis of a 50-mer Sequence on an Oligonucleotide Synthesis Device A two dimensional oligonucleotide synthesis device was assembled into a flowcell, which was connected to a flowcell (Applied Biosystems ("AB1394 DNA Synthesizer")). The two-dimensional oligonucleotide synthesis device was uniformly functionalized with N-(3-TRIETHOXYSILYLPRO-PYL)-4-HYDROXYBUTYRAMIDE (Gelest) was used to synthesize an exemplary polynucleotide of 50 bp ("50-mer polynucleotide") using polynucleotide synthesis methods described herein.

The sequence of the 50-mer was as described in SEQ ID NO.: 1, 5'AGACAATCAACCATTTGGGGTGGAC-AGCCTTGACCTCTAGACTTCGGCAT##TTT TTTTTTT3'(SEQ ID NO.: 1), where #denotes Thymidine-succinyl hexamide CED phosphoramidite (CLP-2244 from ChemGenes), which is a cleavable linker enabling the release of polynucleotides from the surface during deprotection.

The synthesis was done using standard DNA synthesis chemistry (coupling, capping, oxidation, and deblocking) according to the protocol in Table 1 and an ABI synthesizer.

TABLE 1

| General DNA Synthesis Process Name | Table 1 Process Step | Time (sec) |
|---|---|---|
| | Synthesis Protocol | |
| WASH (Acetonitrile Wash Flow) | Acetonitrile System Flush | 4 |
| | Acetonitrile to Flowcell | 23 |
| | N2 System Flush | 4 |
| | Acetonitrile System Flush | 4 |
| DNA BASE ADDITION (Phosphoramidite + Activator Flow) | Activator Manifold Flush | 2 |
| | Activator to Flowcell | 6 |
| | Activator + | 6 |
| | Phosphoramidite to Flowcell | 0.5 |
| | Activator to Flowcell | |
| | Activator + | 5 |
| | Phosphoramidite to Flowcell | |
| | Activator to Flowcell | 0.5 |
| | Activator + | 5 |
| | Phosphoramidite to Flowcell | |
| | Activator to Flowcell | 0.5 |
| | Activator + | 5 |
| | Phosphoramidite to Flowcell | |
| | Incubate for 25 sec | 25 |
| WASH (Acetonitrile Wash Flow) | Acetonitrile System Flush | 4 |
| | Acetonittile to Flowcell | 15 |
| | N2 System Flush | 4 |
| | Acetonitrile System Flush | 4 |
| DNA BASE ADDITION (Phosphoramidite + Activator Flow) | Activator Manifold Flush | 2 |
| | Activator to Flowcell | 5 |
| | Activator + | 18 |
| | Phosphoramidite to Flowcell | |
| | Incubate for 25 sec | 25 |
| WASH (Acetonitrile Wash Flow) | Acetonitrile System Flush | 4 |
| | Acetonitrile to Flowcell | 15 |
| | N2 System Flush | 4 |
| | Acetonitrile System Flush | 4 |
| CAPPING (CapA + B, 1:1, Flow) | CapA + B to Flowcell | 15 |
| WASH (Acetonitrile Wash Flow) | Acetonitrile System Flush | 4 |
| | Acetonitrile to Flowcell | 15 |
| | Acetonitrile System Flush | 4 |
| OXIDATION (Oxidizer Flow) | Oxidizer to Flowcell | 18 |
| WASH (Acetonitrile Wash Flow) | Acetonitrile System Flush | 4 |
| | N2 System Flush | 4 |
| | Acetonitrile System Flush | 4 |
| | Acetonitrile to Flowcell | 15 |
| | Acetonitrile System Flush | 4 |
| | Acetonitrile to Flowcell | 15 |
| | N2 System Flush | 4 |
| | Acetonitrile System Flush | 4 |
| | Acetonitrile to Flowcell | 23 |
| | N2 System Flush | 4 |
| | Acetonitrile System Flush | 4 |
| DEBLOCKING (Deblock Flow) | Deblock to Flowcell | 36 |

TABLE 1-continued

| Synthesis Protocol | | |
|---|---|---|
| General DNA Synthesis Process Name | Table 1 Process Step | Time (sec) |
| WASH (Acetonitrile Wash Flow) | Acetonitrile System Flush | 4 |
| | N2 System Flush | 4 |
| | Acetonitrile System Flush | 4 |
| | Acetonitrile to Flowcell | 18 |
| | N2 System Flush | 4.13 |
| | Acetonitrile System Flush | 4.13 |
| | Acetonitrile to Flowcell | 15 |

The phosphoramidite/activator combination was delivered similar to the delivery of bulk reagents through the flowcell. No drying steps were performed as the environment stays "wet" with reagent the entire time.

The flow restrictor was removed from the AB1394 DNA Synthesizer to enable faster flow. Without flow restrictor, flow rates for amidites (0.1 M in ACN), Activator, (0.25M Benzoylthiotetrazole ("BTT"; 30-3070-xx from GlenResearch) in ACN), and Ox (0.02M 12 in 20% pyridine, 10% water, and 70% THF) were roughly ~100 uL/sec, for acetonitrile ("ACN") and capping reagents (1:1 mix of CapA and CapB, wherein CapA is acetic anhydride in THF/Pyridine and CapB is 16% 1-methylimidizole in THF), roughly ~200 uL/sec, and for Deblock (3% dichloroacetic acid in toluene), roughly ~300 uL/sec (compared to ~50 uL/sec for all reagents with flow restrictor). The time to completely push out Oxidizer was observed, the timing for chemical flow times was adjusted accordingly and an extra ACN wash was introduced between different chemicals. After polynucleotide synthesis, the chip was deprotected in gaseous ammonia overnight at 75 psi. Five drops of water were applied to the surface to recover polynucleotides. The recovered polynucleotides were then analyzed on a BioAnalyzer small RNA chip (data not shown).

Example 3: Synthesis of a 100-mer Sequence on an Oligonucleotide Synthesis Device The same process as described in Example 2 for the synthesis of the 50-mer sequence was used for the synthesis of a 100-mer polynucleotide ("100-mer polynucleotide"; 5' CGGGATCCTTATCGTCATCGTCGTACAGATCCCG-ACCCATTTGCTGTCCACCAGTCATGCTAGCCATAC-CATGATGATGATGATGATGAGAACCCCGCAT##TTT-TTTTTT T3', where #denotes Thymidine-succinyl hexamide CED phosphoramidite (CLP-2244 from ChemGenes); SEQ ID NO.: 2) on two different silicon chips, the first one uniformly functionalized with N-(3-TRIETHOXYSILYL-PROPYL)-4-HYDROXYBUTYRAMIDE and the second one functionalized with 5/95 mix of 11-acetoxyundecyltriethoxysilane and n-decyltriethoxysilane, and the polynucleotides extracted from the surface were analyzed on a Bio-Analyzer instrument (data not shown).

All ten samples from the two chips were further PCR amplified using a forward (5'ATGCGGGGTTCTCAT-CATC3'; SEQ ID NO.: 3) and a reverse (5'CGGGATCCT-TATCGTCATCG3'; SEQ ID NO.: 4) primer in a 50 uL PCR mix (25 uL NEB Q5 Master Mix, 2.5 uL 10 uM Forward primer, 2.5 uL 10 uM Reverse primer, 1 uL polynucleotide extracted from the surface, and water up to 50 uL) using the following thermal cycling program:

98° C., 30 sec
98° C., 10 sec; 63° C., 10 sec; 72° C., 10 sec; repeat 12 cycles
72° C., 2 min The PCR products were also run on a BioAnalyzer (data not shown), demonstrating sharp peaks at the 100-mer position. Next, the PCR, amplified samples were cloned, and Sanger sequenced. Table 2 summarizes the results from the Sanger sequencing for samples taken from spots 1-5 from chip 1 and for samples taken from spots 6-10 from chip 2.

TABLE 2

| Sequencing Results | | |
|---|---|---|
| Spot | Error rate | Cycle efficiency |
| 1 | 1/763 bp | 99.87% |
| 2 | 1/824 bp | 99.88% |
| 3 | 1/78 bp | 99.87% |
| 4 | 1/429 bp | 99.77% |
| 5 | 1/1525 bp | 99.93% |
| 6 | 1/1615 bp | 99.94% |
| 7 | 1/531 bp | 99.81% |
| 8 | 1/1769 bp | 99.94% |
| 9 | 1/854 bp | 99.88% |
| 10 | 1/1451 bp | 99.93% |

Thus, the high quality and uniformity of the synthesized polynucleotides were repeated on two chips with different surface chemistries. Overall 89%, corresponding to 233 out of 262 of the 100-mers that were sequenced were perfect sequences with no errors. Table 3 summarizes error characteristics for the sequences obtained from the polynucleotides samples from spots 1-10.

TABLE 3

| Error Characteristics | | | | | |
|---|---|---|---|---|---|
| | Sample ID/Spot no. | | | | |
| | OSA_0046/1 | OSA_0047/2 | OSA_0048/3 | OSA_0049/4 | OSA_0050/5 |
| Total Sequences | 32 | 32 | 32 | 32 | 32 |
| Sequencing Quality | 25 of 28 | 27 of 27 | 26 of 30 | 21 of 23 | 25 of 26 |
| Oligo Quality | 23 of 25 | 25 of 27 | 22 of 26 | 18 of 21 | 24 of 25 |
| ROI Match Count | 2500 | 2698 | 2561 | 2122 | 2499 |
| ROI Mutation | 2 | 2 | 1 | 3 | 1 |
| ROI Multi Base Deletion | 0 | 0 | 0 | 0 | 0 |
| ROI Small Insertion | 1 | 0 | 0 | 0 | 0 |
| ROI Single Base Deletion | 0 | 0 | 0 | 0 | 0 |

TABLE 3-continued

| Error Characteristics | | | | | |
|---|---|---|---|---|---|
| Large Deletion Count | 0 | 0 | 1 | 0 | 0 |
| Mutation: G > A | 2 | 2 | 1 | 2 | 1 |
| Mutation: T > C | 0 | 0 | 0 | 1 | 0 |
| ROI Error Count | 3 | 2 | 2 | 3 | 1 |
| ROI Error Rate | Err: ~1 in 834 | Err: ~1 in 1350 | Err: ~1 in 1282 | Err: ~1 in 708 | Err: ~1 in 2500 |
| ROI Minus Primer Error Rate | MP Err: ~1 in 763 | MP Err: ~1 in 824 | MP Err: ~1 in 780 | MP Err: ~1 in 429 | MP Err: ~1 in 1525 |

| | Sample ID/Spot no. | | | | |
|---|---|---|---|---|---|
| | OSA_0051/6 | OSA_0052/7 | OSA_0053/8 | OSA_0054/9 | OSA_0055/10 |
| Total Sequences | 32 | 32 | 32 | 32 | 32 |
| Sequencing Quality | 29 of 30 | 27 of 31 | 29 of 31 | 28 of 29 | 25 of 28 |
| Oligo Quality | 25 of 29 | 22 of 27 | 28 of 29 | 26 of 28 | 20 of 25 |
| ROI Match Count | 2666 | 2625 | 2899 | 2798 | 2348 |
| ROI Mutation | 0 | 2 | 1 | 2 | 1 |
| ROI Multi Base Deletion | 0 | 0 | 0 | 0 | 0 |
| ROI Small Insertion | 0 | 0 | 0 | 0 | 0 |
| ROI Single Base Deletion | 0 | 0 | 0 | 0 | 0 |
| Large Deletion Count | 1 | 1 | 0 | 0 | 0 |
| Mutation: G > A | 0 | 2 | 1 | 2 | 1 |
| Mutation: T > C | 0 | 0 | 0 | 0 | 0 |
| ROI Error Count | 1 | 3 | 1 | 2 | 1 |
| ROI Error Rate | Err: ~1 in 2667 | Err: ~1 in 876 | Err: ~1 in 2900 | Err: ~1 in 1400 | Err: ~1 in 2349 |
| ROI Minus Primer Error Rate | MP Err: ~1 in 1615 | MP Err: ~1 in 531 | MP Err: ~1 in 1769 | MP Err: ~1 in 854 | MP Err: ~1 in 1451 |

Example 4. Protocol for Generating Covalently Closed DNA

DNA was amplified in a 96 well plate using the protocol in Table 4. The primers used were DB_Uracil F(AAACCU-CAAAAGAGGUTUCGctgatcgagtgtagccagatct) (SEQ ID NO: 5) and DB_Uracil R(AAACCUCAAAAGAGGU-TUCGcctgcaggatagctgacgac) (SEQ ID NO: 6).

TABLE 4

| Reaction parameters | | | | |
|---|---|---|---|---|
| Kapa-Uracil PCR 100 uL Reaction | Initial Conc | Final Conc | 1X (uL) | |
| 10 ng/uL D'NA template (Lambda GD or IgG4 K TC) | | 20 ng | 2 | |
| 10 uM covalently closed Uracil F Primer | 10 uM | 0.6 uM | 6 | |
| 10 uM covalently closed Uracil R Primer | 10 uM | 0.6 uM | 6 | |
| Kapa-Uracil 2× Master Mix | 2× | 1× | 50 | |
| HyPure Molecular Biology Grade Water | | | 36 | |
| Final Volume | | | 100 | |

Cycling conditions were 95° C., for 2 minutes; followed by 20 cycles of denaturing at 98° C., for 20 seconds, annealing at 65° C., for 15 seconds, and extension for 72° C. for 2 minutes; followed by a final extension time of 2 minutes. Extension times of 15 seconds were used for targets of 1 kb or less in size, and extension times of 30-60 seconds/kb were used for longer fragments.

The reaction was then used as a template for the following reaction listed in Table 5.

TABLE 5

| Reaction parameters | | | | |
|---|---|---|---|---|
| Kapa-Uracil PCR 100 uL Reaction | Initial Conc | Final Conc | 1X (uL) | Order of addition |
| NUGE Reaction | | | 2 | 1 |
| 10 uM covalently closed Uracil F Primer | 10 uM | 0.6 uM | 6 | 2 |
| 10 uM covalently closed Uracil R Primer | 10 uM | 0.6 uM | 6 | 2 |
| Kapa-Uracil 2× Master Mix | 2× | 1× | 50 | 3 |
| HyPure Molecular Biology Grade Water | | | 43 | 3 |
| Final Volume | | | 100 | |

Cycling conditions were 95° C., for 2 minutes; followed by 11 cycles of denaturing at 98° C., for 20 seconds, annealing at 65° C., for 15 seconds, and extension for 72° C., for 2 minutes; followed by a final extension time of 2 minutes. Extension times of 15 seconds were used for targets of 1 kb or less in size, and extension times of 30-60 seconds/kb were used for longer fragments.

Six PCR reactions were pooled together and purified using SPRI purification. The eluted DNA is analyzed using a Bioanalyzer and Qubit to identify yield and quality (data not shown). A USER digest was performed to excise the uracils from the covalently closed nucleic acid primers and allow the formation of the hairpin structures, 20 uL of purified Kapa-U PCR DNA (7-10 ug) was combined with 2.5 uL of 10× Cutsmart buffer and 2.5 uL of USER 1 U/μL. The reaction was incubated at 37° C., for 90 minutes.

A T4 ligation was performed to seal the nicks left by the uracil and hairpin after the digest. The reaction components listed in Table 6 were combined to create a master mix, then 25 ul of each Ligation mix and 25 uL was combined into each well of the 96 well plate containing the USER treated and annealed DNA. The plate was sealed, spun down, mixed, and spun down again. The reaction was incubated at 16° C., for 1 hour.

TABLE 6

| Ligation reaction | |
| --- | --- |
| T4 ligation | 1X (50 uL) |
| T4 ligase buffer | 5 |
| T4 ligase (400,000 units/mL.) | 1 |
| Water | 19 |
| Subtotal | 25 |
| USER Treated and annealed DNA | 25 |

Figure 7:
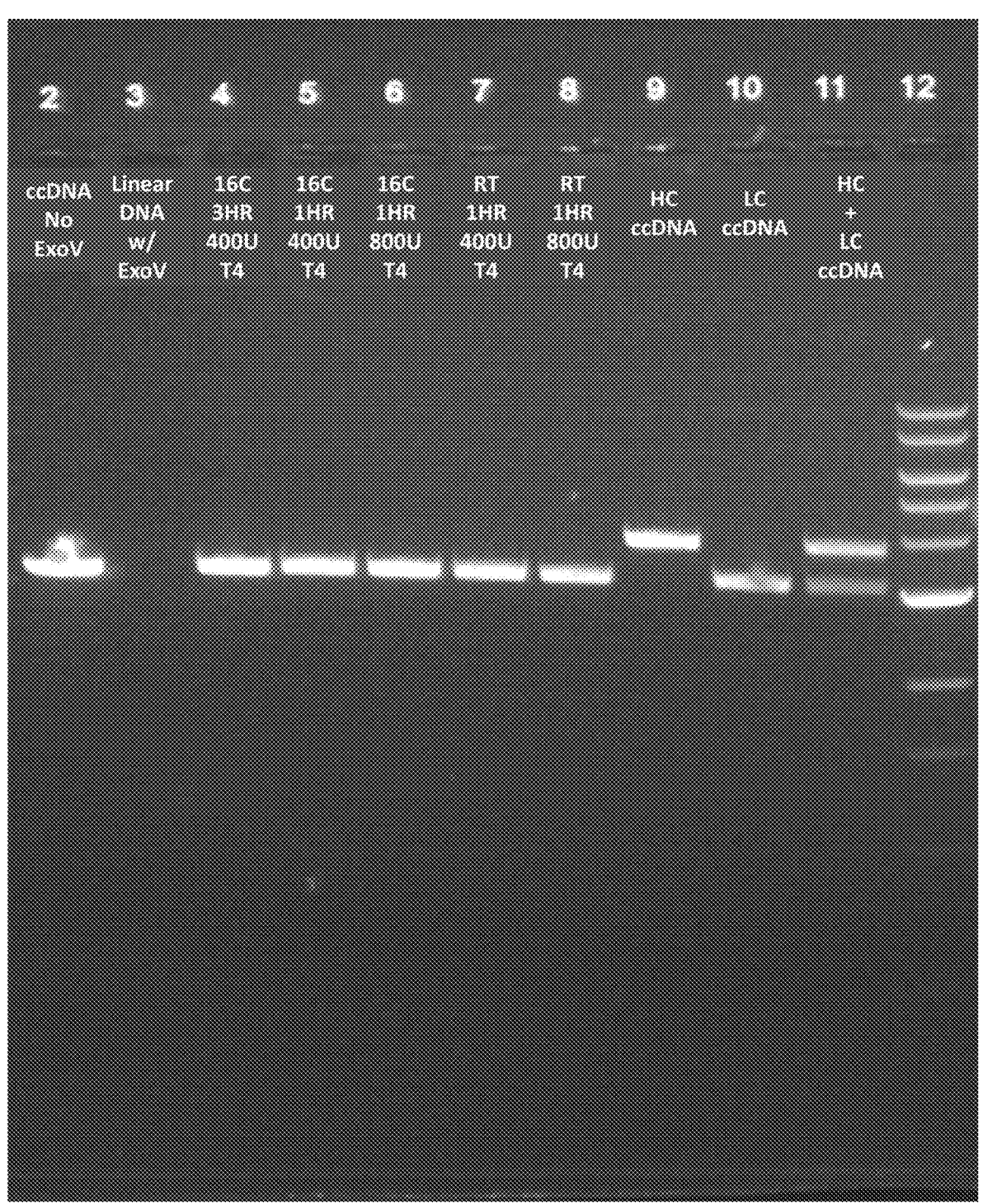
FIG. 7 illustrates the effect of digestion with Exonuclease V on linear and covalently closed DNA.
Figure 8A:
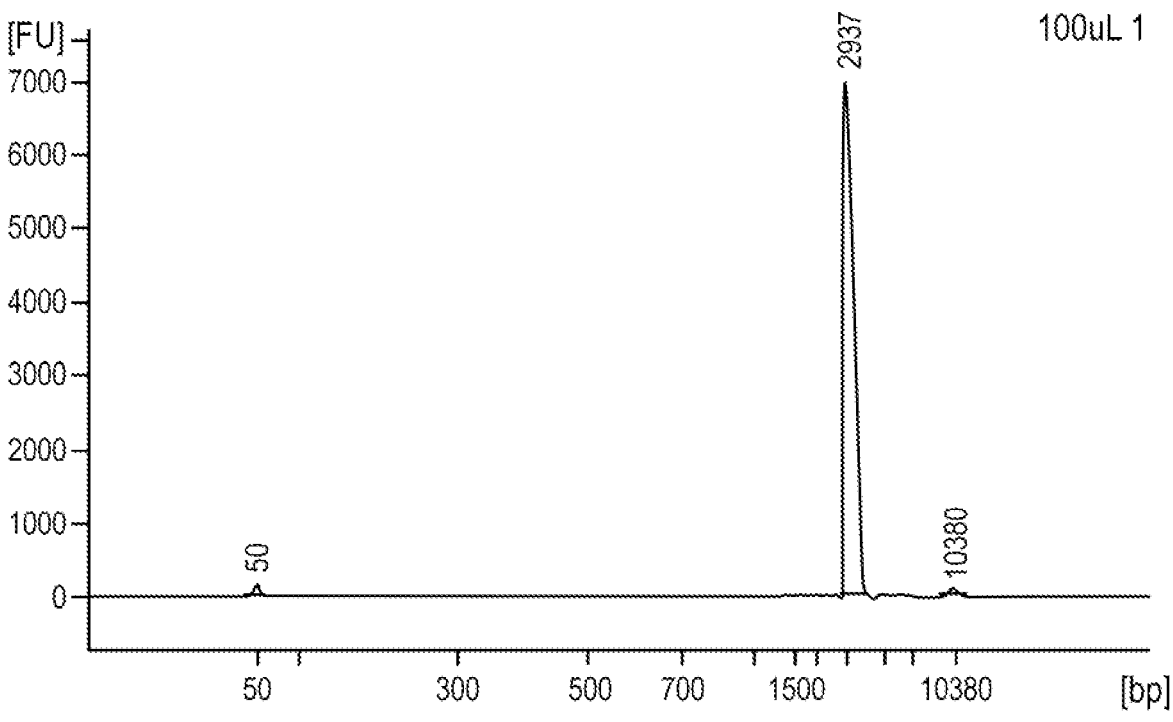
FIGS. 8A-8H depict quality analysis results of the PCR reactions prior to USER digestion.
Figure 8B:
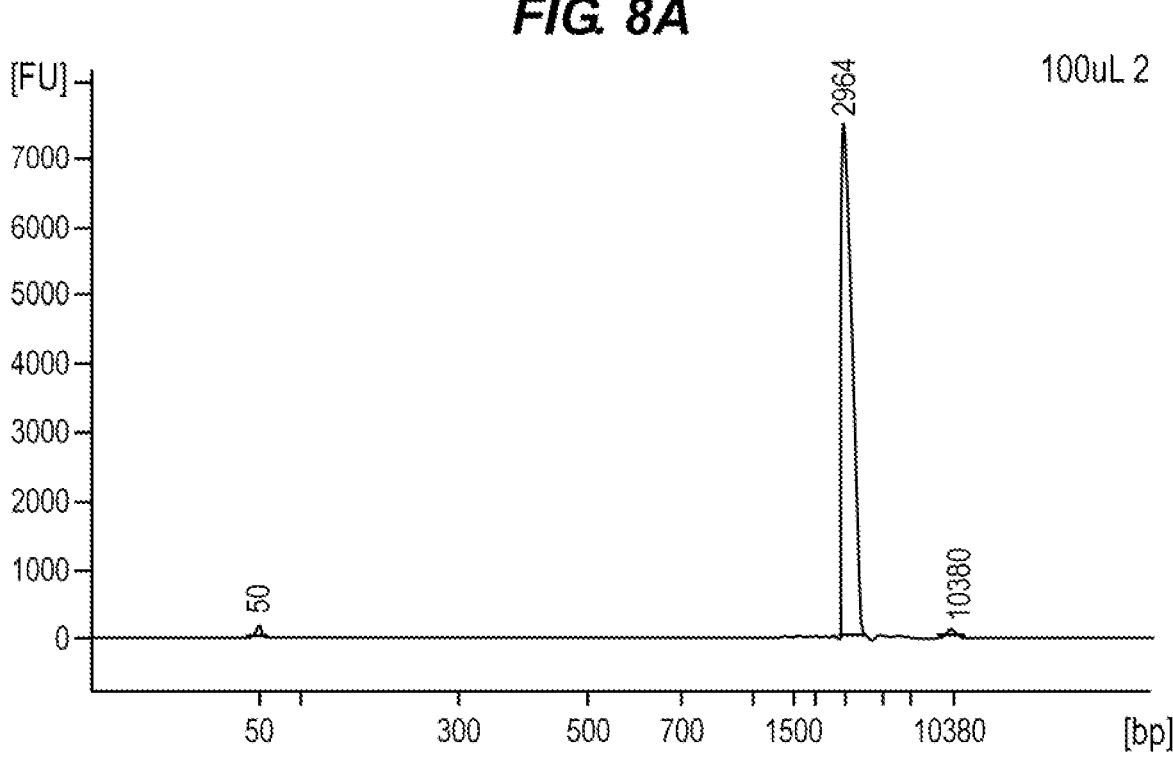
Figure 8C:
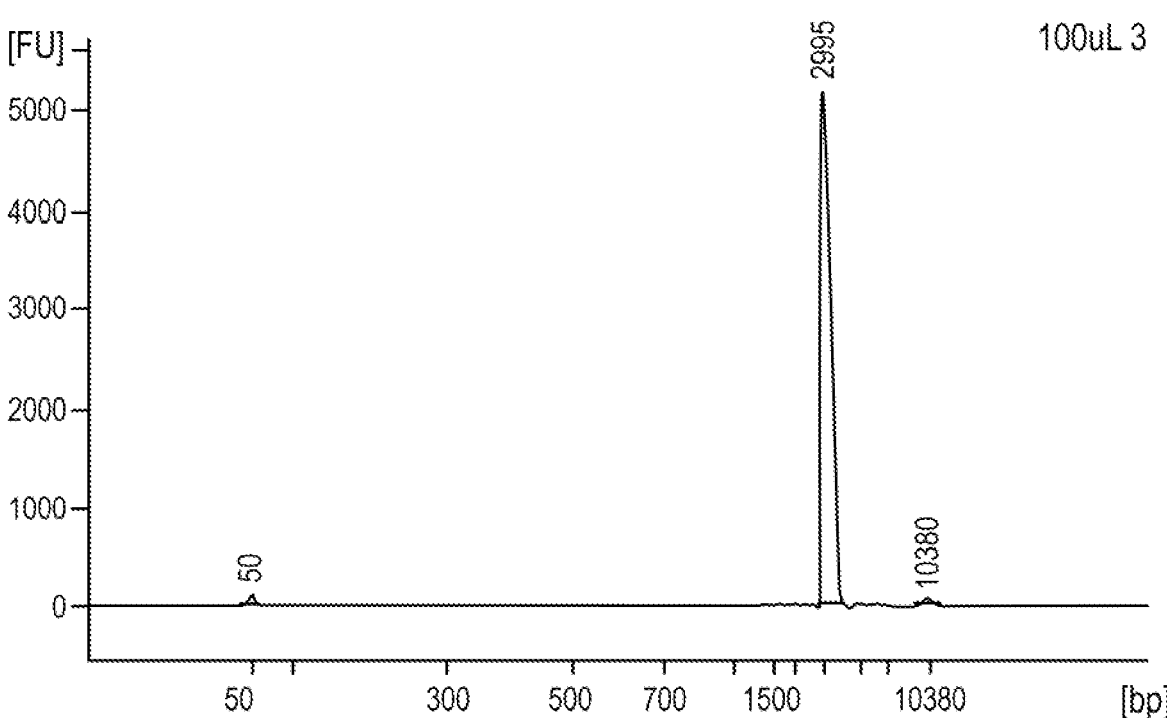
Figure 8D:
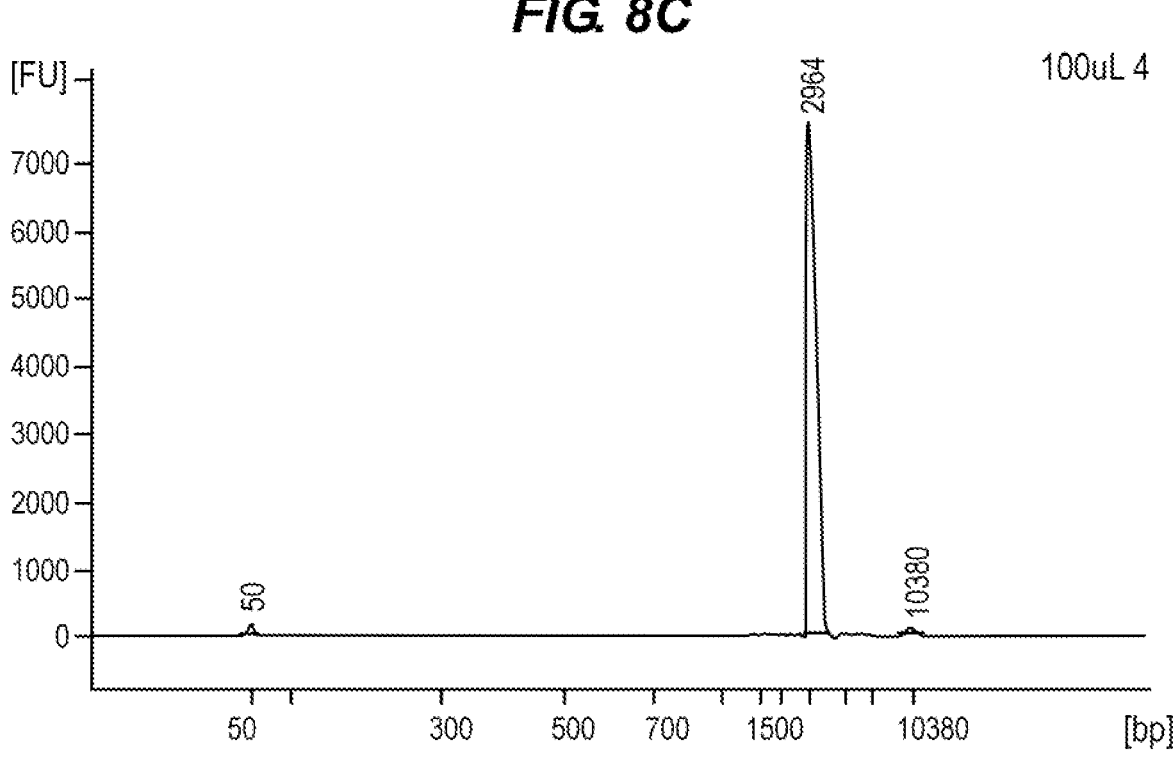
Figure 8E:
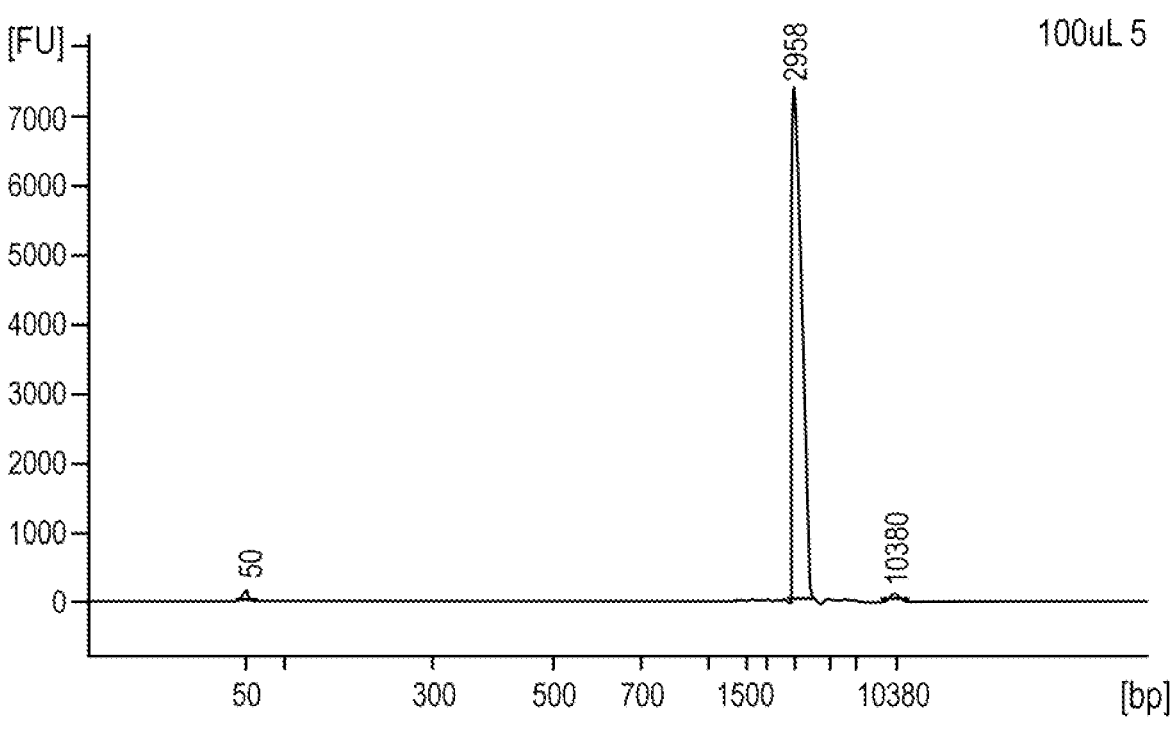
Figure 8F:
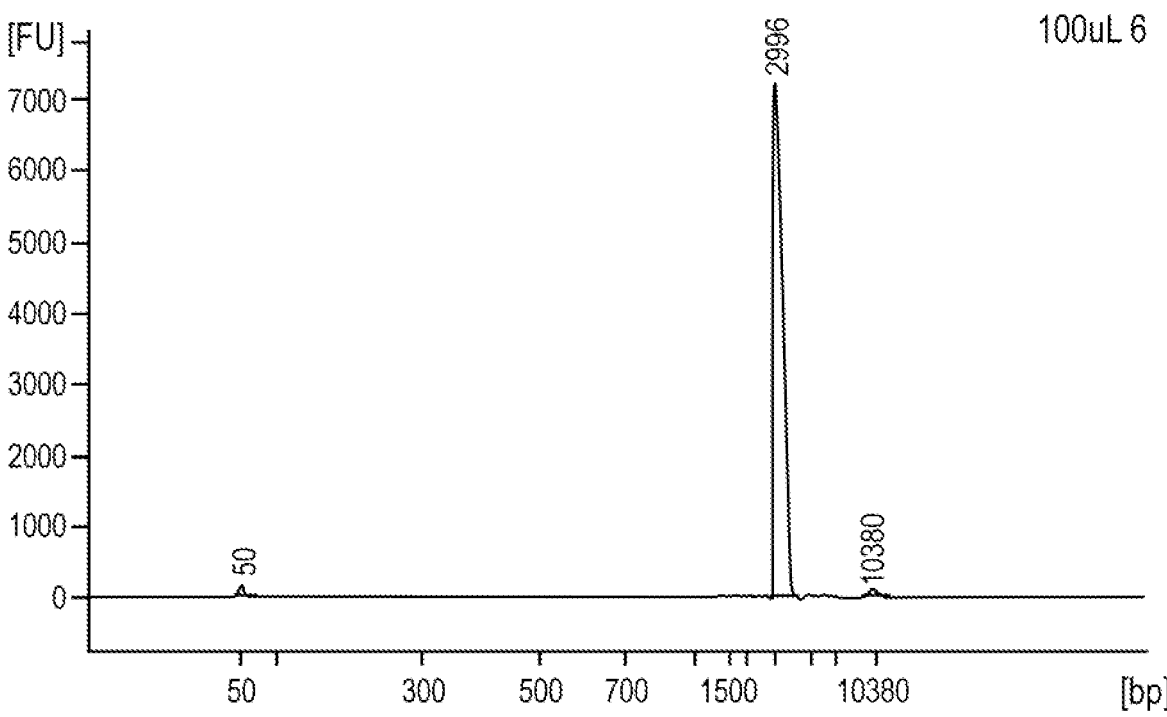
Figure 8G:
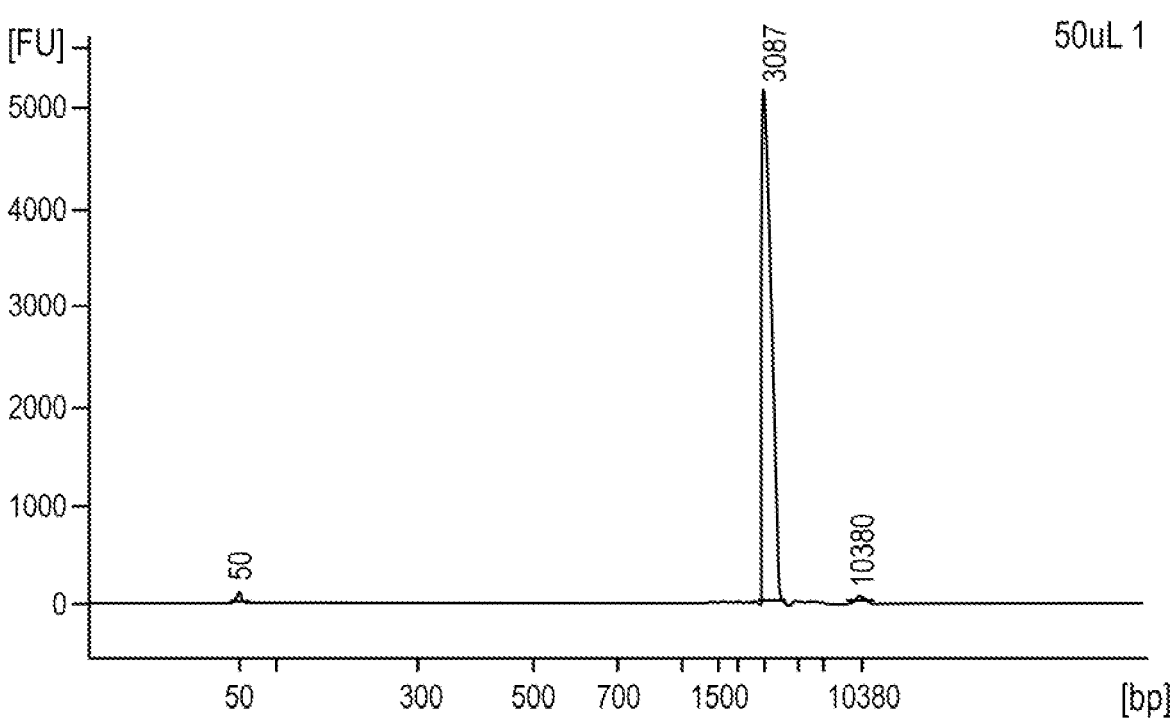
Figure 8H:
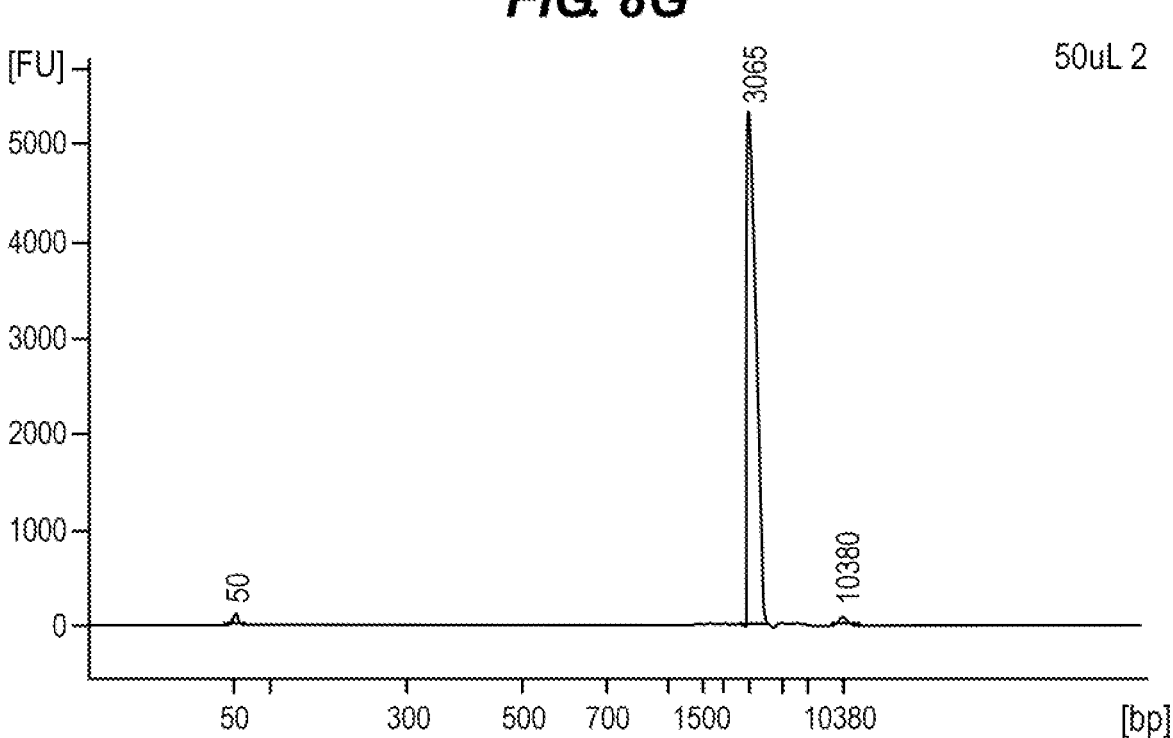

The reaction is then diluted 1:1 with 50 uL water and purified using SPRI purification. 200 ng of the material was run through an ExoV digested to test for completion of the covalently closed nucleic acid. The components in Table 7 were combined and incubated at 37° C., for 30 minutes. To stop the reaction, EDTA was added to 11 mM and the reaction was heated to 70° C., for 30 minutes. The material was then run on a 1% gel to test if the covalently closed ends have formed. If the covalently closed ends were not properly formed, the reaction will be digested by ExoV. A sample gel is depicted in FIG. 7. Linear DNA (lane 3) is digested by ExoV, while covalently closed DNA (lanes 9-10) is not digested.

TABLE 7

| ExoV reaction | |
| --- | --- |
| ExoV Digestion | 25 uL Reaction |
| DNA | 200 ng DNA |
| Cutsmart (10×) | 2.5 uL |
| ATP (10 mM) | 2.5 uL (1 mM) |
| Exonuclease V | 0.5 uL |
| Nuelase free H2O | Up to 25 uL |

Example 5: Protocol for Generating Covalently Closed DNA

DNA was amplified in a 96 well plate using the protocol in Table 8A. The primers used were NEOG_dumbbell+F

```
NEOG_dumbbell + F
                                  (SEQ ID NO: 7)
(AAACCUCAAAAGAGGUUCGAGACCACTCCAG)
and NEOG_dumbbell + R
                                  (SEQ ID NO: 8)
(AAACCUCAAAAGAGGUUCGCAGTAAGGGGC).
```

TABLE 8A

| Reaction parameters | | | |
| --- | --- | --- | --- |
| Kapa-Uracil PCR 100 uL Reaction | 1X (uL) | Initial Conc | Final Conc |
| 10 uM covalently closed Uracil F Primer | 6 | 10 uM | 0.6 uM |
| 10 uM covalently closed Uracil R Primer | 6 | 10 uM | 0.6 uM |
| Kapa-Uracil 2× Master Mix | 50 | 2× | 1× |
| HyPure Molecular Biology Grade Water | 37 | | |
| Mastermix total | 99 | | |
| Clonal DNA template (2.5 ng/uL) | 1 | | 2.5 ng |

TABLE 8B

| Amplification reagents | |
| --- | --- |
| Component | 100 uL Reaction |
| Nuclease-free water | Up to 100 uL total |
| 10× Standard Taq Reaction Buffer | 10 |
| 10 mM dNTPs | 2 |
| 10 μM Forward Primer | 2 |
| 10 μM Reverse Primer | 2 |
| Hot Start Taq DNA Polymerase | 0.5 |
| Template DNA (2.5 ng) | x |

TABLE 8C

| Amplification reaction parameters | | |
| --- | --- | --- |
| Step | Temp. | Time |
| Initial Denaturation | 95° C. | 30 seconds |
| 20× | 95° C. | 20 seconds |
| | 65° C. | 15 seconds |
| | 68° C. | 3 minutes (1 minute/kb) |
| Final Extension | 68° C. | 3 minutes |
| Hold | 4° C. | |

Amplification reactions were prepared according to Table 8B and subject to amplification according to the cycling conditions listed in Table 8C.

The ccDNA generated by amplification using Taq polymerase was then subject to Klenow blunting according to the reagents and parameters in Table 8D and Table 8E.

TABLE 8D

| Klenow blunting reagents | | |
| --- | --- | --- |
| Component | Volume | Final Concentration |
| ddH20 | 63.67 | |
| 10× CutSmart Buffer | 10 | 1× |
| DNA Polymerase I, Large (Klenow) Fragment 5 U/uL | 1 | 0.05 U/uL |
| Taq Amplified dsDNA (5 ug) | 25 | |
| dNTP | 0.33 | 33 uM |
| Total Volume | 100 uL | |

TABLE 8E

| Klenow blunting reaction parameters | |
| --- | --- |
| Temperature | Time |
| 25° C. | 15 minutes |
| 4° C. | ~ |
| Spike in 2 uL of 0.5 M EDTA (final concentration ~10 uM) to inactivate reaction | |
| 75° C. | 10 minutes |
| 4° C. | ~ |

Six PCR reactions were pooled together and purified using SPRI purification. The eluted DNA is analyzed using a Bioanalyzer and Qubit to identify yield and quality. Yield is depicted in Table 9. Quality is depicted in FIGS. 8A-8H.

TABLE 9

| | | | Yield (ug) in |
| --- | --- | --- | --- |
| Sample | PCR Volume. | Conc (ng/uL) | 25 uL water |
| 1 | 100 uL | 378 | 9.45 |
| 2 | 100 uL | 346 | 8.65 |
| 3 | 100 uL | 340 | 8.5 |
| 4 | 100 uL | 366 | 9.15 |
| 5 | 100 uL | 414 | 10.35 |
| 6 | 100 uL | 360 | 9 |
| 7 | 50 uL | 232 | 5.8 |
| 8 | 50 uL | 274 | 6.85 |

A USER digest was performed to excise the uracils from the covalently closed nucleic acid primers and allow the formation of the hairpin structures. 20 uL of purified Kapa-U PCR DNA (1-8 ug) is combined with 2.5 uL of 10× Cutsmart buffer and 2.5 uL of USER. The reaction was incubated at 37° C., for 90 minutes.

A T4 ligation was performed to seal the nicks left by the uracil and hairpin after the digest. The reaction components listed in Table 10 were combined to create a master mix, then 25 uL of each Ligation mix and 25 uL was combined into each well of the 96 well plate containing the USER treated and annealed DNA. The plate was sealed, spun down, mixed, and spun down again. The reaction was incubated at 16° C., for 1 hour.

TABLE 10

| Ligation reaction | |
| --- | --- |
| T4 ligation | 1× (50 uL) |
| T4 ligase buffer | 5 |
| T4 ligase (400,000 units/mL) | 1 |
| Water | 19 |
| Subtotal | 25 |
| USER Treated and annealed DNA | 8 |

Figure 9A:
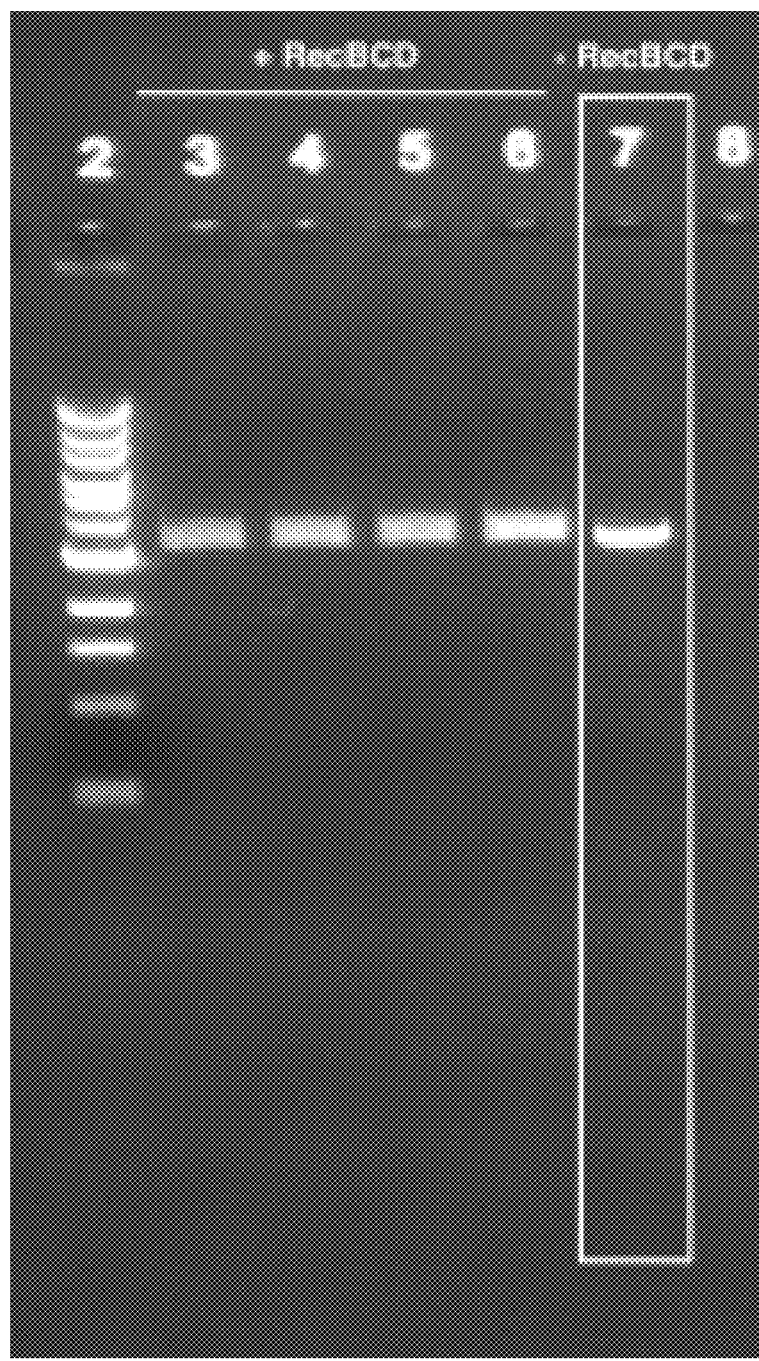
FIGS. 9A-9B depict the results of digesting covalently closed DNA with Exonuclease V.
Figure 9B:
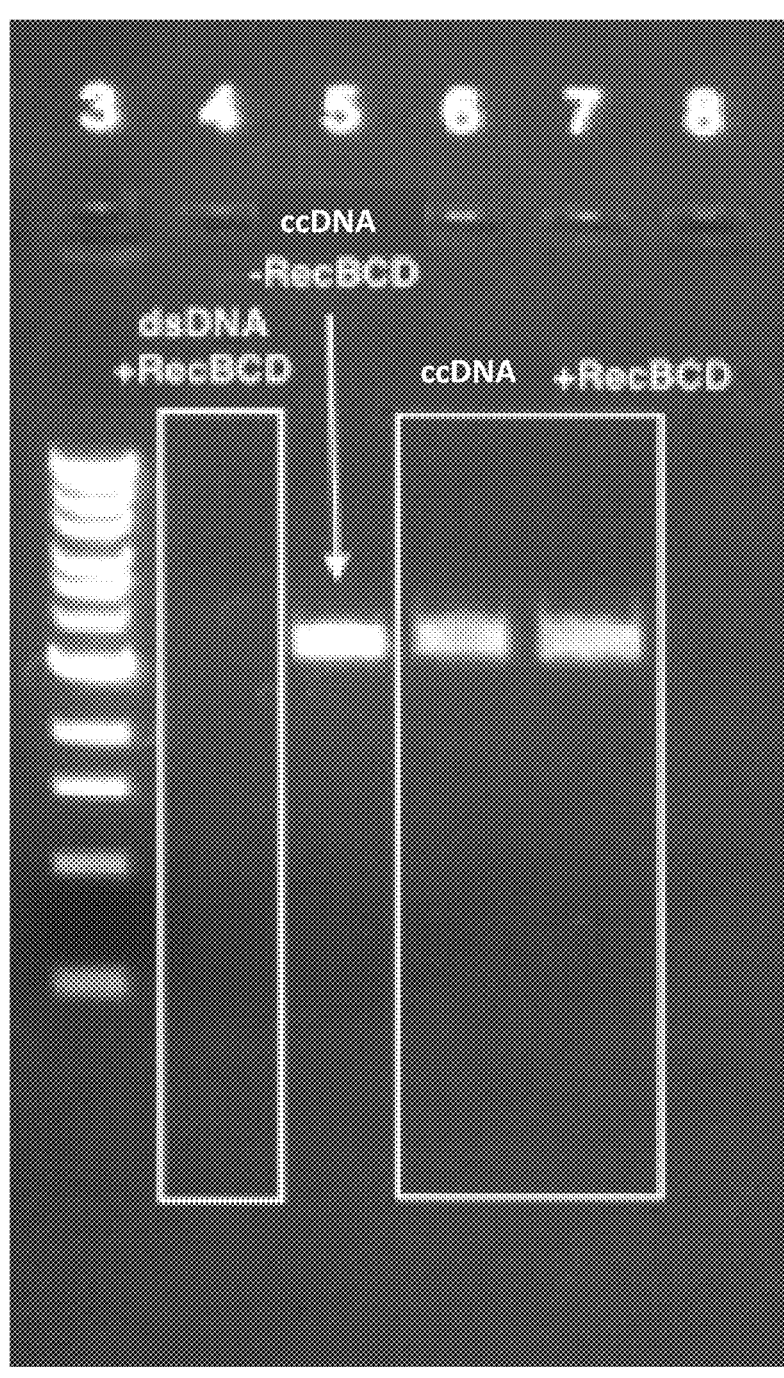

200 ng of the material was run through an ExoV digested to test for completion of the covalently closed nucleic acid. The components in Table 11 were combined and incubated at 37° C., for 30 minutes. To stop the reaction. EDTA was added to 11 mM and the reaction was heated to 70° C., for 30 minutes. The material was then run on a 1% gel to test if the covalently closed ends have formed. The results are depicted in FIGS. 9A-9B. FIG. 9A shows that no digestion occurred in the 4 samples incubated with RecBCD compared to the sample incubated without RecBCD (lane 8). FIG. 9B shows a comparison between two sets of covalently closed DNA (ccDNA) compared to a negative control (dsDNA, no RecBCD). The percent of undigested DNA was 87.7% for lane 6 and 89.7% for lane 7, compared to the negative control.

TABLE 11

| ExoV reaction | |
| --- | --- |
| ExoV Digestion | 25 uL Reaction |
| DNA | 200 ng DNA |
| Catsmart (10×) | 2.5 uL |
| ATP (10 mM) | 2.5 uL (1 mM) |
| Exonuclease V | 0.5 uL |
| Nuclease free H2O | Up to 25 uL |

Figure 10A:
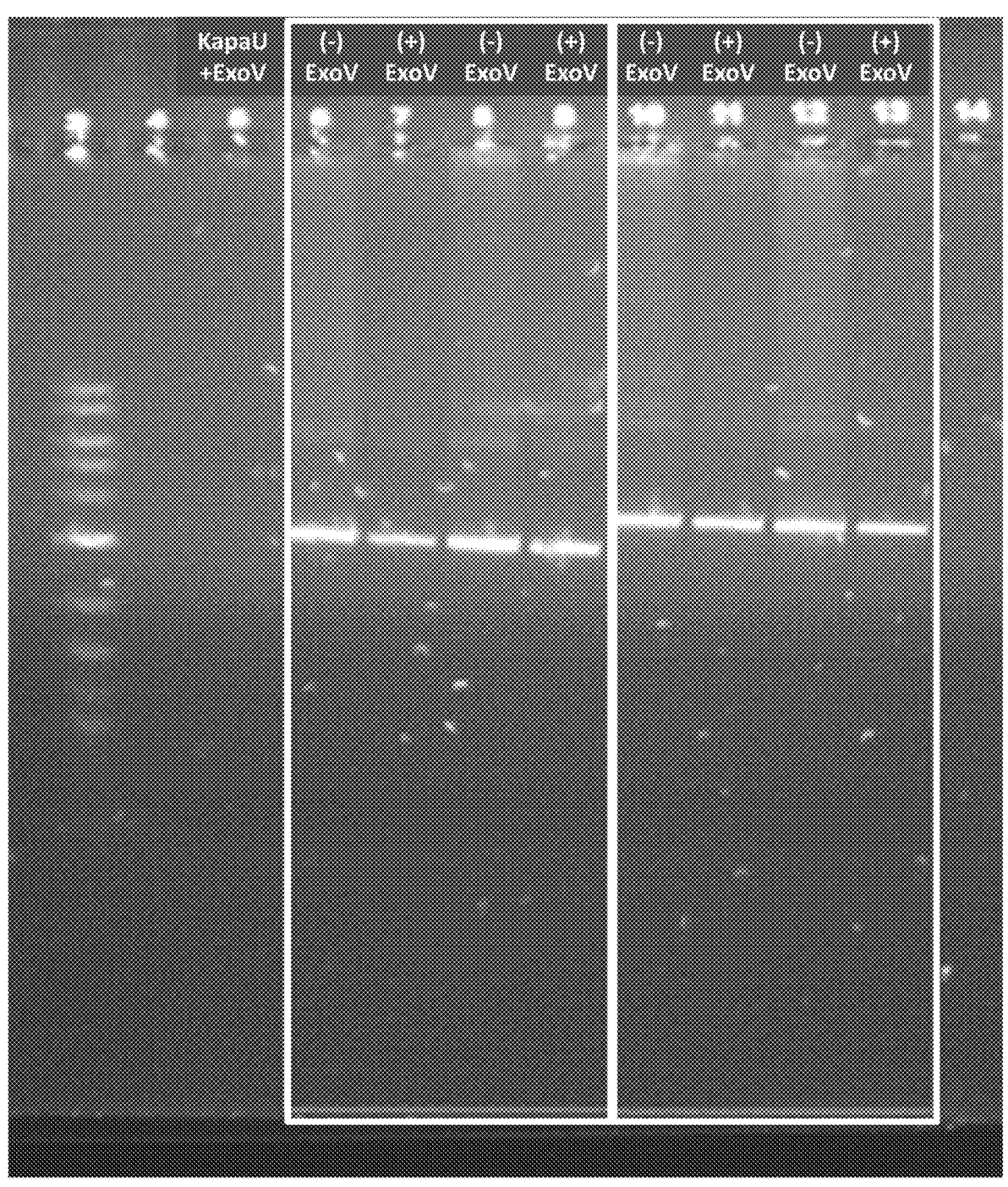
FIG. 10A depicts covalently closed DNA formation as tested by Exonuclease V digestion using the original hairpin sequences. Lane 3 is the ladder; lane 4 is blank; lane 6 is linear DNA incubated with ExoV; lane 6 is Template 1, Replicate 1 untreated with ExoV; lane 7 is Template 1, Replicate 1 treated with ExoV; lane 8 is Template 1, Replicate 2 untreated with ExoV; lane 9 is Template 1, Replicate 2 treated with ExoV; lane 10 is Template 2, Replicate 1 untreated with ExoV; lane 11 is Template 2, Replicate 1 treated with ExoV; lane 12 is Template 2, Replicate 2 untreated with ExoV; lane 13 is Template 2, Replicate 2 treated with ExoV.
Figure 10B:
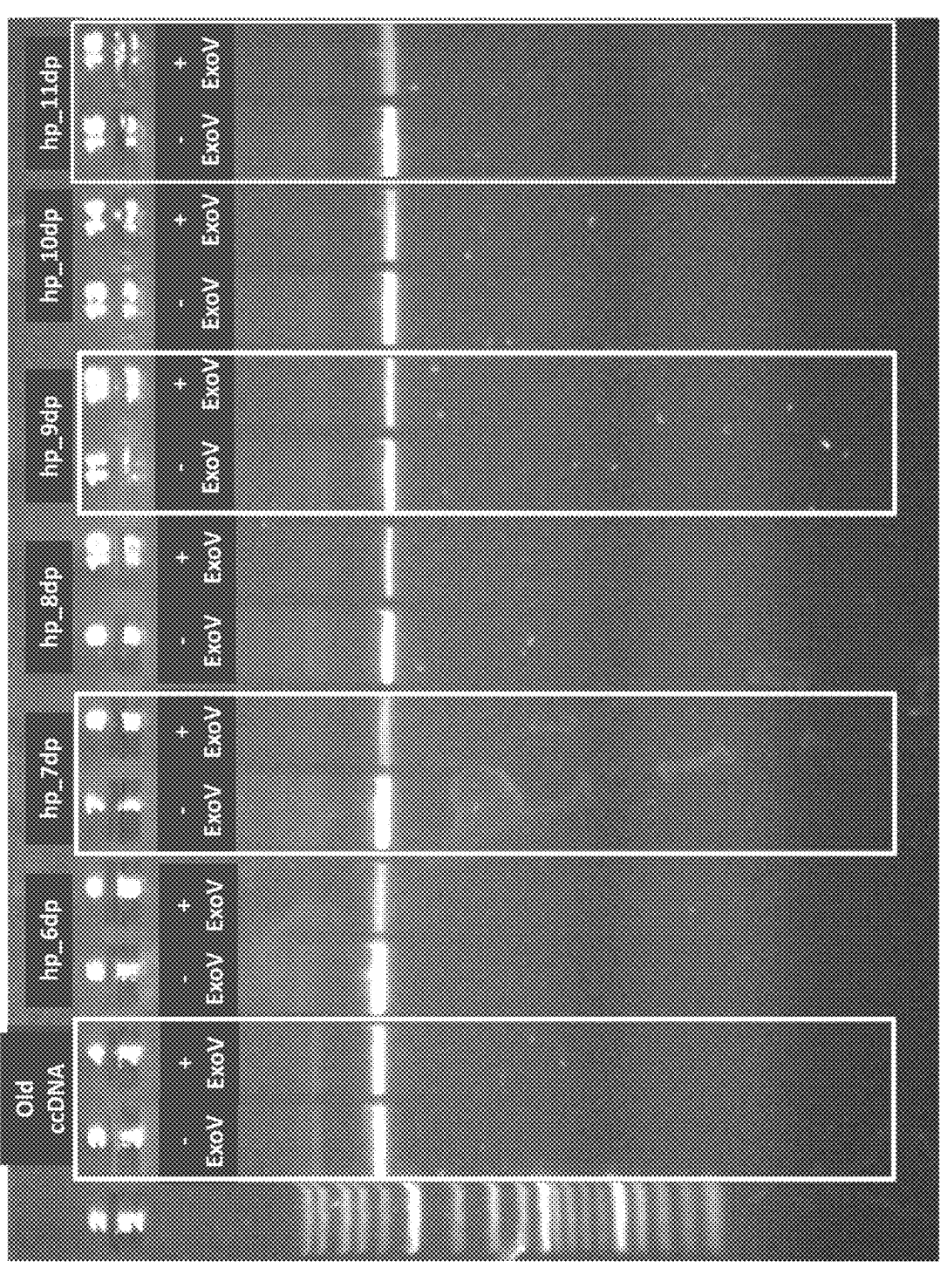
FIG. 10B depicts covalently closed DNA (ccDNA) formation as tested by Exonuclease V digestion using variant covalently closed sequences. Lane 2 is the ladder, lanes 3-4 show ccDNA formation using the original hairpin sequence, lines 5-6 show ccDNA formation using variant 6, lanes 7-8 show ccDNA formation using variant 7, lanes 9-10 show ccDNA formation using variant 8, lanes 11-12 show ccDNA formation using variant 9, lanes 13-14 show ccDNA formation using variant 10, and lanes 15-16 show ccDNA formation using variant 11. Even numbered lanes contained ccDNA treated with ExoV and Odd numbered lanes contain untreated ccDNA.
Figure 10C:
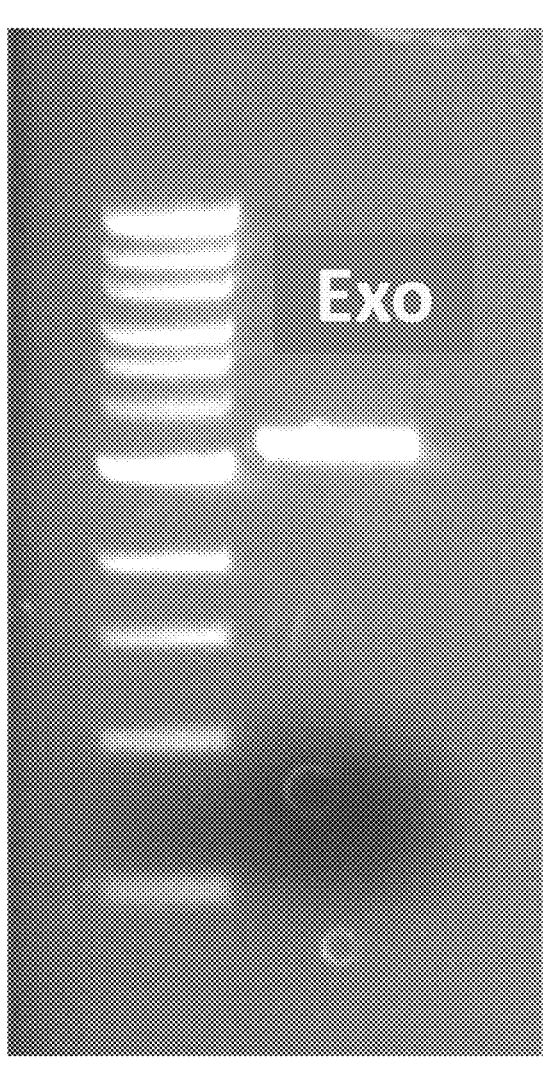
FIG. 10C is a gel depicting formation of ccDNA following Exonuclease V digestion.

Example 6: The Effects of Different Hairpin Sequences on Formation of Covalently Closed DNA Covalently closed DNA was prepared using the methods described above. Different hairpin sequences listed in Table 12 are tested. The formation of ccDNA is confirmed by Exonuclease V digestion. The results are depicted in FIG. 10A-10C. FIG. 10A depicts hairpin formation using the original hairpin sequence. Lane 5 shows digestion of linear DNA incubated with ExoV. Lanes 6-9 show reactions using template 1, which lanes 10-13 show reactions using template 2. Two replicates were performed for each template. FIG. 10B compares the original covalently closed nucleic acid sequences to variants 6-11. Lanes 3-4 show ccDNA formation using the original hairpin sequence, lines 5-6 show ccDNA formation using variant 6, lanes 7-8 show ccDNA formation using variant 7, lanes 9-10 show ccDNA formation using variant 8, lanes 11-12 show ccDNA formation using variant 9, lanes 13-14 show ccDNA formation using variant 10, and lanes 15-16 show ccDNA formation using variant 11. Even numbered lanes contained ccDNA treated with ExoV and Odd numbered lanes contain untreated ccDNA. FIG. 10C depicts formation of ccDNA following Exonuclease V digestion.

TABLE 12

| Hairpin sequences | | |
| --- | --- | --- |
| Hairpin sequence | SEQ ID NO. | Sequence |
| Original | 9 | AAACCTCAAAAGAGGTTTCG |
| Variant 1 | 10 | GTACACTTTTTATAAAATGTACGC |
| Variant 2 | 11 | CTCTGTCAAAAGACAGAGGC |
| Variant 3 | 12 | CCTCTCCTTTTGGAGAGGGC |
| Variant 4 | 13 | GTGCAAGAAAAACTTGCACGC |
| Variant 5 | 14 | GTGCTAGAAAATCTAGCACGC |
| Variant 6 | 15 | AGCGAACTCAAAAGAGAACGCTGC |
| Variant 7 | 16 | AAGCAATGAGAAAACTCAAAGCTTGC |
| Variant 8 | 17 | AGTCAAGTACAAAAGTACAAGACTGC |

TABLE 12-continued

| Hairpin sequences | | |
|---|---|---|
| Hairpin sequence | SEQ ID NO. | Sequence |
| Variant 9 | 18 | AGTCAAGTACAAAGTACAAGACTGC |
| Variant 10 | 19 | AGTCGAAAGTACAAAAGTACAAACGACTGC |
| Variant 11 | 20 | AGTCGAAAGTACAAAAAGTACAAACGACTGC |

Example 7: Transfection of Cultured Human Cells with Covalently Closed DNA

Figure 11A:
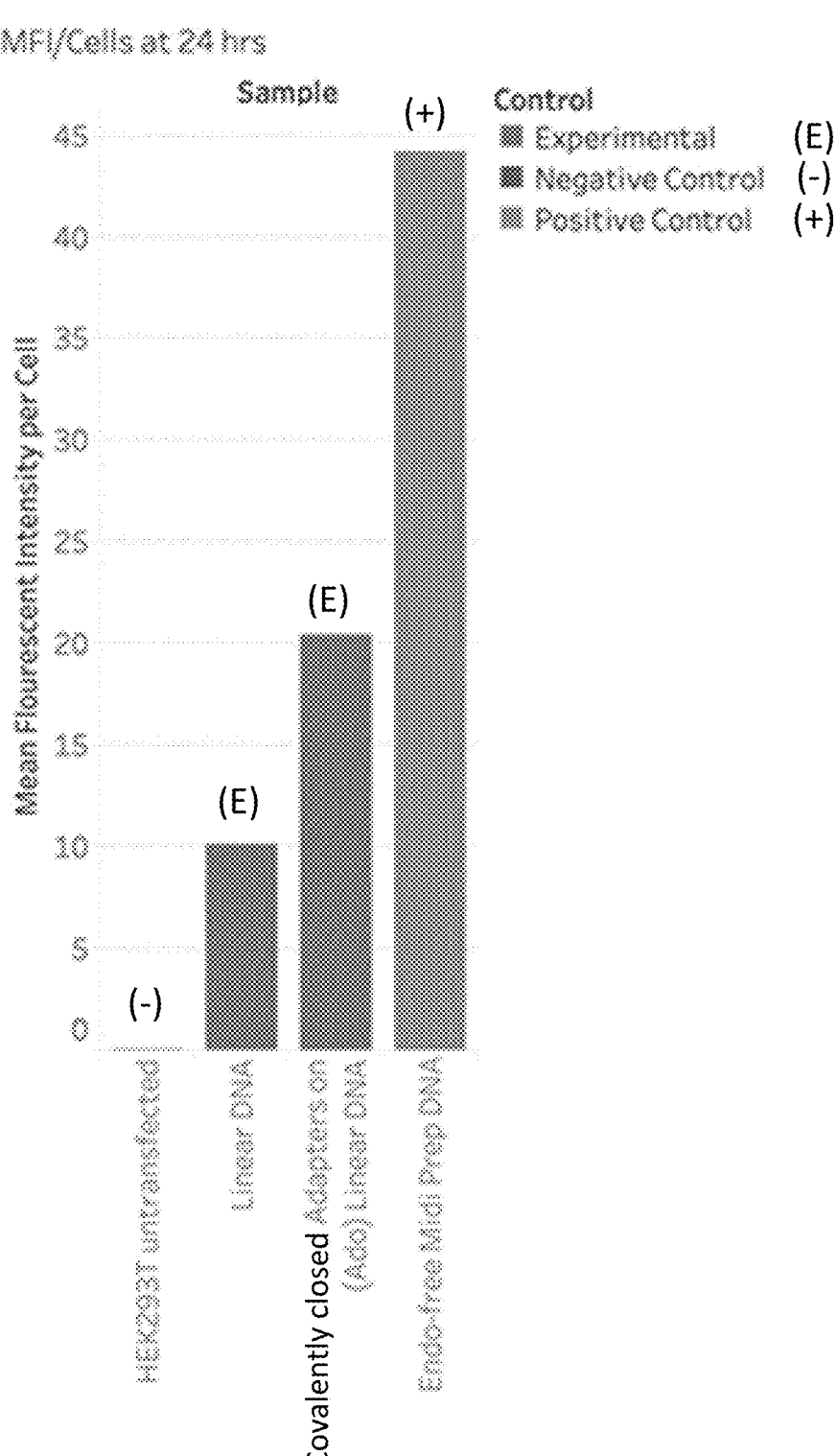
FIG. 11A depicts the mean fluorescent intensity of HEK293 cells transfected with linear DNA, covalently closed DNA or plasmid DNA.
Figure 11B:
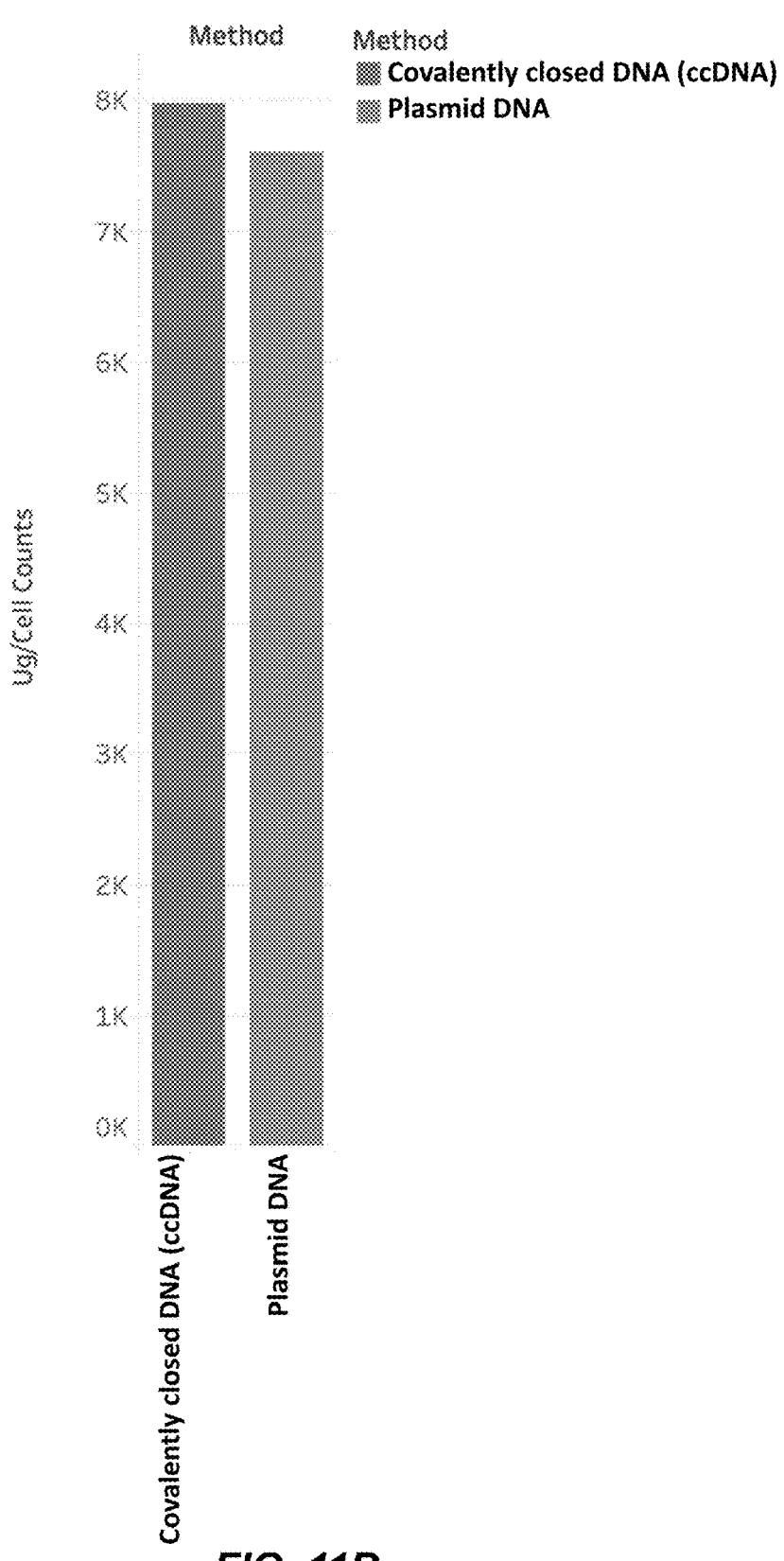
FIG. 11B depicts the yield in ug/cell of IgG purified from cells transfected with covalently closed DNA or plasmid DNA.

Hek293 cells were cultured under standard conditions. Cells were transfected with linear DNA, covalently closed DNA, or endonuclease-free midiPrep DNA containing a GFP sequence. FIG. 11A depicts GFP expression after 24 hours. Cells transfected with ccDNA showed a higher mean fluorescent intensity than cells transfected with linear DNA. IgG yields were also purified from Hek293 cells transfected with ccDNA and with Plasmid DNA. As depicted in FIG. 11B, the IgG yield was greater in cells transfected with ccDNA than cells transfected with plasmids.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What we claim is:

1. A method for assembly of a covalently closed double stranded nucleic acid, comprising:
   (a) providing a double stranded nucleic acid;
   (b) amplifying the double stranded nucleic acid using a primer comprising one or more uracils to generate a double stranded nucleic acid comprising one or more uracils at a 5' end and a 3' end;
   (c) digesting the double stranded nucleic acid comprising one or more uracils at the 5' end and the 3' end using a glycosylase and a glycosylase-lyase to generate a double stranded nucleic acid comprising a loop structure at the 5' end and the 3' end; and
   (d) ligating gaps in the double stranded nucleic acid comprising the loop structure at the 5' end and the 3' end using a ligase to generate the covalently closed double stranded nucleic acid,
   wherein the primer comprises a nucleic acid sequence according to SEQ ID NO: 5, SEQ ID NO: 6, SEQ ID NO: 7, or SEQ ID NO: 8.

2. The method of claim 1, wherein the double stranded nucleic acid is deoxyribonucleic acid.

3. The method of claim 1, wherein the double stranded nucleic acid is linear.

4. The method of claim 1, wherein the glycosylase comprises base excision activity.

5. The method of claim 4, wherein the base excision activity of the glycosylase generates an abasic site.

6. The method of claim 1, wherein the glycosylase excises the one or more uracils.

7. The method of claim 1, wherein the glycosylase is AlkA, 3-methyladenine DNA glycosylase II, Mag1, MPG, SMUG1, MBD4, NTHL1, uracil DNA glycosylases, helix-hairpin-helix (HhH) glycosylases, or 3-methyl-purine glycosylase (MPG).

8. The method of claim 5, wherein the glycosylase-lyase breaks the phosphodiester backbone at a 3' and 5' sides of the abasic site.

9. The method of claim 1, wherein the glycosylase-lyase is Endonuclease VIII.

10. The method of claim 1, wherein the loop structure comprises at most about 40 bases.

11. The method of claim 1, wherein the loop structure comprises a sequence according to any one of SEQ ID NOs: 9-20.

12. The method of claim 1, wherein step (c) comprises excision of the one or more uracils.

13. The method of claim 1, wherein the method does not require heating between step (c) and step (d).

14. A covalently closed double stranded nucleic acid generated by the method of claim 1.

15. A method for assembly of a covalently closed double stranded nucleic acid, comprising:
   (a) providing a double stranded nucleic acid;
   (b) amplifying the double stranded nucleic acid using a primer comprising one or more uracils to generate a double stranded nucleic acid comprising one or more uracils at a 5' end and a 3' end;

(c) digesting the double stranded nucleic acid comprising one or more uracils at the 5' end and the 3' end using a glycosylase and a glycosylase-lyase to generate a double stranded nucleic acid comprising a loop structure at the 5' end and the 3' end; and (d) ligating gaps in the double stranded nucleic acid comprising the loop structure at the 5' end and the 3' end using a ligase to generate the covalently closed double stranded nucleic acid, wherein the loop structure comprises a nucleic acid sequence according to SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, or SEQ ID NO: 20.

16. The method of claim 15, wherein the double stranded nucleic acid is deoxyribonucleic acid.

17. The method of claim 15, wherein the double stranded nucleic acid is linear.

18. The method of claim 15, wherein the glycosylase comprises base excision activity.

19. The method of claim 18, wherein the base excision activity of the glycosylase generates an abasic site.

20. The method of claim 15, wherein the glycosylase excises the one or more uracils.

21. The method of claim 15, wherein the glycosylase is AlkA, 3-methyladenine DNA glycosylase II, Mag1, MPG, SMUG1, MBD4, NTHL1, uracil DNA glycosylases, helix-hairpin-helix (HhH) glycosylases, or 3-methyl-purine glycosylase (MPG).

22. The method of claim 19, wherein the glycosylase-lyase breaks the phosphodiester backbone at a 3' and 5' sides of the abasic site.

23. The method of claim 15, wherein the glycosylase-lyase is Endonuclease VIII.

24. The method of claim 15, wherein the loop structure comprises at most about 40 bases.

25. The method of claim 15, wherein step (c) comprises excision of the one or more uracils.

26. The method of claim 15, wherein the method does not require heating between step (c) and step (d).

27. A covalently closed double stranded nucleic acid generated by the method of claim 15.

* * * * *

```
                          SEQUENCE LISTING

Sequence total quantity: 20
SEQ ID NO: 1             moltype = DNA  length = 62
FEATURE                  Location/Qualifiers
source                   1..62
                         mol_type = other DNA
                         organism = synthetic construct
modified_base            51
                         mod_base = OTHER
                         note = Thymidine-succinyl hexamide CED phosphoramidite
modified_base            52
                         mod_base = OTHER
                         note = Thymidine-succinyl hexamide CED phosphoramidite
SEQUENCE: 1
agacaatcaa ccatttgggg tggacagcct tgacctctag acttcggcat nnttttttttt  60
tt                                                                    62

SEQ ID NO: 2             moltype = DNA  length = 112
FEATURE                  Location/Qualifiers
source                   1..112
                         mol_type = other DNA
                         organism = synthetic construct
modified_base            101
                         mod_base = OTHER
                         note = Thymidine-succinyl hexamide CED phosphoramidite
modified_base            102
                         mod_base = OTHER
                         note = Thymidine-succinyl hexamide CED phosphoramidite
SEQUENCE: 2
cgggatcctt atcgtcatcg tcgtacagat cccgacccat ttgctgtcca ccagtcatgc  60
tagccatacc atgatgatga tgatgatgag aacccgcat nnttttttttt tt           112

SEQ ID NO: 3             moltype = DNA  length = 19
FEATURE                  Location/Qualifiers
source                   1..19
                         mol_type = other DNA
                         organism = synthetic construct
SEQUENCE: 3
atgcgggtt ctcatcatc                                                   19

SEQ ID NO: 4             moltype = DNA  length = 20
FEATURE                  Location/Qualifiers
source                   1..20
                         mol_type = other DNA
                         organism = synthetic construct
SEQUENCE: 4
cgggatcctt atcgtcatcg                                                 20

SEQ ID NO: 5             moltype = RNA  length = 42
FEATURE                  Location/Qualifiers
source                   1..42
                         mol_type = other RNA
                         organism = synthetic construct
SEQUENCE: 5
```

-continued

```
aaacctcaaa agaggtttcg ctgatcgagt gtagccagat ct                          42

SEQ ID NO: 6          moltype = RNA   length = 40
FEATURE               Location/Qualifiers
source                1..40
                      mol_type = other RNA
                      organism = synthetic construct
SEQUENCE: 6
aaacctcaaa agaggtttcg cctgcaggat agctgacgac                             40

SEQ ID NO: 7          moltype = RNA   length = 32
FEATURE               Location/Qualifiers
source                1..32
                      mol_type = other RNA
                      organism = synthetic construct
SEQUENCE: 7
aaacctcaaa agaggtttcg agaccactcc ag                                     32

SEQ ID NO: 8          moltype = RNA   length = 31
FEATURE               Location/Qualifiers
source                1..31
                      mol_type = other RNA
                      organism = synthetic construct
SEQUENCE: 8
aaacctcaaa agaggtttcg cagtaagggg c                                      31

SEQ ID NO: 9          moltype = DNA   length = 20
FEATURE               Location/Qualifiers
source                1..20
                      mol_type = other DNA
                      organism = synthetic construct
SEQUENCE: 9
aaacctcaaa agaggtttcg                                                   20

SEQ ID NO: 10         moltype = DNA   length = 23
FEATURE               Location/Qualifiers
source                1..23
                      mol_type = other DNA
                      organism = synthetic construct
SEQUENCE: 10
gtacattttt ataaaatgta cgc                                               23

SEQ ID NO: 11         moltype = DNA   length = 20
FEATURE               Location/Qualifiers
source                1..20
                      mol_type = other DNA
                      organism = synthetic construct
SEQUENCE: 11
ctctgtcaaa agacagaggc                                                   20

SEQ ID NO: 12         moltype = DNA   length = 20
FEATURE               Location/Qualifiers
source                1..20
                      mol_type = other DNA
                      organism = synthetic construct
SEQUENCE: 12
cctctccttt tggagagggc                                                   20

SEQ ID NO: 13         moltype = DNA   length = 21
FEATURE               Location/Qualifiers
source                1..21
                      mol_type = other DNA
                      organism = synthetic construct
SEQUENCE: 13
gtgcaagaaa aacttgcacg c                                                 21

SEQ ID NO: 14         moltype = DNA   length = 21
FEATURE               Location/Qualifiers
source                1..21
                      mol_type = other DNA
                      organism = synthetic construct
SEQUENCE: 14
gtgctagaaa atctagcacg c                                                 21

SEQ ID NO: 15         moltype = DNA   length = 24
FEATURE               Location/Qualifiers
source                1..24
                      mol_type = other DNA
                      organism = synthetic construct
```

-continued

```
SEQUENCE: 15
agcgaactca aaagagaacg ctgc                                                24

SEQ ID NO: 16          moltype = DNA  length = 26
FEATURE                Location/Qualifiers
source                 1..26
                       mol_type = other DNA
                       organism = synthetic construct
SEQUENCE: 16
aagcaatgag aaaactcaaa gcttgc                                              26

SEQ ID NO: 17          moltype = DNA  length = 26
FEATURE                Location/Qualifiers
source                 1..26
                       mol_type = other DNA
                       organism = synthetic construct
SEQUENCE: 17
agtcaagtac aaaagtacaa gactgc                                              26

SEQ ID NO: 18          moltype = DNA  length = 25
FEATURE                Location/Qualifiers
source                 1..25
                       mol_type = other DNA
                       organism = synthetic construct
SEQUENCE: 18
agtcaagtac aaagtacaag actgc                                               25

SEQ ID NO: 19          moltype = DNA  length = 30
FEATURE                Location/Qualifiers
source                 1..30
                       mol_type = other DNA
                       organism = synthetic construct
SEQUENCE: 19
agtcgaaagt acaaaagtac aaacgactgc                                          30

SEQ ID NO: 20          moltype = DNA  length = 32
FEATURE                Location/Qualifiers
source                 1..32
                       mol_type = other DNA
                       organism = synthetic construct
SEQUENCE: 20
agtcgaaagt acaaaaaagt acaaacgact gc                                       32
```